(12) United States Patent
Badower et al.

(10) Patent No.: US 11,141,108 B2
(45) Date of Patent: *Oct. 12, 2021

(54) METHODS AND APPARATUS TO GATHER AND ANALYZE ELECTROENCEPHALOGRAPHIC DATA

(71) Applicant: The Nielsen Company (US), LLC, New York, NY (US)

(72) Inventors: Yakob Badower, Frankfurt am Main (DE); Bradley R. Lawrence, Tampa, FL (US); Marcos Male, Tampa, FL (US); Marko Jovanovic, Berlin (DE); Jakob Olrik, Berlin (DE)

(73) Assignee: NIELSEN CONSUMER LLC, New York, NY (US)

( * ) Notice: Subject to any disclaimer, the term of this patent is extended or adjusted under 35 U.S.C. 154(b) by 1179 days.

This patent is subject to a terminal disclaimer.

(21) Appl. No.: 15/449,564

(22) Filed: Mar. 3, 2017

(65) Prior Publication Data

US 2017/0172501 A1    Jun. 22, 2017

Related U.S. Application Data

(63) Continuation of application No. 14/293,557, filed on Jun. 2, 2014, now Pat. No. 9,622,702.

(Continued)

(51) Int. Cl.
*A61B 5/00* (2006.01)
*A61B 5/291* (2021.01)
*A61B 5/316* (2021.01)

(52) U.S. Cl.
CPC ............ *A61B 5/6803* (2013.01); *A61B 5/291* (2021.01); *A61B 5/316* (2021.01);

(Continued)

(58) Field of Classification Search
CPC . A61B 5/6803; A61B 5/04012; A61B 5/0487; A61B 2562/0215;

(Continued)

(56) References Cited

U.S. PATENT DOCUMENTS 2,409,033 A    10/1946 Garceau
2,549,836 A    4/1951 McIntyre et al.

(Continued)

FOREIGN PATENT DOCUMENTS

CN    1538823    10/2004
CN    102791194    11/2012

(Continued)

OTHER PUBLICATIONS

Aaker et al., "Warmth in Advertising: Measurement, Impact, and Sequence Effects," Journal of Consumer Research, vol. 12, No. 4, pp. 365-381, Mar. 1986, 18 pages.

(Continued)

*Primary Examiner* — Eun Hwa Kim
*Assistant Examiner* — Adam Z Minchella
(74) *Attorney, Agent, or Firm* — Hanley, Flight & Zimmerman, LLC

(57) ABSTRACT

Example headsets and methods for gathering electroencephalographic signals are disclosed herein. An example headset includes an adjustment assembly including a first support to be disposed on a first side of a head of a person and a second support to be disposed on a second side of the head of the person. The example headset also includes an adjustor operatively coupled to the first support. Further, the example headset includes an electrode strip and a tension strap having a first end operatively coupled to the adjustor and a second end operatively coupled to the second support.

20 Claims, 24 Drawing Sheets

Related U.S. Application Data

(60) Provisional application No. 61/974,847, filed on Apr. 3, 2014.

(52) U.S. Cl.
CPC .......... *A61B 2560/0468* (2013.01); *A61B 2562/0215* (2017.08); *A61B 2562/043* (2013.01); *A61B 2562/227* (2013.01)

(58) Field of Classification Search
CPC ...... A61B 2560/0468; A61B 2562/043; A61B 2562/227; A61B 5/6831; A61B 5/0476; A61B 5/0478; A61B 5/6816; A61B 5/6838; A61B 2560/0443; A61B 2562/04; A61B 2562/225; A41F 1/002
See application file for complete search history.

(56) References Cited

U.S. PATENT DOCUMENTS

| | | |
|---|---|---|
| 3,490,439 A | 1/1970 | Rolston |
| 3,508,541 A | 4/1970 | Westbrook et al. |
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,033,334 A | 7/1977 | Fletcher et al. |
| 4,075,657 A | 2/1978 | Weinblatt |
| 4,149,716 A | 4/1979 | Scudder |
| 4,201,224 A | 5/1980 | John |
| 4,213,463 A | 7/1980 | Osenkarski |
| 4,279,258 A | 7/1981 | John |
| 4,397,331 A | 8/1983 | Medlar |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,640,290 A | 2/1987 | Sherwin |
| 4,683,892 A | 8/1987 | Johansson et al. |
| 4,695,879 A | 9/1987 | Weinblatt |
| 4,709,702 A | 12/1987 | Sherwin |
| 4,736,751 A | 4/1988 | Gevins et al. |
| 4,755,045 A | 7/1988 | Borah et al. |
| 4,770,180 A | 9/1988 | Schmidt et al. |
| 4,800,888 A | 1/1989 | Itil et al. |
| 4,802,484 A | 2/1989 | Friedman et al. |
| 4,846,190 A | 7/1989 | John |
| 4,865,038 A | 9/1989 | Rich et al. |
| 4,885,687 A | 12/1989 | Carey |
| 4,894,777 A | 1/1990 | Negishi et al. |
| 4,913,160 A | 4/1990 | John |
| 4,931,934 A | 6/1990 | Snyder |
| 4,936,306 A | 6/1990 | Doty |
| 4,955,388 A | 9/1990 | Silberstein |
| 4,967,038 A | 10/1990 | Gevins et al. |
| 4,974,602 A | 12/1990 | Abraham-Fuchs et al. |
| 4,987,903 A | 1/1991 | Keppel et al. |
| 5,003,986 A | 4/1991 | Finitzo et al. |
| 5,010,891 A | 4/1991 | Chamoun |
| 5,024,235 A | 6/1991 | Ayers |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,339,826 A | 8/1994 | Schmidt et al. |
| 5,345,934 A | 9/1994 | Highe et al. |
| 5,348,006 A | 9/1994 | Tucker |
| 5,355,883 A | 10/1994 | Ascher |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,406,957 A | 4/1995 | Tansey |
| 5,447,166 A | 9/1995 | Gevins |
| 5,450,855 A | 9/1995 | Rosenfeld |
| 5,452,718 A | 9/1995 | Clare et al. |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,579,774 A | 12/1996 | Miller et al. |
| 5,601,090 A | 2/1997 | Musha |
| 5,617,855 A | 4/1997 | Waletzky et al. |
| 5,645,577 A | 7/1997 | Froberg et al. |
| 5,649,061 A | 7/1997 | Smyth |
| 5,655,534 A | 8/1997 | Ilmoniemi |
| 5,676,138 A | 10/1997 | Zawilinski |
| 5,692,906 A | 12/1997 | Corder |
| 5,697,369 A | 12/1997 | Long, Jr. et al. |
| 5,720,619 A | 2/1998 | Fisslinger |
| 5,724,987 A | 3/1998 | Gevins et al. |
| 5,729,205 A | 3/1998 | Kwon |
| 5,736,986 A | 4/1998 | Sever, Jr. |
| 5,740,035 A | 4/1998 | Cohen et al. |
| 5,740,812 A | 4/1998 | Cowan |
| 5,762,611 A | 6/1998 | Lewis et al. |
| 5,771,897 A | 6/1998 | Zufrin |
| 5,772,591 A | 6/1998 | Cram |
| 5,774,591 A | 6/1998 | Black et al. |
| 5,787,187 A | 7/1998 | Bouchard et al. |
| 5,788,648 A | 8/1998 | Nadel |
| 5,800,351 A | 9/1998 | Mann |
| 5,812,642 A | 9/1998 | Leroy |
| 5,817,029 A | 10/1998 | Gevins et al. |
| 5,848,399 A | 12/1998 | Burke |
| 5,868,670 A | 2/1999 | Randell |
| 5,945,863 A | 8/1999 | Coy |
| 5,954,642 A | 9/1999 | Johnson et al. |
| 5,961,332 A | 10/1999 | Joao |
| 5,983,129 A | 11/1999 | Cowan et al. |
| 5,983,214 A | 11/1999 | Lang et al. |
| 6,001,065 A | 12/1999 | DeVito |
| 6,002,957 A | 12/1999 | Finneran |
| 6,003,156 A | 12/1999 | Anderson |
| 6,021,346 A | 2/2000 | Ryu et al. |
| 6,052,619 A | 4/2000 | John |
| 6,099,319 A | 8/2000 | Zaltman et al. |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,171,239 B1 | 1/2001 | Humphrey |
| 6,173,260 B1 | 1/2001 | Slaney |
| 6,175,753 B1 | 1/2001 | Menkes et al. |
| 6,228,038 B1 | 5/2001 | Claessens |
| 6,233,472 B1 | 5/2001 | Bennett et al. |
| 6,236,885 B1 | 5/2001 | Hunter et al. |
| 6,254,536 B1 | 7/2001 | DeVito |
| 6,259,889 B1 | 7/2001 | LaDue |
| 6,280,198 B1 | 8/2001 | Calhoun et al. |
| 6,286,005 B1 | 9/2001 | Cannon |
| 6,289,234 B1 | 9/2001 | Mueller |
| 6,292,688 B1 | 9/2001 | Patton |
| 6,301,493 B1 | 10/2001 | Marro et al. |
| 6,309,342 B1 | 10/2001 | Blazey et al. |
| 6,315,569 B1 | 11/2001 | Zaltman |
| 6,322,368 B1 | 11/2001 | Young et al. |
| 6,330,470 B1 | 12/2001 | Tucker et al. |

(56) References Cited

U.S. PATENT DOCUMENTS

| | | |
|---|---|---|
| 6,334,778 B1 | 1/2002 | Brown |
| 6,349,231 B1 | 2/2002 | Musha |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,425,764 B1 | 7/2002 | Lamson |
| 6,434,419 B1 | 8/2002 | Gevins et al. |
| 6,453,194 B1 | 9/2002 | Hill |
| 6,481,013 B1 | 11/2002 | Dinwiddie et al. |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,574,513 B1 | 6/2003 | Collura et al. |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,606,102 B1 | 8/2003 | Odom |
| 6,606,519 B2 | 8/2003 | Powell |
| 6,609,024 B1 | 8/2003 | Ryu et al. |
| 6,623,428 B2 | 9/2003 | Miller et al. |
| 6,626,676 B2 | 9/2003 | Freer |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,656,116 B2 | 12/2003 | Kim et al. |
| 6,662,052 B1 | 12/2003 | Sarwal et al. |
| 6,665,560 B2 | 12/2003 | Becker et al. |
| 6,678,866 B1 | 1/2004 | Sugimoto et al. |
| 6,688,890 B2 | 2/2004 | von Buegner |
| 6,699,188 B2 | 3/2004 | Wessel |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopinathan et al. |
| 6,788,882 B1 | 9/2004 | Geer et al. |
| 6,792,304 B1 | 9/2004 | Silberstein |
| 6,839,682 B1 | 1/2005 | Blume et al. |
| 6,842,877 B2 | 1/2005 | Robarts et al. |
| 6,904,408 B1 | 6/2005 | McCarthy et al. |
| 6,915,148 B2 | 7/2005 | Finneran et al. |
| 6,950,698 B2 | 9/2005 | Sarkela et al. |
| 6,958,710 B2 | 10/2005 | Zhang et al. |
| 6,961,601 B2 | 11/2005 | Matthews et al. |
| 6,973,342 B1 | 12/2005 | Swanson |
| 6,978,115 B2 | 12/2005 | Whitehurst et al. |
| 6,993,380 B1 | 1/2006 | Modarres |
| 7,035,685 B2 | 4/2006 | Ryu et al. |
| 7,050,753 B2 | 5/2006 | Knutson |
| 7,113,916 B1 | 9/2006 | Hill |
| 7,120,880 B1 | 10/2006 | Dryer et al. |
| 7,127,283 B2 | 10/2006 | Kageyama |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,173,437 B2 | 2/2007 | Hervieux et al. |
| 7,177,675 B2 | 2/2007 | Suffin et al. |
| 7,194,186 B1 | 3/2007 | Strub et al. |
| 7,222,071 B2 | 5/2007 | Neuhauser et al. |
| 7,272,982 B2 | 9/2007 | Neuhauser et al. |
| 7,286,871 B2 | 10/2007 | Cohen |
| 7,340,060 B2 | 3/2008 | Tomkins et al. |
| D565,735 S | 4/2008 | Washbon |
| 7,359,744 B2 | 4/2008 | Lee et al. |
| 7,383,728 B2 | 6/2008 | Noble et al. |
| 7,391,835 B1 | 6/2008 | Gross et al. |
| 7,408,460 B2 | 8/2008 | Crystal et al. |
| 7,420,464 B2 | 9/2008 | Fitzgerald et al. |
| 7,440,789 B2 | 10/2008 | Hannula et al. |
| 7,443,292 B2 | 10/2008 | Jensen et al. |
| 7,443,693 B2 | 10/2008 | Arnold et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,978 B2 | 12/2008 | John et al. |
| 7,471,987 B2 | 12/2008 | Crystal et al. |
| 7,483,835 B2 | 1/2009 | Neuhauser et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,627,880 B2 | 12/2009 | Itakura |
| 7,636,456 B2 | 12/2009 | Collins et al. |
| 7,650,793 B2 | 1/2010 | Jensen et al. |
| 7,672,717 B1 | 3/2010 | Zikov et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,715,894 B2 | 5/2010 | Dunseath et al. |
| 7,716,697 B2 | 5/2010 | Morikawa et al. |
| 7,720,351 B2 | 5/2010 | Levitan |
| 7,729,755 B2 | 6/2010 | Laken |
| 7,739,140 B2 | 6/2010 | Vinson et al. |
| 7,742,623 B1 | 6/2010 | Moon et al. |
| 7,751,878 B1 | 7/2010 | Merkle et al. |
| 7,805,009 B2 | 9/2010 | Everett et al. |
| 7,809,420 B2 | 10/2010 | Hannula et al. |
| 7,840,248 B2 | 11/2010 | Fuchs et al. |
| 7,840,250 B2 | 11/2010 | Tucker |
| 7,853,122 B2 | 12/2010 | Miura et al. |
| 7,865,394 B1 | 1/2011 | Calloway et al. |
| 7,892,764 B2 | 2/2011 | Xiong et al. |
| 7,908,133 B2 | 3/2011 | Neuhauser |
| 7,917,366 B1 | 3/2011 | Levanon et al. |
| 7,942,816 B2 | 5/2011 | Satoh et al. |
| 7,946,974 B2 | 5/2011 | Lordereau |
| 7,962,315 B2 | 6/2011 | Jensen et al. |
| 7,988,557 B2 | 8/2011 | Soderlund |
| 8,014,847 B2 | 9/2011 | Shastri et al. |
| 8,027,518 B2 | 9/2011 | Baker et al. |
| 8,055,722 B2 | 11/2011 | Hille |
| 8,069,125 B2 | 11/2011 | Jung et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,103,328 B2 | 1/2012 | Turner et al. |
| 8,112,141 B2 | 2/2012 | Wilson et al. |
| 8,135,606 B2 | 3/2012 | Dupree |
| 8,151,298 B2 | 4/2012 | Begeja et al. |
| 8,165,916 B2 | 4/2012 | Hoffberg et al. |
| 8,179,604 B1 | 5/2012 | Prada Gomez et al. |
| 8,209,224 B2 | 6/2012 | Pradeep et al. |
| 8,229,469 B2 | 7/2012 | Zhang et al. |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,290,563 B2 | 10/2012 | Jin et al. |
| 8,300,526 B2 | 10/2012 | Saito et al. |
| 8,326,396 B2 | 12/2012 | Picht et al. |
| 8,327,395 B2 | 12/2012 | Lee et al. |
| 8,332,883 B2 | 12/2012 | Lee et al. |
| 8,335,715 B2 | 12/2012 | Pradeep et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,442,429 B2 | 5/2013 | Hawit |
| 8,463,354 B2 | 6/2013 | Fadem |
| 8,467,133 B2 | 6/2013 | Miller |
| 8,473,345 B2 | 6/2013 | Pradeep et al. |
| 8,477,425 B2 | 7/2013 | Border et al. |
| 8,484,081 B2 | 7/2013 | Pradeep et al. |
| 8,494,610 B2 | 7/2013 | Pradeep et al. |

(56) References Cited

U.S. PATENT DOCUMENTS

| | | |
|---|---|---|
| 8,494,905 B2 | 7/2013 | Pradeep et al. |
| 8,533,042 B2 | 9/2013 | Pradeep et al. |
| 8,548,554 B2 | 10/2013 | Popescu et al. |
| 8,548,852 B2 | 10/2013 | Pradeep et al. |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 2001/0016874 A1 | 8/2001 | Ono et al. |
| 2001/0020236 A1 | 9/2001 | Cannon |
| 2001/0029468 A1 | 10/2001 | Yamaguchi et al. |
| 2001/0056225 A1 | 12/2001 | DeVito |
| 2002/0029005 A1 | 3/2002 | Levendowski et al. |
| 2002/0065826 A1 | 5/2002 | Bell et al. |
| 2002/0072952 A1 | 6/2002 | Hamzey et al. |
| 2002/0077534 A1 | 6/2002 | DuRousseau |
| 2002/0107454 A1 | 8/2002 | Collura et al. |
| 2002/0143627 A1 | 10/2002 | Barsade et al. |
| 2002/0154833 A1 | 10/2002 | Koch et al. |
| 2002/0155878 A1 | 10/2002 | Lert, Jr. et al. |
| 2002/0156842 A1 | 10/2002 | Signes et al. |
| 2002/0182574 A1 | 12/2002 | Freer |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0003433 A1 | 1/2003 | Carpenter et al. |
| 2003/0013981 A1 | 1/2003 | Gevins et al. |
| 2003/0036955 A1 | 2/2003 | Tanaka et al. |
| 2003/0055355 A1 | 3/2003 | Vieritio-Oja |
| 2003/0059750 A1 | 3/2003 | Bindler et al. |
| 2003/0063780 A1 | 4/2003 | Gutta et al. |
| 2003/0066071 A1 | 4/2003 | Gutta et al. |
| 2003/0067486 A1 | 4/2003 | Lee et al. |
| 2003/0073921 A1 | 4/2003 | Sohmer et al. |
| 2003/0076369 A1 | 4/2003 | Resner |
| 2003/0081834 A1 | 5/2003 | Philomin et al. |
| 2003/0093784 A1 | 5/2003 | Dimitrova et al. |
| 2003/0100998 A2 | 5/2003 | Brunner et al. |
| 2003/0104865 A1 | 6/2003 | Itkis et al. |
| 2003/0126593 A1 | 7/2003 | Mault |
| 2003/0153841 A1 | 8/2003 | Kilborn et al. |
| 2003/0165270 A1 | 9/2003 | Endrikhovski et al. |
| 2003/0177488 A1 | 9/2003 | Smith et al. |
| 2003/0233278 A1 | 12/2003 | Marshall |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0018476 A1 | 1/2004 | Ladue |
| 2004/0039268 A1 | 2/2004 | Barbour et al. |
| 2004/0044382 A1 | 3/2004 | Ibrahim |
| 2004/0072133 A1 | 4/2004 | Kullock et al. |
| 2004/0073129 A1 | 4/2004 | Caldwell et al. |
| 2004/0077934 A1 | 4/2004 | Massad |
| 2004/0088289 A1 | 5/2004 | Xu et al. |
| 2004/0092809 A1 | 5/2004 | DeCharms |
| 2004/0098298 A1 | 5/2004 | Yin |
| 2004/0111033 A1 | 6/2004 | Oung et al. |
| 2004/0138580 A1 | 7/2004 | Frei et al. |
| 2004/0138581 A1 | 7/2004 | Frei et al. |
| 2004/0161730 A1 | 8/2004 | Urman |
| 2004/0187167 A1 | 9/2004 | Maguire et al. |
| 2004/0193068 A1 | 9/2004 | Burton et al. |
| 2004/0208496 A1 | 10/2004 | Pilu |
| 2004/0210159 A1 | 10/2004 | Kibar |
| 2004/0220483 A1 | 11/2004 | Yeo et al. |
| 2004/0236623 A1 | 11/2004 | Gopalakrishnan |
| 2004/0267141 A1 | 12/2004 | Amano et al. |
| 2005/0010087 A1 | 1/2005 | Banet et al. |
| 2005/0010116 A1 | 1/2005 | Korhonen et al. |
| 2005/0010475 A1 | 1/2005 | Perkowski et al. |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 | 3/2005 | Martins |
| 2005/0076359 A1 | 4/2005 | Pierson et al. |
| 2005/0079474 A1 | 4/2005 | Lowe |
| 2005/0096311 A1 | 5/2005 | Suffin et al. |
| 2005/0097594 A1 | 5/2005 | O'Donnell et al. |
| 2005/0107716 A1 | 5/2005 | Eaton et al. |
| 2005/0113656 A1 | 5/2005 | Chance |
| 2005/0120372 A1 | 6/2005 | Itakura |
| 2005/0143629 A1 | 6/2005 | Farwell |
| 2005/0154290 A1 | 7/2005 | Langleben |
| 2005/0165285 A1 | 7/2005 | Iliff |
| 2005/0172311 A1 | 8/2005 | Hjelt et al. |
| 2005/0177058 A1 | 8/2005 | Sobell |
| 2005/0197556 A1 | 9/2005 | Stoler |
| 2005/0197590 A1 | 9/2005 | Osorio et al. |
| 2005/0203798 A1 | 9/2005 | Jensen et al. |
| 2005/0215916 A1 | 9/2005 | Fadem et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0010470 A1 | 1/2006 | Kurosaki et al. |
| 2006/0035707 A1 | 2/2006 | Nguyen et al. |
| 2006/0053110 A1 | 3/2006 | McDonald et al. |
| 2006/0064037 A1 | 3/2006 | Shalon et al. |
| 2006/0093998 A1 | 5/2006 | Vertegaal |
| 2006/0094970 A1 | 5/2006 | Drew |
| 2006/0111044 A1 | 5/2006 | Keller |
| 2006/0111621 A1 | 5/2006 | Coppi et al. |
| 2006/0111644 A1 | 5/2006 | Guttag et al. |
| 2006/0129458 A1 | 6/2006 | Maggio |
| 2006/0143647 A1 | 6/2006 | Bill |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0189900 A1 | 8/2006 | Flaherty |
| 2006/0217598 A1 | 9/2006 | Miyajima et al. |
| 2006/0256133 A1 | 11/2006 | Rosenberg |
| 2006/0257834 A1 | 11/2006 | Lee et al. |
| 2006/0258926 A1 | 11/2006 | Ali et al. |
| 2006/0259360 A1 | 11/2006 | Flinn et al. |
| 2006/0265022 A1 | 11/2006 | John et al. |
| 2006/0277102 A1 | 12/2006 | Agliozzo |
| 2006/0293608 A1 | 12/2006 | Rothman et al. |
| 2006/0293921 A1 | 12/2006 | McCarthy et al. |
| 2007/0031798 A1 | 2/2007 | Gottfried |
| 2007/0048707 A1 | 3/2007 | Caamano et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066914 A1 | 3/2007 | Le et al. |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0116037 A1 | 5/2007 | Moore |
| 2007/0135727 A1 | 6/2007 | Virtanen et al. |
| 2007/0135728 A1 | 6/2007 | Snyder et al. |
| 2007/0168461 A1 | 7/2007 | Moore |
| 2007/0173733 A1 | 7/2007 | Le et al. |
| 2007/0173886 A1* | 7/2007 | Rousso .................. A61H 7/001 606/203 |
| 2007/0179396 A1 | 8/2007 | Le et al. |
| 2007/0184420 A1 | 8/2007 | Mathan et al. |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1* | 10/2007 | Delic .................. A61B 5/6803 600/383 |
| 2007/0249952 A1 | 10/2007 | Rubin et al. |

(56) References Cited

U.S. PATENT DOCUMENTS

| | | |
|---|---|---|
| 2007/0250846 A1 | 10/2007 | Swix et al. |
| 2007/0255127 A1 | 11/2007 | Mintz et al. |
| 2007/0265507 A1 | 11/2007 | de Lemos |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0039737 A1 | 2/2008 | Breiter et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0082020 A1 | 4/2008 | Collura |
| 2008/0086356 A1 | 4/2008 | Glassman et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0127978 A1 | 6/2008 | Rubin et al. |
| 2008/0139949 A1 | 6/2008 | Caldarone et al. |
| 2008/0144882 A1 | 6/2008 | Leinbach et al. |
| 2008/0147488 A1 | 6/2008 | Tunick et al. |
| 2008/0152300 A1 | 6/2008 | Knee et al. |
| 2008/0159365 A1 | 7/2008 | Dubocanin et al. |
| 2008/0162182 A1 | 7/2008 | Cazares et al. |
| 2008/0177197 A1 | 7/2008 | Lee et al. |
| 2008/0201731 A1 | 8/2008 | Howcraft |
| 2008/0204273 A1 | 8/2008 | Crystal et al. |
| 2008/0208072 A1 | 8/2008 | Fadem et al. |
| 2008/0211768 A1 | 9/2008 | Breen et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2008/0306398 A1 | 12/2008 | Uchiyama et al. |
| 2008/0312523 A1 | 12/2008 | Dunseath |
| 2009/0024017 A1 | 1/2009 | Ruffini et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030298 A1 | 1/2009 | Matthews et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1 | 4/2009 | Lee et al. |
| 2009/0088619 A1* | 4/2009 | Turner ............... A61B 5/291 600/383 |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0105576 A1 | 4/2009 | Do et al. |
| 2009/0108205 A1 | 4/2009 | Duffy et al. |
| 2009/0112077 A1 | 4/2009 | Nguyen et al. |
| 2009/0119154 A1 | 5/2009 | Jung et al. |
| 2009/0131764 A1 | 5/2009 | Lee et al. |
| 2009/0133047 A1 | 5/2009 | Lee et al. |
| 2009/0150919 A1 | 6/2009 | Lee et al. |
| 2009/0156925 A1 | 6/2009 | Jin et al. |
| 2009/0158308 A1 | 6/2009 | Weitzenfeld et al. |
| 2009/0163777 A1 | 6/2009 | Jung |
| 2009/0195392 A1 | 8/2009 | Zalewski |
| 2009/0214060 A1 | 8/2009 | Chuang et al. |
| 2009/0222330 A1 | 9/2009 | Leinbach |
| 2009/0248484 A1 | 10/2009 | Surendran et al. |
| 2009/0248496 A1 | 10/2009 | Hueter et al. |
| 2009/0253996 A1 | 10/2009 | Lee et al. |
| 2009/0259137 A1 | 10/2009 | Delic et al. |
| 2009/0271122 A1 | 10/2009 | Hyde et al. |
| 2009/0292587 A1 | 11/2009 | Fitzgerald |
| 2009/0295738 A1 | 12/2009 | Chiang |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0036275 A1 | 2/2010 | Alkire |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0075532 A1 | 3/2010 | Copp-Howland et al. |
| 2010/0076333 A9 | 3/2010 | Burton et al. |
| 2010/0125190 A1 | 5/2010 | Fadem |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250458 A1 | 9/2010 | Ho |
| 2010/0257052 A1 | 10/2010 | Zito et al. |
| 2010/0268540 A1 | 10/2010 | Arshi et al. |
| 2010/0268573 A1 | 10/2010 | Jain et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0306120 A1 | 12/2010 | Ciptawilangga |
| 2010/0317988 A1 | 12/2010 | Terada et al. |
| 2010/0325660 A1 | 12/2010 | Holden |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0040202 A1 | 2/2011 | Luo et al. |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0054288 A1 | 3/2011 | Besio |
| 2011/0059422 A1 | 3/2011 | Masaoka |
| 2011/0085700 A1 | 4/2011 | Lee |

(56) References Cited

U.S. PATENT DOCUMENTS

| | | |
|---|---|---|
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0131274 A1 | 6/2011 | Hille |
| 2011/0144519 A1 | 6/2011 | Causevic |
| 2011/0151728 A1 | 6/2011 | Astola |
| 2011/0153391 A1 | 6/2011 | Tenbrock |
| 2011/0161163 A1 | 6/2011 | Carlson et al. |
| 2011/0161790 A1 | 6/2011 | Junior et al. |
| 2011/0191142 A1 | 8/2011 | Huang |
| 2011/0208515 A1 | 8/2011 | Neuhauser |
| 2011/0224569 A1 | 9/2011 | Isenhart et al. |
| 2011/0224570 A1 | 9/2011 | Causevic |
| 2011/0237923 A1 | 9/2011 | Picht et al. |
| 2011/0237971 A1 | 9/2011 | Pradeep et al. |
| 2011/0248729 A2 | 10/2011 | Mueller et al. |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0298706 A1 | 12/2011 | Mann |
| 2011/0301431 A1 | 12/2011 | Greicius et al. |
| 2011/0319975 A1 | 12/2011 | Ho et al. |
| 2012/0003862 A1 | 1/2012 | Newman et al. |
| 2012/0004899 A1 | 1/2012 | Arshi |
| 2012/0022391 A1 | 1/2012 | Leuthardt |
| 2012/0036004 A1 | 2/2012 | Pradeep et al. |
| 2012/0036005 A1 | 2/2012 | Pradeep et al. |
| 2012/0054018 A1 | 3/2012 | Pradeep et al. |
| 2012/0072289 A1 | 3/2012 | Pradeep et al. |
| 2012/0096363 A1 | 4/2012 | Barnes et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0143020 A1 | 6/2012 | Bordoley et al. |
| 2012/0173701 A1 | 7/2012 | Tenbrock |
| 2012/0179019 A1* | 7/2012 | Fadem .............. A61B 5/291 600/383 |
| 2012/0190959 A1 | 7/2012 | Hayakawa et al. |
| 2012/0190998 A1 | 7/2012 | Armitstead et al. |
| 2012/0203363 A1 | 8/2012 | McKenna et al. |
| 2012/0203559 A1 | 8/2012 | McKenna et al. |
| 2012/0239407 A1 | 9/2012 | Lynch et al. |
| 2012/0245978 A1 | 9/2012 | Jain et al. |
| 2012/0249797 A1 | 10/2012 | Haddick et al. |
| 2013/0024272 A1 | 1/2013 | Pradeep et al. |
| 2013/0060125 A1 | 3/2013 | Zeman |
| 2013/0066183 A1 | 3/2013 | Jin et al. |
| 2013/0085363 A1* | 4/2013 | Wada .............. A61B 5/291 600/383 |
| 2013/0104288 A1 | 5/2013 | Schlottau et al. |
| 2013/0166373 A1 | 6/2013 | Pradeep et al. |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0253300 A1 | 9/2013 | Fadem |
| 2013/0303874 A1 | 11/2013 | Diamond et al. |
| 2013/0311132 A1 | 11/2013 | Tobita |
| 2013/0332259 A1 | 12/2013 | Pradeep et al. |
| 2016/0007918 A1 | 1/2016 | Badower et al. |

FOREIGN PATENT DOCUMENTS

| | | |
|---|---|---|
| DE | 102010005551 | 7/2011 |
| EP | 1052582 | 11/2000 |
| EP | 1389012 | 2/2004 |
| EP | 1607842 | 12/2005 |
| EP | 1815788 | 8/2007 |
| EP | 2449961 | 5/2012 |
| FR | 2627975 | 9/1989 |
| GB | 1374658 | 11/1974 |
| GB | 2221759 | 2/1990 |
| JP | 02243131 | 9/1990 |
| JP | 05-293172 | 11/1993 |
| JP | 07-329657 | 12/1995 |
| JP | 2002-000577 | 1/2002 |
| JP | 2002-056500 | 2/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2003-522580 | 7/2003 |
| JP | 2005-160805 | 12/2003 |
| JP | 2004-527843 | 9/2004 |
| JP | 2005-084770 | 3/2005 |
| JP | 2005261076 | 9/2005 |
| JP | 2006-305334 | 11/2006 |
| JP | 2006-323547 | 11/2006 |
| JP | 2011-104338 | 6/2011 |
| JP | 2013240485 | 12/2013 |
| KR | 10-2000-0072489 | 12/2000 |
| KR | 10-2001-0104579 | 11/2001 |
| KR | 10-2012-0129870 | 11/2012 |
| WO | 94-12099 | 6/1994 |
| WO | 95-018565 | 7/1995 |
| WO | 97-017774 | 5/1997 |
| WO | 97-040745 | 11/1997 |
| WO | 97-041673 | 11/1997 |
| WO | 00/17824 | 3/2000 |
| WO | 01/97070 | 12/2001 |
| WO | 02084624 | 10/2002 |
| WO | 02-100241 | 12/2002 |
| WO | 02-100267 | 12/2002 |
| WO | 02-102238 | 12/2002 |
| WO | 2004-034881 | 4/2004 |
| WO | 2004-049225 | 6/2004 |
| WO | 2004/100765 | 11/2004 |
| WO | 2006/005767 | 1/2006 |
| WO | 2007/019584 | 2/2007 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-137579 | 11/2008 |
| WO | 2008-137581 | 11/2008 |
| WO | 2008-141340 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |
| WO | 2012-036639 | 3/2012 |

OTHER PUBLICATIONS

Adamic et al., "The Political Blogosphere and the 2004 U.S. election: Divided They Blog," Proceedings WWW—2005 2nd Annual Workshop on the Weblogging Ecosystem, 2005, Chiba, Japan, 16 pages.

Adar et al., "Implicit Structure and the Dynamics of Blogspace," Proceedings WWW—2004 Workshop on the Weblogging Ecosystem, 2004, New York, NY, 8 pages.

Akam, et al., "Oscillations and Filtering Networks Support Flexible Routing of Information," Neuron, vol. 67, pp. 308-320, Elsevier, Jul. 29, 2010, 13 pages.

Aliod et al., "A Real World Implementation of Answer Extraction," Department of Computer Science, University of Zurich, Winterthurerstr. 190, CH-8057 Zurich, Switzerland, 1998, 6 pages.

Allen et al., "A Method of Removing Imaging Artifact from Continuous EEG Recorded during Functional MRI," Neuroimage, vol. 12, 230-239, Aug. 2000, 12 pages.

Ambler, "Salience and Choice: Neural Correlates of Shopping Decisions," Psychology & Marketing, vol. 21, No. 4, p. 247-261,

(56) References Cited

OTHER PUBLICATIONS

Wiley Periodicals, Inc., doi: 10.1002/mar20004, Apr. 2004, 16 pages.
Ambler et al., "Ads on the Brain; A Neuro-Imaging Comparison of Cognitive and Affective Advertising Stimuli," London Business School, Centre for Marketing Working Paper, No. 00-902, Mar. 2000, 23 pages.
Badre, et al. "Frontal Cortex and the Discovery of Abstract Action Rules," Neuron, vol. 66, pp. 315-326, Elsevier, Apr. 29, 2010, 12 pages.
Bagozzi et al., "The Role of Emotions in Marketing," Journal of the Academy of Marketing Science, vol. 27, No. 2, pp. 184-206, Academy of Marketing Science, 1999, 23 pages.
Barcelo, et al., "Prefrontal modulation of visual processing in humans," Nature Neuroscience, vol. 3, No. 4, Nature America, http//neurosci.nature.com, Apr. 2000, 5 pages.
Barreto et al., "Physiologic Instrumentation for Real-time Monitoring of Affective State of Computer Users," WSEAS International Conference on Instrumentation, Measurement, Control, Circuits and Systems (IMCCAS), 2004, 6 pages.
Beaver, John D., et al., "Individual Differences in Reward Drive Predict Neural Responses to Images of Food", J. of Neuroscience, May 10, 2006, 5160-5166, 7 pages.
Belch et al., "Psychophysiological and Cognitive Responses to Sex in Advertising," Advances in Consumer Research, vol. 9, pp. 424-427, 1982, 6 pages.
Bimler et al., "Categorical perception of facial expressions of emotion: Evidence from multidimensional scaling," Cognition and Emotion, vol. 15(5), pp. 633-658 Sep. 2001, 26 pages.
Bishop, Mike, "ARROW Question/Answering Systems," Language Computer Corporation, 1999, 3 pages.
Bizrate, archived version of www.bizrate.com, [http://web.archive.org/web/*/http://www.bizrate.com], retrieved Oct. 29, 2004, 22 pages.
Blakeslee, "If You Have a 'Buy Button' in Your Brain, What Pushes It?" The New York Times, www.nytimes.com, Oct. 19, 2004, 3 pages.
Blum, "Empirical Support for Winnow and Weighted-Majority Algorithms: Results on a Calendar Scheduling Domain," in Machine Learning, vol. 26, Kluwer Academic Publishers, Boston, USA, 1997, 19 pages.
Bournellis, Cynthia, "Tracking the hits on Web Sites," Communications International: vol. 22, Issue 9, London, Sep. 1995, 3 pages.
Braeutigam, "Neuroeconomics—From neural systems to economic behavior," Brain Research Bulletin, vol. 67, pp. 355-360, Elsevier, 2005, 6 pages.
Buschman, et al., "Top-Down versus Bottom-Up Control of Attention in the Prefrontal and Posterior Parietal Cortices," Science, vol. 315, www.sciencemag.org/cgi/content/full/315/5820/1860, American Association for the Advancement of Science, 2007, 4 pages.
Buschman, et al., "Serial, Covert Shifts of Attention during Visual Search Are Reflected by the Frontal Eye Fields and Correlated with Population Oscillations," Neuron, vol. 63, pp. 386-396, Elsevier, Aug. 13, 2009, 11 pages.
Canolty, et al., "High Gamma Power is Phase-Locked to Theta Oscillations in Human Neocortex," Science, vol. 313, www.sciencemag.org, Sep. 15, 2006, 3 pages.
Chaum et al., "A Secure and Privacy-Protecting Protocol for Transmitting Personal Information Between Organizations," A.M. Odlyzko (Ed.): Advances in Cryptology, CRYPTO '86, LNCS 263, 1987, 51 pages.
Chaum, David L., "Untraceable Electronic Mail, Return Addresses and Digital Pseudonyms," Communication of the ACM, vol. 24, No. 2, 1981, 5 pages.
Carter, "Mapping the Mind," 1998, University of California Press, Berkeley, 3 pages.
Cheng, et al. "Gender Differences in the Mu Rhythm of the Human Mirror-Neuron System," PLos ONE, vol. 3, Issue 5, www.plosone.org, May 2008, 7 pages.
Clarke, Adam R. et al., "EEG Analysis of Children with Attention-Deficit/Hyperactivity Disorder and Comorbid Reading Disabilities," Journal of Learning Disabilities, vol. 35, No. 3, May-Jun. 2002, 10 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, Mar. 28, 2007, 8 pages.
Clifford, "Billboards That Look Back," The New York Times, NYTimes.com, available at http://www.nytimes.com/2008/05/31/business/media/31billboard.html, May 31, 2008, 4 pages.
Coan et al., "Voluntary Facial Expression and Hemispheric Asymmetry Over the Frontal Cortex," Psycophysiology (Nov. 2001), 912-924, 14 pages.
Cohen, William W., "Data Integration Using Similarity Joins and a Word-Based Information Representation Language," ACM Transactions on Information Systems, vol. 18, No. 3, Jul. 2000, 34 pages.
Cohn et al., "Active Learning with Statistical Models," Journal of Artificial Intelligence Research 4, AI Access Foundation and Morgan Kaufmann Publishers, USA, 1996, 17 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, Dec. 1996, 28 pages.
Dagan et al., "Mistake-Driven Learning in Text Categorization," in EMNLP '97, $2^{nd}$ Conference on Empirical Methods in Natural Language Processing, 1997, 9 pages.
Davidson, et al., "The functional neuroanatomy of emotion and affective style," Trends in Cognitive Sciences, vol. 3, No. 1, Jan. 1999, 11 pages.
De Gelder et al., "Categorical Perception of Facial Expressions: Categories and their Internal Structure," Cognition and Emotion, vol. 11(1), pp. 1-23 1997, 23 pages.
D'Esposito, "From cognitive to neural models of working memory," Phil. Trans. R. Soc. B, doi: 10.1098/rstb.2007.2086, Mar. 30, 2007, 12 pages.
Delahaye group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.
Desmet, "Measuring Emotions: Development and Application of an Instrument to Measure Emotional Responses to Products," to be published in Funology: From Usability to Enjoyment, pp. 111-123, Kluwer Academic Publishers, (Blythe et al., eds., 2004), 13 pages.
Dialogic, www.dialogic.com, [http://web.archive.org/web/*/http://www.dialogic.com], retrieved Dec. 2, 2003, 34 pages.
Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.
Dillon et al., "Marketing research in a Marketing Environment," Times Mirror/Mosby College, USA, 1987, 5 pages.
Duchowski, "A breadth-first survey of eye-tracking Applications," Behavior Research Methods, Instruments, and Computers (Nov. 2002), 455-470, 16 pages.
Edgar, et al., "Digital Filters in ERP Research," in Event-Related Potentials: A Methods Handbook pp. 85-113, (Todd C. Handy, ed., 2005), 15 pages.
EEG Protocols, "Protocols for EEG Recording," retrieved from the Internet on Aug. 23, 2011, http://www.q-metrx.com/EEGrecordingProtocols.pdf, Nov. 13, 2007, 3 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
El-Bab et al., "Congnative event related potentials during a learning task," Doctoral Dissertation, Faculty of Medicine, University of Southamption, 2001, 25 pages.
Engel et al., "Dynamic Predictions: Oscillations and Synchrony in Top-down Processing," Nature Reviews: Neuroscience, vol. 2, pp. 704-716, Macmillian Magazines Ltd., Oct. 2001, 13 pages.

(56) References Cited

OTHER PUBLICATIONS

Ewatch, eWatch's archived web site retrieved from [URL: http://web.archive.org/web/19980522190526/wwww.ewatch.com] on Sep. 8, 2004, archived May 22, 1998, 50 pages.
Farber, Dave, "IP: eWatch and Cybersleuth," retrieved from [URL: http://www.interesting-people.org/archives/interesting-people/200006/msg00090.html] Jun. 29, 2000, 4 pages.
Filler, "MR Neurography and Diffusion Tensor Imaging: Origins, History & Clinical Impact of the first 50,000 Cases With an Assortment of Efficacy and Utility in a Prospective 5,000 Patent Study Group," Institute for Nerve Medicine, Nov. 7, 2008, 56 pages.
Flinker et al, "Sub-centimeter language organization in the human temporal lobe," Brain and Language, Elsevier Inc., (2010), doi.org/10.1016/j.bandl.2010.09.009, 7 pages.
Fogelson, et al., "Prefrontal cortex is critical for contextual processing: evidence from brain lesions," Brain: A Journal of Neurology, vol. 132, pp. 3002-3010, doi:10.1093/brain/awp230, Aug. 27, 2009, 9 pages.
Freund et al., "Selective Sampling Using the Query by Committee Algorithm," Machine Learning 28 Kluwer Academic Publishers, The Netherlands, 1997, 36 pages.
Friedman, et al., "Event-Related Potential (ERP) Studies of Memory Encoding and Retrieval: A Selective Review," Microscopy Research and Technique 51:6-26, Wiley-Less, Inc., 2000, 23 pages.
Fries, "A mechanism for cognitive dynamics: neuronal coherence," Trends in Cognitive Sciences, vol. 9, No. 10, pp. 474-480, Elsevier B.V. www.sciencedirect.com, Oct. 2005, 7 pages.
Fuster, "Cortex and Memory: Emergence of a New Paradigm," Journal of Cognitive Neuroscience, vol. 21, No. 11, pp. 2047-2072, Massachusetts Institute of Technology, Nov. 2009, 26 pages.
Gaillard, "Problems and Paradigms in ERP Research," Biological Psychology, Elsevier Science Publisher B.V., 1988, 10 pages.
Gargiulo et al., "A Mobile EEG System With Dry Electrodes," (Nov. 2008), 4 pages.
Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, 2005, 11 pages.
Gevins et al., "High resolution EEG Mapping of Cortical Activation Related to Working Memory: Effects of Task Difficulty, Type of Processing, and Practice" Cereb Cortex. 7, 1997, 12 pages.
Glance et al., "Analyzing online disussion for marketing intelligence," Proceedings WWW—2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug. 21-24, 2005, 10 pages.
Grefensette et al., "Validating the Coverage of Lexical Resources for Affect Analysis and Automatically Classifying New Words along Semantic Axes," Chapter X, 3, Mar. 2004, 16 pages.
Griss et al., "Characterization of micromachined spiked biopotential electrodes", Biomedical Engineering, IEEE Transactions Jun. 2002, 8 pages.
Haq, "This Is Your Brain on Advertising," BusinessWeek, Market Research, Oct. 8, 2007, 4 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Depattment of Computer Science and Engineering at Southern Methodist Universtity, 2000, 7 pages.
Harabagiu, Sanda M., "Mining Textual Answers with Knowledge-Based Indicators," Department of Computer Science and Engineering at Southern Methodist University, 2000, 5 pages.
Harland et al., "Remote detection of human electroencephalograms using ultrahigh input impedance electrical potential sensors," Applied Physics Letters., vol. 81, No. 17, Oct. 21, 2002, 3 pages.
Harmony et al., "Specific EEG frequencies signal general common congnative processes as well as specific tasks processes in man," International Journal of Psycophysiology, 53, 2004, 10 pages.
Hartikainen et al., Manuscript Draft of "Emotionally arousing stimuli compete with attention to left hemispace," NeuroReport, Sep. 8, 2007, 26 pages.
Hazlett et al., "Emotional Response to Television Commercials: Facial EMG vs. Self-Report," Journal of Advertising Research, Apr. 1999, 17 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Herrmann et al., "Mechanisms of human attention: event-related potentials and oscillations," Neuroscience and Biobehavioral Reviews, pp. 465-476, Elsevier Science Ltd., www.elsvevier.com/locate/neubiorev, 2001, 12 pages.
Hopf et al., "Neural Sources of Focused Attention in Visual Search," Cerebral Cortex, 10:1233-1241, Oxford University Press, Dec. 2000, 9 pages.
Housley et al., "Internet X.509 Public Key Infrastructure Certificate and CRL Profile," Network Working Group Request for Comments: 2459, Jan. 1999, 121 pages.
Hughes, et al., "Conventional and Quantatative Electroencephalography in Psychiatry," Journal of Neuropsychiatry and Clinical Neurosciences, vol. 11(2), 1999, 19 pages.
Joachims, "Text Categorization with Support Vector Machines: Learning with Many Relevant Features," in Machine Learning: ECML-98, Tenth European Conference on Machine Learning, 1998, 7 pages.
Jung et al., "Analysis and Visualization of Single-Trial Event-Related Potentials," Human Brain Mapping vol. 14, 166-185 2001, 20 pages.
Kahn et al., "Categorizing Web Documents using Competitive Learning: An Ingrediant of a Personal Adaptive Agent," IEEE 1997, 4 pages.
Katz, "From Sentence Processing to Information Access on the World Wide Web," MIT Artificial Intelligence Laboratory, Feb. 27, 1997, 20 pages.
Kay et al., "Identifying natural images from human brain activity," Nature, vol. 452, pp. 352-356, Nature Publishing Group, Mar. 20, 2008, 5 pages.
Keren et al., "Saccadic spike potentials in gamma-band EEG: Characterization, detection and suppression," NeuroImage, http://dx.doi:10.1016/j.neuroimage.2009.10.057, Oct. 2009, 16 pages.
Kishiyama, et al., "Novelty Enhancements in Memory Are Dependent on Lateral Prefrontal Cortex," The Journal of Neuroscience, pp. 8114-8118, Society for Neuroscience Jun. 24, 2009, 5 pages.
Kishiyama, et al., "Socioeconomic Disparities Affect Prefrontal Function in Children," Journal of Cognitive Neuroscience pp. 1106-1115, Massachusetts Institute of Technology, 2008, 10 pages.
Kleppner, "Advertising Procedure," 6th edition, 1977, Prentice-Hall, Inc., Englewood Cliffs, NJ, 3 pages.
Klimesch, "EEG alpha and theta oscillations reflect cognitive and memory performance a review and analysis," Brain Research Reviews, vol. 29, 169-195, 1999, 27 pages.
Klimesch, et al. "Episodic and semantic memory: an analysis in the EEG theta and alpha band," Electroencephalography Clinical Neurophysiology, 1994, 14 pages.
Kotler, "Marketing Management," PrenticeHall International Inc., Upper Saddle River, NJ, 1997, 10 pages.
Knight, "Contribution of human hippocampal region to novelty detection," Nature, vol. 383, www.nature.com, Sep. 19, 1996, 4 pages.
Knight, "Consciousness Unchained: Ethical Issues and the Vegetative and minimally Conscious State," The American Journal of Bioethics, 8:9, 1-2, http://dx.doi.org/10.1080/15265160802414524, Sep. 1, 2008), 3 pages.
Knight, et al., "Prefrontal cortex regulates inhibition and excitation in distributed neural networks," Acta Psychologica vol. 101, pp. 159-178, Elsevier 1999, 20 pages.

(56) References Cited

OTHER PUBLICATIONS

Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., 1984, 12 pages.
Krakow et al., "Methodology: EEG-correlated fMRI," Functional Imaging in the Epilepsies, Lippincott Williams & Wilkins, 2000, Advances in Neurology, vol. 83, 17 pages.
Krugman, "Brain Wave Measures of Media Involvement," Journal of Advertising Research vol. 11, Feb. 3-9, 1971, 7 pages.
Lachaux et al., "Measuring Phase Synchrony in Brain Signals," Human Brain Mapping 8, 1999, 194-208, 15 pages.
Lee et al., "What is 'neuromarketing'? A discussion and agenda for future research," International Journal of Psychophysiology, vol. 63, pp. 199-204, Elsevier 2006, 6 pages.
Lekakos, "Personalized Advertising Services Through Hybrid Recommendation Methods: The Case of Digital Interactive Television," Department of Informatics, Cyprus University, 2004, 11 pages.
Lenz et al., "Question answering with Textual CBR," Department of Computer Science, Humboldt University Berlin, D-10099 Berlin, 1998, 12 pages.
Lewis et al., "Market Researchers make Increasing use of Brain Imaging," ACNR, vol. 5, No. 3, pp. 36-37, Jul./Aug. 2005, 2 pages.
Littlestone, "Learning Quickly When Irrelevant Attributes Abound: A New Linear-threshold Algorithm," in Machine Learning, vol. 2, Kluwer Academic Publishers, Boston, MA, 1988, 34 pages.
Luck et al., "The speed of visual attention in schizophrenia: Electrophysiological and behavioral evidence," Schizophrenia Research, pp. 174-195, Elsevier B.V. www.sciencedirect.com, 2006, 22 pages.
Lui et al., "Marketing Strategies in Virtual Worlds," The Data Base for Advances in Information Systems, vol. 38, No. 4, pp. 77-80, Nov. 2007, 4 pages.
Makeig et al., "Mining event-related brain dynamics," TRENDS in Cognitive Sciences, vol. 8, No. 5, May 2004, www.sciencedirect.com, 7 pages.
Makeig et al., "Dynamic Brain Sources of Visual Evoked Responses," Science, vol. 295, www.sciencemag.org, Jan. 25, 2002, 5 pages.
Marlow, "Audience, structure and authority in the weblog community," International Communication Association Conference, MIT Media Laboratory, New Orleans, LA 2004, 9 pages.
The Mathworks, Inc., "MATLAB Data Analysis: Version 7," pp. 4-19, 2005, 3 pages.
McCallum et al., "Text Classification by Bootstrapping with the Keywords, EM and Shrinkage," Just Research and Carnegie Mellon University, Pittsburgh, PA, circa 1999, 7 pages.
McLachlan et al., "The EM Algorithm and Extensions," John Wiley & Sons, Inc., New York, NY, 1997, 302 pages.
Meriam-Webster Online Dictionary definition for "tangible," retrieved from [URL http://www.meriam-webster.com/dictionary/tangible] on Jan. 1, 2012, 1 page.
Meriam Webster Online Dictionary, Definition of Virtual Reality, retrieved from [URL: http://www.meriam-webster.com/dictionary/virtual%20reality] on Feb. 25, 2012, 2 pages.
Miltner, et al., "Coherence of gamma-band EEG activity as a basis for associative learning," Nature, vol. 397, www.nature.com, Feb. 4, 1999, 3 pages.
Mizuhara et al., A long range cortical network emerging with theta oscillation in mental task, Neuroreport 15 (8), 2004, 11 pages.
Moldovan et al., "LASSO: A Tool for Surfing the Answer Net," Department of Computer Science and Engineering at Southern Methodist University, 1999, 9 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
Nakashima et al., "Information Filtering for the Newspaper," IEEE 1997, 4 pages.
Nanno et al., "Automatic collection and monitoring of Japanese Weblogs," Proceedings WWW—2004 Workshop on the weblogging Ecosystem, 2004, New York, NY, 7 pages.
Netcurrent, NetCurrent's web site, http://web.archive.org/web/20000622024845/www.netcurrents.com, retrieved on Jan. 17, 2005, archived on Jun. 22, 2000 and Sep. 18, 2000, 17 pages.
Neurofocus—Neuroscientific Analysis for Audience Engagement, accessed on Jan. 8, 2010 at http://web.archive.org/web/20080621114525/www.neurofocus.com/BrandImage.htm, 2008, 2 pages.
Newell et al., "Categorical perception of familiar objects," Cognition, vol. 85, Issue 2, pp. 113-143 Sep. 2002, 31 pages.
Nielsen, "Neuroinformatics in Functional Neuroimaging," Informatics and Mathematical Modeling, Technical University of Denmark, Aug. 30, 2002, 241 pages.
Oberman et al., "EEG evidence for mirror neuron activity during the observation of human and robot actionsAug. 29, 2012 Toward an analysis of the human qualities of interactive robots," Neurocomputing 70, 2007 2194-2203, 10 pages.
Osborne, "Embedded Watermarking for image Verification in Telemedicine," Thesis submitted for the degree of Doctor of Philosophy, Electrical and Electronic Engineering, University of Adelaide, 2005, 219 pages.
Padgett et al., "Categorical Perception in Facial Emotion Classification," In Proceedings of the 18th Annual Conference of the Cognitive Science Society, pp. 249-253, 1996, 5 pages.
Page et al., "Cognitive Neuroscience, Marketing and Research," Congress 2006—Foresight—The Predictive Power of Research Conference Papers, ESOMAR Publications, Sep. 17, 2006, 25 pages.
Paller, et al., "Validating neural correlates of familiarity," TRENDS in Cognitive Sciences, vol. 11, No. 6, www.sciencedirect.com, May 2, 2007, 8 pages.
Palva et al., "Phase Synchrony Among Neuronal Oscillations in the Human Cortex," Journal of Neuroscience 25 2005, 3962-3972, 11 pages.
Pang et al., "Thumbs up? Sentiment Classification using Machine Learning Techniques," in Proceedings of EMNLP 2002, 8 pages.
Picton, et al., "Guidelines for using human event-related potentials to study cognition: Recording standards and publication criteria," Psychophysiology, pp. 127-152, Society for Psychophysiological Research, 2000, 26 pages.
Reguly, "Caveat Emptor Rules on the Internet," The Globe and Mail (Canada): Report on Business Column, Apr. 10, 1999, 2 pages.
Reinartz, "Customer Lifetime Value Analysis: An Integrated Empirical Framework for Measurement and Explanation," dissertation, University of Houston, Faculty of College of Business Administration, Apr. 1999, 68 pages.
Rizzolatti et al., "The Mirror-Neuron System," Annu. Rev. Neurosci., vol. 27, pp. 169-192, Mar. 5, 2004, 30 pages.
Rothschild et al., "Predicting Memory for Components of TV Commercials from EEG," Journal of Consumer Research (Mar. 1990), p. 472-478, 8 pages.
Ruchkin et al., "Modality-specific processing streams in verbal working memory: evidence from spatio-temporal patterns of brain activity," Cognitive Brain Research, vol. 6, pp. 95-113, Elsevier, 1997, 19 pages.
Rugg, et al., "Event-related potentials and recognition memory," TRENDS in Cognitive Sciences, vol. 11, No. 6, www.sciencedirect.com, May 3, 2007, 7 pages.
Rugg, et al., "The ERP and cognitive psychology: conceptual issues," Sep. 1996, 7 pages.
"User monitoring," Sapien Systems, available at http://web.archive.org/web/20030818043339/http:/www.sapiensystems.com/eyetracking.html, Aug. 18, 2003, 1 page.
Sammler et al., "Music and emotion: Electrophysiological correlates of the processing of pleasant and unpleasant music," Psychophysiology, vol. 44, Blackwell Publiching Inc., 2007, 12 pages.
Schmidt et al., "Frontal brain electrical activity (EEG) distinguishes valence and intensity of musical emotions," Cognition and Emotion, vol. 15 (4), Psychology Press Ltd, 2001, 14 pages.
Selden, "Machines that Read Minds," Science Digest, Oct. 1981, 9 pages.
Shandlen et al., "A Computational Analysis of the Relationship between Neuronal and Behavioral Responses to Visual Motion", The Journal of Neuroscience, (Feb. 15, 1996) 1486-1510, 25 pages.

(56) References Cited

OTHER PUBLICATIONS

Simon-Thomas et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology 2005, 12 pages.
Soderland et al., "Customer Satisfaction and Links to Customer Profitability: An Empirical Examination of the Association Between Attitudes and Behavior," SSE/EFI Working Paper Series in Business Administration, Jan. 1999, 22 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, May 18, 2008, 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, Mar. 2007, 5 pages.
Swick et al., "Contributions of Prefrontal Cortex to Recognition Memory: Electrophysiological and Behavioral Evidence," Neuropsychology, vol. 13, No. 2, pp. 155-170, American Psychological Association, Inc. 1999, 16 pages.
Taheri et al., "A dry electrode for EEG recording," Electroencephalography and clinical Neurophysiology, pp. 376-383, Elsevier Science Ireland Ltd., 1994, 8 pages.
Talsma et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Tapert et al., "Neural Response to Alcohol Stimuli in Adolescents With Alcohol Use Disorder", Arch Gen Psychiatry (Jul. 2003), 727-735, 9 pages.
"Technology Platform: SmartShirt + Eye-Tracking," Innerscope Research, Mar. 2007, 1 page.
Thomas, "International Marketing," International Textbook Company, Scranton, PA 1971, 3 pages.
Trigaux, Robert, "Cyberwar Erupts Over Free Speech Across Florida, Nation," Knight-Ridder Tribune Business News, May 29, 2000, 4 pages.
Tull et al., "Marketing Research Measurement and Method," MacMillan Publishing Company, New York, NY, 1984, 9 pages.
Vogel et al., "Electrophysiological Evidence for a Postperceptual Human Perception Locus of Suppression During the Attentional Blink," Journal of Experimental Psychology: Human Perception and Performance, vol. 24, No. 6, pp. 1656-1674, 1998, 19 pages.
Voorhees, "The TREC-8 Question Answering Track Report," National Institute of Standards and Technology, 1999, 6 pages.
Voytek et al., "Prefrontal cortex and basal ganglia contributions to visual working memory," PNAS Early Edition, www.pnas.org/cgi/doi/10.1073/pnas.1007277107, 2010, 6 pages.
Voytek et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, Nov. 2009, 12 pages.
Wang, "Neurophysiological and Computational Principles of Cortical Rhythms in Cognition," Physiol Rev 90: pp. 1195-1268, American Physiological Society, www.prv.org, (2010), 75 pages.
Wiebe et al., "Identifying Collocations for Recognizing Opinions," in proceedings of ACL/EACL '01 Workshop on Collocation, Toulouse, France, Apr. 9, 2001, 9 pages.
Willis et al., "Discover Your Child's Learning Style: Children Learn in Unique Ways—Here's the Key to Every Child's Learning Success," Prime Publishing, 1999, 22 pages.
Wikipedia, "Functional magnetic resonance imaging," retrieved online on Aug. 23, 2011, at http://en.wikipedia.org/w/index.php?title=Functional_magnetic_resonance_imaging&oldid=319601772, Oct. 13, 2009, 8 pages.
William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursor/, Feb. 17, 2010, 3 pages.
Wise, "The High Performance Mind, Mastering Brainwaves for Insight, Healing and Creativity," G.P. Putnam's Son, New York, 1996, pp. 13-15; 20-22; 143-156, 11 pages.
Wise, "The High Performance Mind, Mastering Brainwaves for Insight, Healing and Creativity," G.P. Putnam's Son, New York, 1996, pp. 156-158; 165-170; 186-187, 15 pages.
Woldorf, "Distortion of ERP averages due to overlap from temporally adjacent ERPs: Analysis and correction," Psychophysiology, Society for Psychophysiological Research, Cambridge University Press, 1993, 22 pages.
Woodman et al., "Serial Deployment of Attention During Visual Search," Journal of Experimental Psychology: Human Perception and Performance, vol. 29, No. 1, pp. 121-138, American Physiological Association (2003), 18 pages.
Word of Mouth Research Case Study, "The Trans Fat Issue, Analysis of online consumer conversation to understand how the Oreo lawsuit impacted word-of-mouth on trans fats," Aug. 16, 2004, 35 pages.
Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.
Yang, "An Evaluation of Statistical Approaches to Text Categorization," Information Retrieval 1 (1/2) Apr. 10, 1999, 12 pages.
Yap et al., "TIMER: Tensor Image Morphing for Elastic Registration," NeuroImage, vol. 47, May 3, 2009, 15 pages.
Yuval-Greenberg, et al., "Transient Induced Gamma-Bands Response in EEG as a Manifestation of Miniature Saccades," Neuron, vol. 58, pp. 429-441, Elsevier Inc. May 8, 2008, 13 pages.
Zagat, www.zagat.com, archived on Apr. 29, 1999, 33 pages.
Zagat, www.zagat.com, archived version of p. 34, Feb. 1999, 1 page.
Zhang, "Will You Use Animation on Your Web Pages?" Doing Business on the Internet: Opportunities and Pitfalls, C. Romm and F. Sudweeks (eds.), Spring-Verlag, 1999, 17 pages.
Ziegenfuss, "Neuromarketing: Advertising Ethical & Medical Technology," The Brownstone Journal, vol. XII, Boston University, pp. 69-73, May 2005, 9 pages.
Zyga, "A Baseball Cap That Can Read Your Mind," PhysOrg.com, located at www.physorg.com/news130152277.html, May 16, 2008, 11 pages.
Merriam-Webster Online Dictionary, Definition for "Resonance," retrieved from [URL: http://www.merriam-webster.com/dictionary/resonance] on Apr. 10, 2013, 4 pages.
Enghoff, "Thesis: Moving ICA and Time-Frequency Analysis in Event-Related EEG Studies of Selective Attention," Technical University of Denmark, Dec. 1999, 54 pages.
Alibaba, "Promotional Rubber Magnetic Clip Holder," retrieved from [htpp://www.alibaba.com/rubber-magnet-clip-holder-promotion.html] on Jul. 16, 2015, 7 pages.
Nolan et al., "FASTER: Fully Automated Statistical Thresholding for EEG artifact Rejection," Journal of Neuroscience Methods 192 (2010) 152-162, Jul. 10, 2015, 12 pages.
Junghofer et al., Statistical control of artifacts in dense array EEG/MEG studies, Psychophysiology, 37 (2000), Cambridge University Press, 10 pages.
United States Patent and Trademark Office, "Notice of Allowance and Fee(s) Due," issued in connection with U.S. Appl. No. 14/859,871, dated Dec. 7, 2016, 21 pages.
United States Patent and Trademark Office, "Final Office Action," issued in connection with U.S. Appl. No. 14/859,871, dated Oct. 3, 2016, 24 pages.
United States Patent and Trademark Office, "Non-Final Office Action," issued in connection with U.S. Appl. No. 14/859,871, dated Jun. 3, 2016, 18 pages.

(56) References Cited

OTHER PUBLICATIONS

Robertson, "Sony imagines 'Smart Wig' to monitor health, give directions and read facial expressions," http://www.theverge.com/2013/11/21/5129554/bizarre-sony-smartwig-patent-turns-wigs-into-wearable-computing-device, Nov. 21, 2013, 2 pages.

International Searching Authority, "International Search Report and Written Opinion," issued in connection with International Patent Application No. PCT/US2015/022733, dated Jul. 14, 2015, 13 pages.

International Bureau, "International Preliminary Report on Patentability," issued in connection with International Patent Application No. PCT/US2015/022733, dated Oct. 13, 2016, 12 pages.

United States Patent and Trademark Office, "Notice of Allowance and Fee(s) Due," issued in connection with U.S. Appl. No. 14/293,557, dated Dec. 16, 2016, 9 pages.

United States Patent and Trademark Office, "Final Office Action," issued in connection with U.S. Appl. No. 14/293,557, dated Oct. 25, 2016, 11 pages.

United States Patent and Trademark Office, "Non-Final Office Action," issued in connection with U.S. Appl. No. 14/293,557, dated Aug. 12, 2016, 14 pages.

\* cited by examiner

METHODS AND APPARATUS TO GATHER AND ANALYZE ELECTROENCEPHALOGRAPHIC DATA

CROSS-REFERENCE TO RELATED APPLICATIONS

This patent arises from a continuation of U.S. application Ser. No. 14/293,557, titled "METHODS AND APPARATUS TO GATHER AND ANALYZE ELECTROENCEPHALOGRAPHIC DATA," filed Jun. 2, 2014, which claims priority to U.S. Provisional Application No. 61/974,847, titled "METHODS AND APPARATUS TO GATHER AND ANALYZE ELECTROENCEPHALOGRAPHIC DATA," and filed Apr. 3, 2014. U.S. application Ser. No. 14/293,557 and U.S. Provisional Application No. 61/974,847 are incorporated herein by reference in their entireties.

FIELD OF DISCLOSURE

This disclosure relates generally to neurological and physiological monitoring, and, more particularly, to methods and apparatus to gather and analyze electroencephalographic data.

BACKGROUND

Electroencephalography (EEG) involves measuring and recording electrical activity resulting from many neural processes associated with different portions of the brain. EEG data is typically measured using a plurality of electrodes placed on the scalp of a person to measure voltage fluctuations resulting from this electrical activity within the neurons of the brain.

DETAILED DESCRIPTION

Figure 1A:
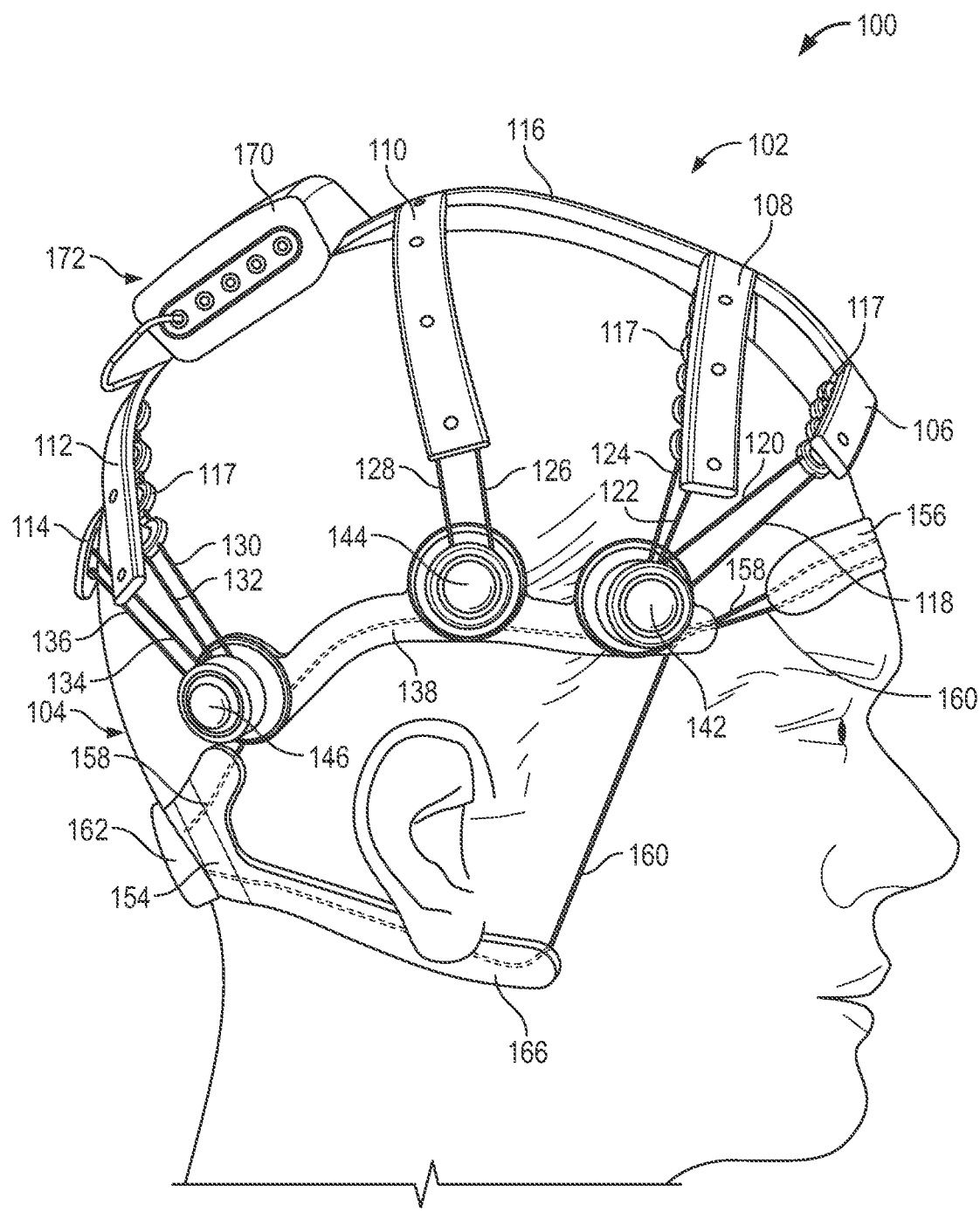
FIG. 1A is a first side view of an example headset constructed in accordance with the teachings of this disclosure for gathering EEG signals and including an example electrode assembly and an example adjustment assembly.

Certain examples are shown in the above-identified figures and/or described in detail below. As used herein, "operatively coupled" is defined as connected directly or indirectly (e.g., through one or more intervening structures and/or layers).

Electroencephalography (EEG) data is indicative of electrical activity of neurons (e.g., neural depolarization) in a brain. The neural electrical activity may be due to stimuli of one or more of the five senses (e.g., evoked activity) and/or from thought processes (e.g., spontaneous activity). Summations of these electrical activities (e.g., brainwaves) propagate to the surface (e.g., the scalp) and are detectable with electroencephalograms. Current flow in the human body is typically due to ion flow. Thus, in examples described herein, a biopotential electrode is used to form an electrical double layer with the human skin to sense ion distribution(s). The electrical double layer is the interface or interaction between the ion flow in the body that causes the electron flow in the electrode (and other electronic circuitry).

EEG data can be classified in various frequency bands. Human brainwave frequencies include delta, theta, alpha, beta and gamma frequency ranges. Delta waves are classified as waves having frequencies of less than about 4 Hertz (Hz) and are prominent during sleep. Theta waves have frequencies between about 3.5 Hz to about 7.5 Hz and are associated with memories, attention, emotions, and sensations. Theta waves are typically prominent during states of internal focus. Alpha frequencies reside between about 7.5 Hz and about 13 Hz. Alpha waves are prominent during states of relaxation. Beta waves have a frequency range between about 14 Hz and about 30 Hz. Beta waves are prominent during states of motor control, long range synchronization between areas, analytical problem solving, judgment, and decision making. Gamma waves occur between about 30 Hz and about 100 Hz and are involved in binding of different populations of neurons together into a network for the purpose of carrying out a certain cognitive or motor function, and are also present during activity involving attention and/or memory. Skull and dermal layers tend to attenuate waves above about 75 Hz and, as a result, high gamma band or kappa band waves are less easily measured than waves in lower frequency bands.

EEG data may be used to determine an emotional or mental state of a person including, for example, attention, emotional engagement, memory or resonance, etc. As used herein, "attention" is a measure of sustained focus and/or shift(s) in focus over time. As used herein, "emotional engagement" is a measure of intensity of emotional response and automatic emotional classification of stimuli. As used herein, "memory" is a measure of a formation of connections and/or retention of information, which can be explicit (e.g., readily recalled) or implicit. As used herein, "resonance" is a measure of a quality of evoked response.

EEG signals may be measured using one or more electrodes placed on a scalp of a person (e.g., a user, a viewer, a subject, a panelist, a participant or a patient) to measure voltage fluctuations resulting from electrical activity associated with post synaptic currents occurring within neurons of the person's brain.

To enable surface EEG electrodes to effectively receive signals from the brain, the electrodes are placed close to the scalp. The electrodes may be manually placed upon a subject's head or may be contained in a wearable apparatus such as, for example, a headset. Many known EEG headsets utilize a bulky helmet or complicated head-strap type assembly. To decrease impedance and improve signal quality, these headsets are typically strapped tightly onto a user's head to decrease the distance between the electrodes and the tissue of the scalp. However, too much pressure (e.g., greater than two Newtons per millimeter square ($N/mm^2$)) results in discomfort for most subjects. Further, these known headsets have limited adjustability and are often uncomfortable to wear because they do not adequately account for differently size(s) and/or shape(s) of heads.

Example headset(s) for receiving neuro-response data from a person's brain are disclosed herein. Example headsets disclosed herein are portable and comprise an electrode assembly having a plurality of adjustable strips. Such example headsets are adjustable to enhance comfort and reduce noise, as disclosed in greater detail below. Some such example headsets provide a simple, cost effective and reliable solution for the use of a large number of dry electrodes. Some such example headsets ensure comfort, good electrode contact, through the hair operation, and/or shielding against line noise and/or other type(s) of noise. Examples disclosed herein also include removable and adjustable components to enhance comfort, wearability and/or safety.

Example headsets disclosed herein include a first support to be disposed on a first side of a head of a person and a second support to be disposed on a second side of the head of the person. In some such examples, the headset also includes a first adjustor coupled to the first support, a first electrode strip and a first tension strap (e.g., an elastic member, a band, a string, a line, a strip, a spring, a belt, a tensioner, a cord, etc.) having a first end operatively coupled to the first adjustor and a second end operatively coupled to the second support.

In some such examples, the headset includes a second adjustor operatively coupled to the second support. In some such examples, the second end of the first tension strap is operatively coupled to the second support via the second adjustor.

Some example headsets include a second electrode strip and a second tension strap having a first end operatively coupled to the first support and a second end operatively coupled to the second support. In some examples, the first electrode strip and/or the second electrode strip are carried by the first and second supports. In some examples, the first end of the second tension strap is operatively coupled to the first adjustor on the first support. In some examples, the headset also includes a second adjustor operatively coupled to the first support. In some such examples, the first end of the second tension strap is operatively coupled to the second adjustor. In some example headsets, a second adjustor is operatively coupled to the second support. In some such examples, the second end of the second tension strap is operatively coupled to the second support via the second adjustor. In some examples, the headset includes a second adjustor on the second support and a third adjustor on the first support. In some such examples, the second end of the first tension strap is operatively coupled to the second support via the second adjustor and the first end of the second tension strap is operatively coupled to the first support via the third adjustor. In some such examples, the headset includes a fourth adjustor operatively coupled to the second support. In some such examples, the second end of the second tension strap is operatively coupled to the second support via the fourth adjustor. In some such examples, the first strip and the second strip are independently adjustable relative to the first support and the second support. In some examples, the first tension strap is slidably received by the first electrode strip and the second electrode strip.

In some examples, movement of the first adjustor changes a tension of the first tension strap. In some examples, movement of the first adjustor changes an effective length of the first tension strap. In some examples, the first adjustor comprises a wheel rotatably coupled to the first support. In some such examples, the first tension strap is wound about the wheel when the wheel is rotated. In some examples, the first adjustor comprises an electric motor to adjust the first tension strap.

In some examples, the first adjustor is detachable from the first support. In some examples, the first tension strap comprises nylon.

In some examples, the adjustment assembly includes a third support to be disposed under a right ear of the person and a fourth support to be disposed under a left ear of the person. In some examples, the first support is to be disposed above the right ear of the person and the second support is to be disposed above the left ear of the person. In some examples, the third support and the fourth support are adjustably coupled to the first support and the second support, respectively.

In some examples, the adjustment assembly includes a third support to be disposed on a front of the head of the person. In some such examples, the third support is adjustably coupled to the first support and the second support.

Some example headsets include a central support strip that is to be disposed along a top of the head of the person from a front of the head (e.g., a forehead) to a back of the head. In some examples, the first electrode strip is supported by the central support strip.

In some examples, the headset further includes a processing unit removably coupled to the central support strip. In some examples, the processing unit includes circuitry and/or a semiconductor based processor to at least one of amplify, filter, store or analyze signals gathered by electrodes on the headset. In some examples, the processing unit includes a first electrical connector and the central support strip includes a second electrical connector to mate with the first electrical connector.

In some examples, the central support strip comprises an annular rim and the processing unit comprises a hub to slidably receive the annular rim. In some examples, the headset includes a reference electrode and the processing unit comprises a port to communicatively couple the reference electrode to the processing unit.

In some examples, the first side is a rear of the head and the second side is a front of the head.

Also disclosed herein are headsets that include a first strip to be disposed over a head of a person and a first electrode unit operatively coupled to the first strip. In some such example headsets, the first electrode unit comprises a first housing and a first electrode pin that is retractable into the first housing.

In some examples, the first electrode unit includes a first spring to bias the first electrode pin outward from the first housing. In some such examples, the first spring is to provide about (e.g., +/−0.04 Newtons) 0.2 Newtons of force to the first electrode pin.

In some examples, the first electrode pin is retractable into the first housing from an extended position to a fully retracted position, wherein an end of the first electrode pin is substantially flush with a surface of the first housing.

In some examples, the first electrode unit comprises a second electrode pin that is retractable into the first housing. In some such examples, the first electrode pin and the second electrode pin are independently movable relative to the first housing. In some examples, the headset also includes a second electrode unit operatively coupled to the first strip, the second electrode unit having a second housing. In some such examples, the second electrode unit comprises a third pin and a fourth pin that are retractable into the second housing. In some examples, the headset includes a second strip to be disposed over the head of the user. In some such examples, the headset also includes a third electrode unit and a fourth electrode unit operatively coupled to the second strip, the third electrode unit having a third housing and the fourth electrode unit having a fourth housing. In some such examples, the third electrode unit comprises a fifth electrode pin that is retractable into the third housing and the fourth electrode unit comprises a sixth electrode pin that is retractable into the fourth housing.

In some examples, an end of the first electrode pin, which is to contact the head of a person, is substantially flat. In some examples, the first electrode pin has a diameter of about (e.g., +/−0.04 millimeters) 0.80 millimeters. In some examples, at least a portion of the first electrode pin is coated with silver.

In some examples, a surface of the first housing from which the first pin is extendable is curved. In some such examples, the surface of the first housing is concave.

In some examples, the first housing comprises a first channel to receive a first tension strap. In some such examples, the first housing comprises a second channel to receive a second tension strap. In some examples, the first tension strap and the second tension strap traverse along a longitudinal axis of the first strip. In some examples, the first channel and the second channel are substantially parallel (e.g., within +/−0.5 degrees of parallel). In some examples, tightening the first tension strap pulls the first electrode unit closer to or against the head of the person. In some such examples, the first electrode pin retracts into the first housing as the first electrode unit is pulled toward the head of the person. In some such examples, the first electrode pin is biased against the head of the user.

In some examples, the headset also includes a first tension strap slidably coupled to the first strip, a first support to be disposed on a first side of the head of the person and a second support to be disposed on a second side of the head of the person. In some such examples, a first end of the first tension strap is operatively coupled to the first support and a second end of the first tension strap is operatively coupled to the second support.

In some examples, the headset includes a first adjustor operatively coupled to the first support, and the first end of the first tension strap is operatively coupled to the first adjustor. In some such examples, the headset includes a second adjustor coupled to the second support, and the second end of the first tension strap is operatively coupled to the second adjustor. In some examples, the headset includes a second tension strap slidably coupled to the first strip. In some such examples, a first end of the second tension strap is operatively coupled to the first adjustor and a second end of the second tension strap is operatively coupled to the second adjustor.

In some examples, the headset includes a third support coupled to the first support and the second support via a second tension strap. In some such examples, the headset also includes a first adjustor coupled to the third support to change a tension of the second tension strap to move the first support and the second support in a first direction. In some such examples, the first adjustor comprises a wheel rotatably coupled to the third support. In some such examples, rotating the wheel changes the tension of the second tension strap. In some examples, the headset includes a second adjustor operatively coupled to the third support. In such an example, the third support is operatively coupled to the first support and the second support via a third tension strap. Also, in such an example, the second adjustor is to change a tension of the third tension strap to move the first support and the second support in a second direction, different than the first direction.

Also disclosed herein are methods that include adjusting a first adjustor to change a first tension in a first tension strap operatively coupled between a first support and a second support. In some such examples, the first support is to be disposed on a first side of a head of a person and the second support is to be disposed on a second side of the head of the person. In some examples, the first tension change causes the first tension strap to slide relative to a first electrode strip comprising a first electrode pin to thereby cause the first electrode strip to move to adjust a first distance of the first electrode strip relative to the head. Some such example methods also include gathering a first set of signals from the head using the first electrode pin.

In some examples, the method includes adjusting a second adjustor coupled to the second support to change the tension in the first tension strap.

In some example methods, adjusting the first adjustor changes a second tension in a second tension strap coupled between the first support and the second support. In some such examples, the second tension change causes the second tension strap to slide relative to a second electrode strip comprising a second electrode pin to thereby cause the second electrode strip to move to adjust a second distance of the second electrode strip relative to the head.

In some examples, the method includes changing an effective length of the first tension strap by adjusting the first adjustor. Also, in some examples, adjusting the first adjustor comprises rotating a wheel. In some examples, adjusting the first adjustor comprises actuating an electric motor.

Some example methods disclosed herein also include detaching the first adjustor from the first support to remove the first electrode strip.

Some example methods include adjusting a second adjustor to alter the position of a third support to be disposed under a right ear of the person and a fourth support to be disposed under a left ear of the person relative to the first support, which is to be disposed above the right ear of the person, and the second support, which is to be disposed above the left ear of the person.

Also disclosed herein are example methods wherein adjusting the first adjustor causes the first electrode pin to retract or extend from a first housing operatively coupled to the first electrode strip.

Figure 1B:
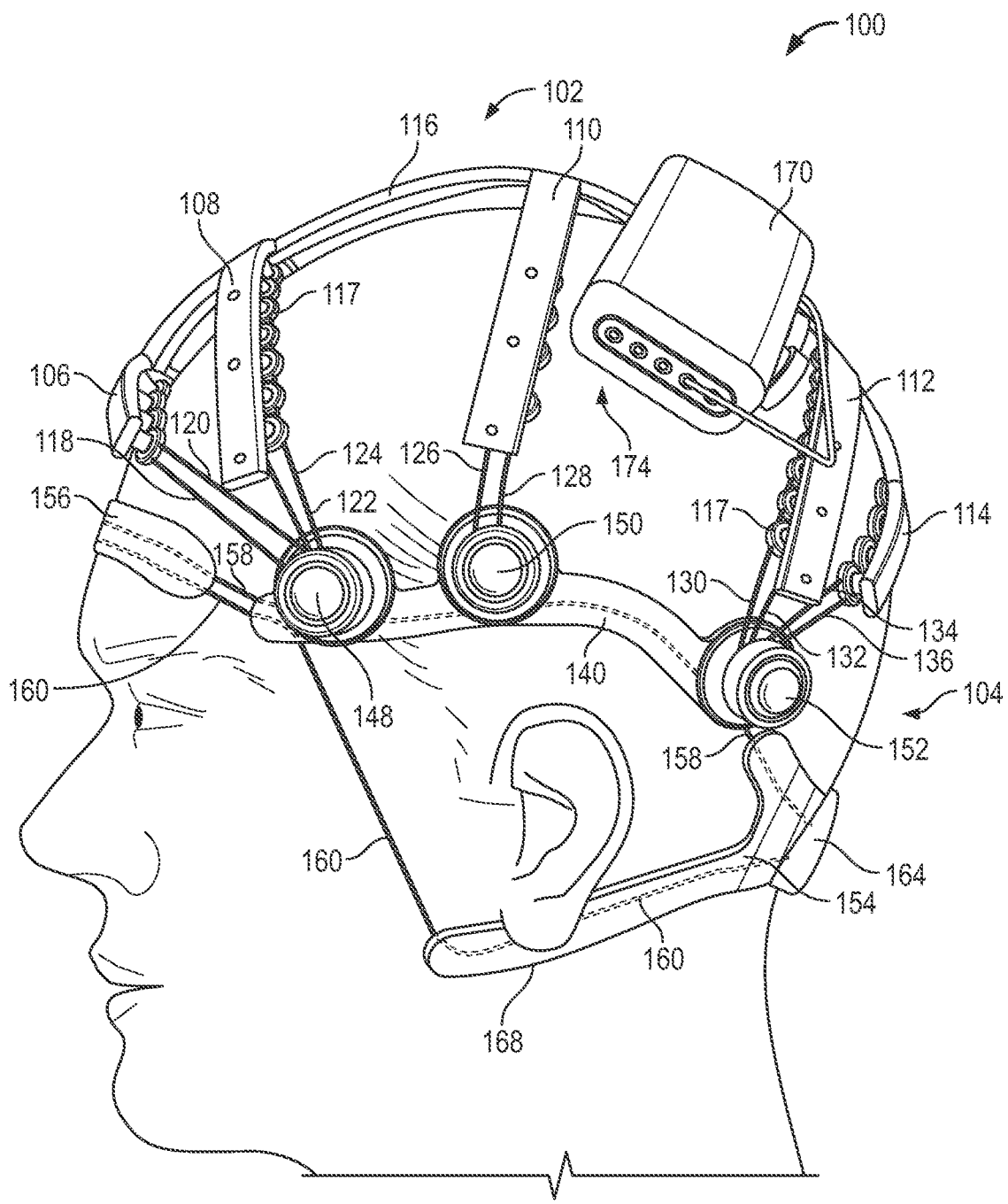
FIG. 1B is a second side view of the example headset shown in FIG. 1A.
Figure 1C:
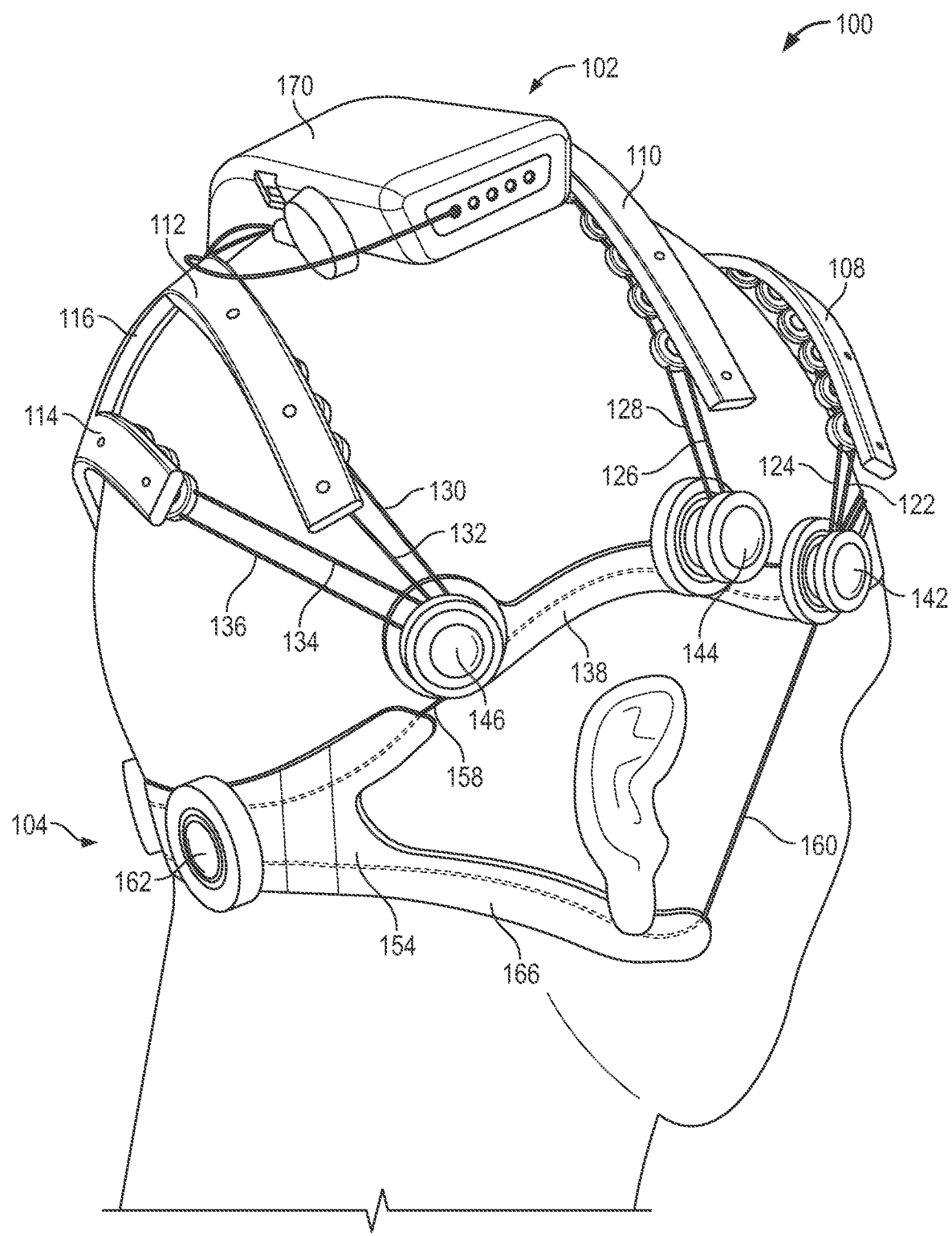
FIG. 1C is a right rear perspective view of the example headset shown in FIG. 1A.
Figure 1D:
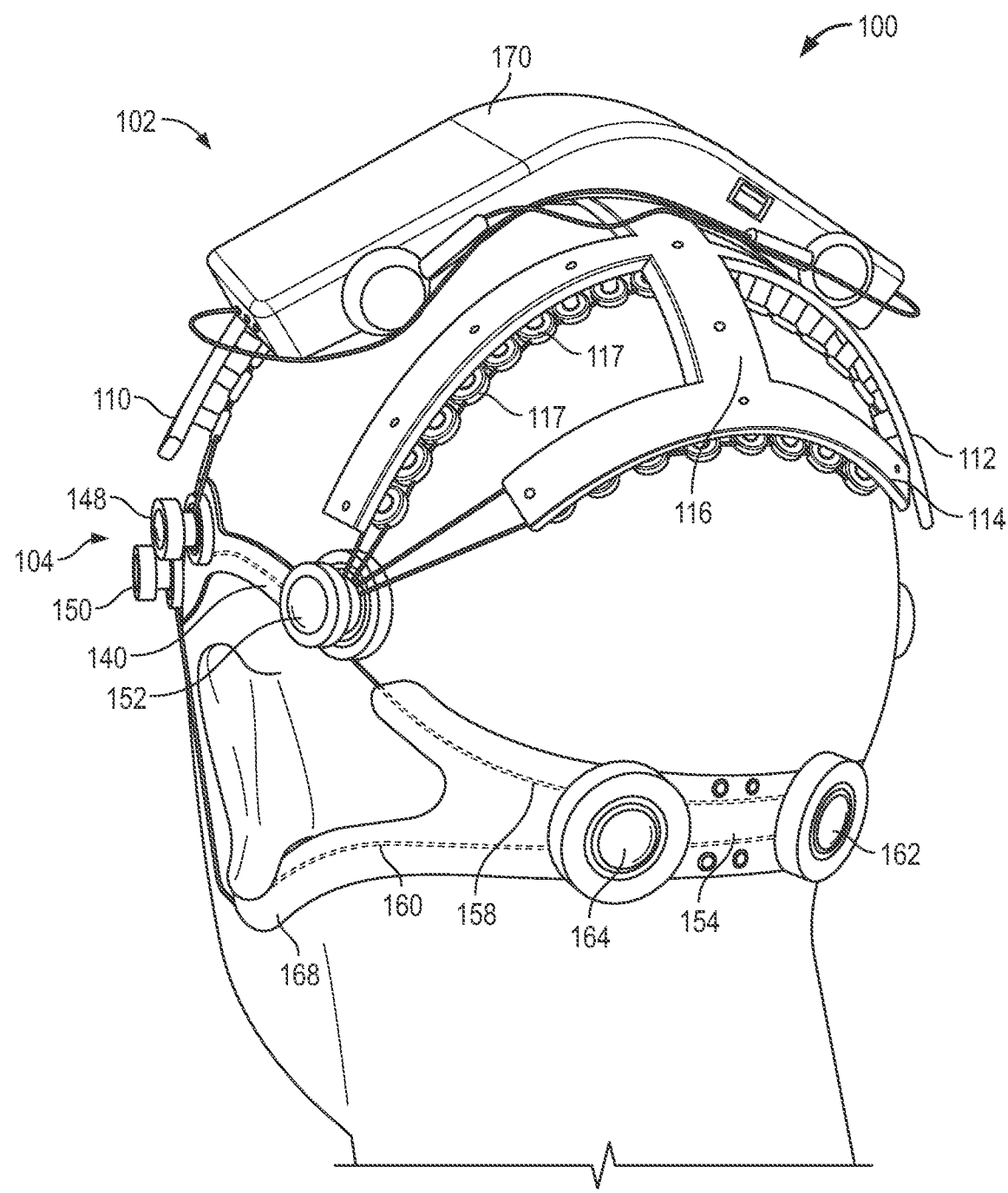
FIG. 1D is a left rear perspective view of the example headset shown in FIG. 1A.
Figure 1E:
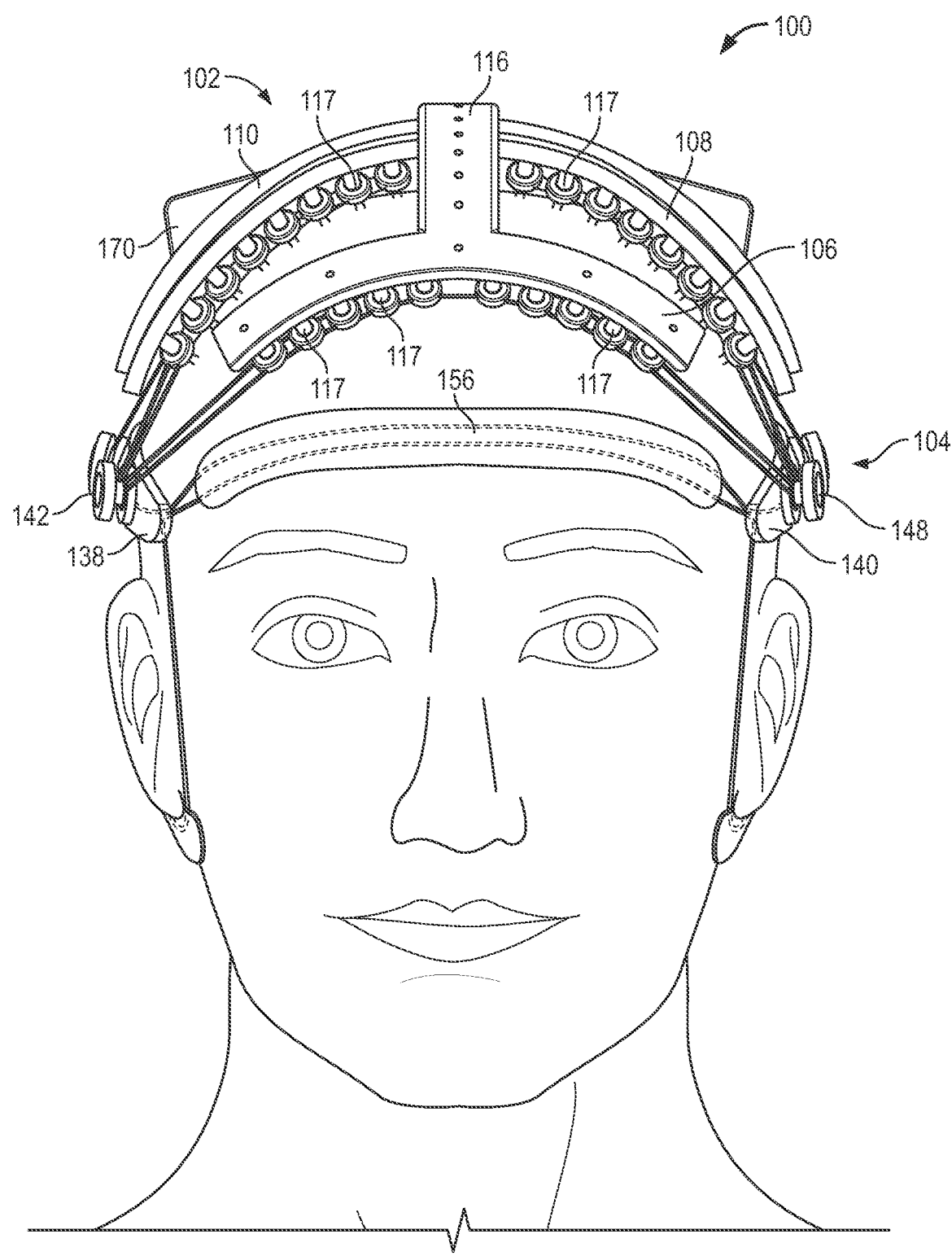
FIG. 1E is a front view of the example headset shown in FIG. 1A.

Turning now to the figures, FIGS. 1A-1E show an example headset 100 for gathering EEG signals from the head of a person. FIGS. 1A and 1B are right and left side views, respectively, of the headset 100 on a person's head. FIGS. 1C and 1D are perspective views of the right/rear side and the left/rear side, respectively, of the headset 100 on a person's head. FIG. 1E is a front view of the headset 100 on a person's head. The example headset 100 of FIGS. 1A-1E may be used, for instance, to gather medical information from a patient in a medical or a home environment, to control aspects of a game or other entertainment device, to provide data as part of a fitness regime, to collect audience measurement data, to control remote devices, for home automation, and/or for multiple other uses. The example headset 100 of FIGS. 1A-1E is intended to be worn on the head of a person, a user, a subject, a viewer, a participant and/or a panelist. A panelist may be, for example, a user registered on a panel maintained by a ratings entity (e.g., an audience measurement company) that owns and/or operates a ratings entity subsystem.

The example headset of FIGS. 1A-1E includes an electrode assembly 102 (e.g., a sensor module) and an adjustment assembly 104. The electrode assembly 102 of the illustrated example is generally located at the top and sides of the headset 100 and is structured to collect EEG signals. The adjustment assembly 104 of the illustrated example is the portion of the headset used to adjust the fit of the headset 100 to the head of a person. The electrode assembly 102 of the example headset 100 of FIGS. 1A-1E includes a plurality of strips including a first strip 106, a second strip 108, a third strip 110, a fourth strip 112 and a fifth strip 114. Each of the strips 106, 108, 110, 112, 114 includes a plurality of electrodes for receiving signals from the head of the user.

The electrode assembly 102 of the illustrated example includes a central support member 116. The strips 106-114 are operatively coupled to the central support member 116. In the illustrated example, the strips 106-114 and the central support member 116 are formed as a unitary piece (e.g., molded as one component). In other examples, one or more of the strips 106-114 and/or the central support member 116 are separate components that are mechanically coupled together to form the electrode assembly 102. In some examples, the distance between the respective strips 106-114 is fixed. However, in other examples, the electrode assembly 102 is adjustable to change the distance between any two of the strips 106-114 along the central support member 116. In some examples, the strips 106-114 are adjustably coupled to the central support member 116.

In the illustrated example, the electrode assembly 102 is worn on the head of a user such that the strips 106-114 are disposed over the head of the user and span between the left side of the head to the right side of the head. In the illustrated example, the central support member 116 is disposed over the head and extends between the back of the head to the front (e.g., the forehead) of the head. The example electrode assembly 102 of FIGS. 1A-1E is removably attached to the adjustment assembly 104, via the strips 106-114 (discussed in further detail below). The strips 106-114 of the illustrated example are moveable and adjustable (e.g., tightenable) on the head of the user to comfortably position the strips 106-114 on the head of the user for effective reading of neural electrical activity. In the illustrated example, the electrode assembly 102 includes five strips 106-114. However, in other examples, the electrode assembly 102 includes fewer or more strips (e.g., four or less strips, six strips, seven strips, ten or more strips, etc.) for disposing electrodes along the scalp of the user. Also, in other examples, one or more of the strips may be oriented perpendicularly, angularly and/or at different orientations than the other strips.

In the illustrated example, the first strip 106 includes a plurality of electrode units 117 that include one or more electrodes (discussed in further detail below). In the illustrated example, the electrodes units 117 of the first strip 106 are integrated into and/or operatively coupled to the first strip 106. The first strip 106 may also include internal electrical components (e.g., a printed circuit board ("PCB"), communication links, etc.) to transfer the electrical signals gathered by the electrode unit(s) 117 to a processor (discussed in further detail below). In the illustrated examples, the first strip 106 includes ten electrode units 117. In other examples, the first strip 106 includes more (e.g., twenty) or fewer electrode units.

In the illustrated example, the electrode units 117 of the first strip 106 are aligned along the length (e.g., the longitudinal axis) of the first strip 106. In other examples, the first strip 106 includes pairs of electrodes along the length such as, for example, in a spine-like structure. Disclosure of example spine structures can be found in U.S. patent application Ser. No. 13/728,900, titled "SYSTEMS AND METHODS TO GATHER AND ANALYZE ELECTROENCEPHALOGRAPHIC DATA," filed on Dec. 27, 2012; U.S. patent application Ser. No. 13/728,913 titled "SYSTEMS AND METHODS TO GATHER AND ANALYZE ELECTROENCEPHALOGRAPHIC DATA," filed on Dec. 27, 2012; and U.S. patent application Ser. No. 13/730,212, titled "SYSTEMS AND METHODS TO GATHER AND ANALYZE ELECTROENCEPHALOGRAPHIC DATA," filed on Dec. 28, 2012, all of which claim priority to U.S. Provisional Patent Application Ser. No. 61/684,640, titled SYSTEMS AND METHODS TO GATHER AND ANALYZE ELECTROENCEPHALOGRPHIC DATA, filed on Aug. 17, 2012, and all of which are incorporated herein by reference in their entireties.

In the illustrated example of FIGS. 1A-1E, the first example strip 106 includes a first tension strap 118 and a second tension strap 120. The first tension strap 118 and the second tension strap 120 of the first strip 106 are slidably coupled to the first strip 106 and are adjustable (e.g., tightenable and/or releasable) along the first strip 106 to provide a downward force toward or against the scalp of the user. The first and second tension straps 118, 120 of the first strip 106 extend through openings formed in the electrode units (described in further detail below). Thus, increasing or decreasing the tension in the first and second straps 118, 120 of the first strip 106 moves the first strip 106 and the electrode units 117 closer to or further from the scalp of the user. The first and second tension straps 118, 120 of the first strip 106 may comprise wires, cords, lines, ties, straps, tethers, springs, belts, adjustment elements, and/or other suitable connecting elements. In some examples, the first and second tension straps 118, 120 of the first strip 106 comprise nylon. Additionally or alternatively, in some examples, the first and second tension straps 118, 120 of the first strip 106 are stretchable and comprise an elastic element.

In the illustrated example shown in FIGS. 1A-1E, the first and second tension straps 118, 120 of the first strip 106 are adjustable to change forces imparted by electrode pins (e.g., electrode pins 218, 220, 222 shown in FIGS. 2A-2C and disclosed in detail below) of the electrode units 117 on the scalp of the user. For example, when first and second tension straps 118, 120 of the first strip 106 are tightened, the first and second tension straps 118, 120 provide a downward force to pull the first strip 106 and the respective electrode units 117 toward and/or against the scalp of the user. The first and second tension straps 118, 120 may be tightened, for example, to increase signal quality for the signals gathered by the electrode units 117. Additionally, when the first and second tension straps 118, 120 of the first strip 106 are loosened, the first and second tension straps 118, 120 decrease the downward force and allow the electrode units 117 of the first strip 106 to move away from the head, which could provide increased comfort to a person wearing the headset 100.

In the illustrated example of FIGS. 1A-1E, the second strip 108, the third strip 110, the fourth strip 112 and the fifth strip 114 also include a respective first tension strap, a respective second tension strap, and a plurality of electrode units 117, similar to the first strip 106 described above. Specifically, the second strip 108 includes a first tension strap 122 and a second tension strap 124, the third strip 110 includes a first tension strap 126 and a second tension strap 128, the fourth strip 112 includes a first tension strap 130 and a second tension strap 132 and the fifth strip 114 includes a first tension strap 134 and a second tension strap 136. In the example, each of the strips 108-114 slidably receives the respective first and second tension straps 122-136, as described above with the first strip 106. Each of the tension straps 122-136 may likewise comprise wires, cords, lines, ties, straps, tethers, springs, belts, adjustment elements, nylon, elastic and/or other suitable connecting elements, similar to the first and second tensions straps 118, 120 of the first strip 106. In some examples, each of the strips 106-114 includes only one tension strap. However, in other examples, each of the strips 106-114 includes three or more tension straps. In some examples, the strips 106-114 include a different number of tension straps depending on the desired adjustment capabilities. For example, one of the strips may only include one tension strap while another strip on the same headset may include two or more tension straps.

In some examples, each of the strips 106-114 includes ten to twenty electrode units 117, such that the example headset 100 includes fifty to one hundred electrode units. In other examples, the headset 100 and/or one or more of the strips 106-114 include more or fewer electrode units.

Similar to the first strip 106 describe above, the respective first and second tension straps 122-136 of the second, third, fourth and fifth strips 108-114 are adjustable (e.g., tightenable and/or releasable) along the respective strips 108-114 to change forces imparted by the electrode pins (e.g., electrode pins 218, 220, 222 shown in FIGS. 2A-2C and disclosed in detail below) of the electrode units 117 of the strips 108-114 on the scalp of the user. Each of the strips 106-114 is independently adjustable (e.g., via its respective tension straps 118-136), relative to the other strips 106-114, to position each of the strips 106-118 against the head of the user with a desired degree of tension.

The example strips 106-114 and the central support member 116 of the illustrated example are constructed of a flexible material such as, for example, a plastic (e.g., a thermoplastic), a rubber, a polyurethane, a silicone and/or any other suitable material or combination of materials. The flexibility of the example strips 106-114 and the central support member 116 enables the electrode assembly 102 to sit comfortably on the head of a person and to adjust to the shape of the head of the person without applying an uncomfortable and/or painful force to the head. The flexibility of the example strips 106-114 and the central support member 116 also enables the electrode assembly 102 to lie close to the scalp of the user to allow the electrodes of the electrode units 117 of the strips 106-114 to engage the surface of the scalp, thus, resulting in better contact and signal collection.

The example strips 106-114 of FIGS. 1A-1E are removably attached to the adjustment assembly 104. As shown in FIGS. 1A-1E, the adjustment assembly 104 includes a first support or band 138 that is to be disposed on a first side (e.g., the right side) of the head of the user and a second support or band 140 that is to be disposed on a second side (e.g., the left side) of the head of the user. In some examples, the first support 138 and the second support 140 are constructed of a flexible material such as, for example, a plastic (e.g., a thermoplastic), a rubber, a polyurethane, a silicone and/or any other suitable material or combination of materials.

The example headset 100 of FIGS. 1A-1E includes a first adjustor 142, a second adjustor 144 and a third adjustor 146. The first adjustor 142, the second adjustor 144 and third adjustor 146 are removably coupled to the first support 138. Likewise, in the example shown in FIG. 1B, a fourth adjustor 148, a fifth adjustor 150 and a sixth adjustor 152 are removably coupled to the second support 140. The adjustors 142-152 of the illustrated example are spaced along respective supports 138, 140 and adjustably couple the strips 106-114 of the electrode assembly 102 to the first and second supports 138, 140 via respective tension straps 118-136.

In the illustrated example shown in FIGS. 1A-1E, the first and second tension straps 118, 120 of the first strip 106 are operatively coupled to the first adjustor 142 on the first support 138 on the right side of the head of the user and operatively coupled to the fourth adjustor 148 on the second support 140 on the left side of the head of the user. The first and fourth adjustors 142, 148 are operable to change tension in and/or alter effective lengths of the first and second tension straps 118, 120 of the first strip 106. Thus, the first and fourth adjustors 142, 148 change the location and/or pressure (e.g., change the application of force or compression) of the first strip 106 on the head of the user.

In the illustrated example shown in FIGS. 1A-1E, the first and fourth adjustors 142, 148 include wheels (e.g., knobs or other rotatable elements) that are rotatably and removably attached to the first and second supports 138, 140. As the wheel of the first adjustor 142 rotates, the first and second tension straps 118, 120 of the first strip 106 are wound onto the wheel and, thus, the effective lengths of the first and second tension straps 118, 120 are altered. As a result, the first and second tension straps 118, 120 of the first strip 106 tighten or loosen, which changes the tension of the tension straps 118, 120 and the forces pulling the first strip 106 and the electrode units 117 against the head of the user. In some examples, the wheel of the first adjustor 142 is held in position by friction, such that when a user rotates the wheel in one direction (e.g., to tighten the electrode assembly 102), friction prevents the wheel from turning back in the other direction (e.g., due to the tension forces in the first and second tension straps 118, 120 and biasing forces acting in the opposite direction, which are disclosed in greater detail below). In other examples, the adjustor 142 includes a ratchet assembly to lock the wheel in a position. In still other examples, the adjustor 142 includes an electric motor to adjust (e.g., automatically) the tension in the first and second tension straps 118, 120.

Similar to the attachment of the first and second tension straps 118, 120 of the first strip 106 to the first and fourth adjustors 142, 148, each of the strips 108-114 is likewise attached to respective ones of the adjustors 142-152, as shown in the illustrated example of FIGS. 1A-1E. Specifically, the second strip 108 is attached to the first and fourth adjustors 142, 148, the third strip 110 is attached to the second and fifth adjustors 142, 150, the fourth strip 112 is attached to the third and sixth adjustors 146, 152, and the fifth strip 114 is attached to the third and sixth adjustors 146, 152. The tension straps 118-136 of the strips 106-114 of the illustrated example are coupled to the adjustors 142-152 such that the adjustors 142-152 are able to change tension in and/or alter effective lengths of the tension straps 118-136. Specifically, the first and second tension straps 122, 124 of the second strip 108 are coupled to the first and fourth adjustors 142, 148, the first and second tension straps 126, 128 of the third strip 110 are coupled to the second and fifth adjustors 142, 150, the first and second tension straps 130, 138 of the fourth strip 112 are coupled to the third and sixth adjustors 146, 152, and the first and second tension straps 134, 136 of the fifth strip 114 are coupled to the third and sixth adjustors 146, 152. Thus, the adjustors 142-152 change the location and/or pressure (e.g., change the application of force or compression) of respective ones of the strips 106-114 on the head of the user. In some examples, the adjustors are not removably coupled to a respective support.

In some examples, one or more of the strips 106-114 is carried by the first and second supports 138, 140.

Specifically, as shown in the example of FIG. 1A, the first and second tension straps 118, 120 of the first strip 106 and the first and second tension straps 122, 124 of the second strip 108 are operatively coupled to the first adjustor 142 on the first support 138. Also, the first and second tension straps 126, 128 of the third strip 110 of the illustrated example are operatively coupled to the second adjustor 144 on the first support 138. Further, in the example of FIGS. 1A-1E, the first and second tension straps 130, 132 of the fourth strip 112 and the first and second tension straps 134, 136 of the fifth strip 114 are operatively coupled to the third adjustor 146 on the first support 138. Thus, in the illustrated example, a single adjustor may simultaneously adjust a plurality of tension straps. In other examples, one adjustor controls one tension strap. In still other examples, a first tension strap of a strip may be coupled to a first adjustor, and a second tension strap of the same strip may be coupled to a second adjustor. In such example, a strip may be finely adjusted by variably and independently changing a pressure on different sides of the strip.

Similarly, as shown on the left side of the head in FIG. 1B, the first and second tension straps 118, 120 of the first strip 106 and the first and second tension straps 122, 124 of the second strip 108 are operatively coupled to the fourth adjustor 148 on the second support 140. The first and second tension straps 126, 128 of the third strip 110 are operatively coupled to the fifth adjustor 150 on the second support 140, and the first and second tension straps 130, 132 of the fourth strip 112 and the first and second tension straps 134, 136 of the fifth strip 114 are operatively coupled to the sixth adjustor 152 on the second support 140.

In the illustrated example, each of the first and second supports 138, 140 includes three adjustors. However, in other examples, the headset 100 may include more or fewer adjustors. In some examples, five adjustors are coupled to each of the first and second supports 138, 140, one for each of the respective strips 106-114 of the electrode assembly 102. In other words, in some examples, each strip 106-114 is attached to a different adjustor on each end, as described above. In some examples, each of the strips 106-114 is independently adjustable relative to the other strips 106-114. In other examples, the first and second supports 138, 140 each include only one adjustor such that all of the tension straps 118-136 are all attached to the single adjustor on each side of the head. In such an example, the strips 106-114 are simultaneously adjustable on each end.

In the illustrated example, the strips 106-114 are coupled to the first and second supports 138, 140 via the adjustors 142-152. However, in other examples, the headset 100 lacks the fourth, fifth and sixth adjustors 148-152, and the second ends of the tension straps 118-136 are fixedly coupled to the second support 140. Alternatively, in other examples, the headset 100 lacks the first, second and third adjustors 142-146, and the first ends of the tension straps 118-136 are fixedly coupled to the first support 140. In other words, in some examples, an adjustor may be located on only one of the first or second supports 138, 140 to adjust a respective strip. In yet other examples, some strips are coupled to adjustors on one support and other strips are coupled to adjustors on another support.

Similar to the first adjustor 142 described above, the other adjustors 144-152 of the illustrated example also include wheels (e.g., knobs or other rotatable elements) that are rotatably and removably attached to the first and second supports 138, 140. In the illustrated example, the adjustors 142-152 are independently adjustable relative to the other adjustors 142-152. The arrangement of the adjustors 142-152 of the illustrated example enables the strips 106-114 to be disposed over the head of the person and attached to the first and second supports 138, 140, respectively.

In some examples, the adjustors 142-152 are detachable from the respective first and second supports 138, 142. In some examples, the adjustors 142-152 are coupled to the respective tension straps 118-136 first, and then the electrode assembly 102 is attached to the adjustment assembly 104 by attaching the adjustors 142-152 to the first and second supports 138, 140. The adjustors 142-152 may be removably attached to the respective first and second supports 138, 140 using any suitable releasable fastening mechanism(s). In some examples, the adjustors 142-152 include magnets to mate with other magnets or magnetic components associated with the first and second supports 138, 140, or vice versa. A description of an example magnetic attachment assembly can be found in U.S. patent application Ser. No. 13/829,849, titled "METHODS TO APPARATUS TO GATHER AND ANALYZE ELECTROENCEPHALOGRAPHIC DATA," filed on Mar. 14, 2013, which is incorporated herein by reference in its entirety.

In the example headset 100 of FIGS. 1A-1E, the adjustment assembly 104 also includes a rear support 154 and a front support 156. The front support 156 is to be disposed on a forehead, and the rear support 154 is to be disposed on the back of the head. In some examples, the rear support 154 is disposed below the inion of the occipital bone as shown in FIGS. 1C and 1D. In some examples, the rear support 154 is constructed of a flexible material such as, for example, a plastic (e.g., a thermoplastic), a rubber, a polyurethane, a silicone and/or any other suitable material or combination of materials. In some examples the rear support 154 is a solid unitary piece. However, in other examples, the rear support 154 is constructed of multiple sections or portions that are fastened together (e.g., via a snap fastener, a tie, a loop and hook fastener such as a VELCRO® fastener, or any other suitable fastener).

In the illustrated example, the adjustment assembly 104 includes a first adjustment line 158 and a second adjustment line 160. In some examples, the first and second adjustment lines 158, 160 are similar in structure and/or function to the tension straps 118-136. The adjustment lines 158, 160 may be implemented by a wire, a cord, a tie, a strap, a tether and/or any other suitable connecting elements. In some examples, the adjustment lines 158, 160 include nylon. Additionally or alternatively, in some examples, the adjustment lines 158, 160 are stretchable and include an elastic element.

In the example of FIGS. 1A-1E, the first adjustment line 158 is slidably received by the rear support 154 and is coupled to the first support 138, the second support 140 and the front support 156. In the illustrated example, the first adjustment line 158 passes through the length of the first support 138 and the length of the second support 140 to the front support 156. In some examples, the first adjustment line 158 is a complete band or loop, while in other examples, the first adjustment line 158 includes separate sections or components coupled together.

In the illustrated example, the rear support 154 includes a first rear adjustor 162 to change a tension of the first adjustment line 158. The first adjustment line 158 of the illustrated example is slidably received within a channel (e.g., a passage, a through hole, a conduit) in the rear support 154. In some examples, the first rear adjustor 162 includes a wheel that is rotatable to change an effective length of the first adjustment line 158 and, thus tighten or loosen the tension of the first adjustment line 158. As the first adjustment line 158 is tightened, the forces in the first adjustment line 158 pull the first and second supports 138, 140 backward towards the rear support 154 on the back of the head and/or pulls the rear support 154 forward. The tension also pulls the front support 156 against the forehead of the user, which more securely holds the headset 100 on the head. This adjustment arrangement allows the headset to be adjusted for users with differently sized heads to adjust the distance between the rear support 154, the first and second support 138, 140 and the front support 156. Thus, one headset 100 can accommodate different head sizes.

In addition, different headset templates of different sizes may be used to accommodate different head sizes of different ranges. For example, one headset template could be used for a first range of smaller head sizes and another template could be used for a second range of larger head sizes. In some examples, the different templates could include different size electrode assemblies and/or different sized adjustment assemblies to accommodate different size heads. For example, a person with a head measuring 62-64 centimeters (cm) in circumference may use an electrode assembly with strips measuring a first length, and a person with a head measuring 58-62 cm in circumference may use an electrode assembly with strips measuring a second length, shorter than the first length. Therefore a plurality of different sized electrode assemblies and/or adjustment assemblies may be used with a headset to comfortably accommodate any sized/shape head.

As noted above, the adjustment assembly 104 of the illustrated example also includes the second adjustment line 160. The second adjustment line 160 is slidably received by the rear support 154 and is coupled to the first support 138, the second support 140 and the front support 156. The second adjustment line 160 of this example is slidably received within a channel (e.g., a passage, a through hole, a conduit) in the rear support 154. As shown in FIGS. 1A-1D, the rear support 154 of the illustrated example includes two lower guide sections 166, 168, which extend below the ears of the user. The second adjustment line 160 passes through the lower guide sections 166, 168 (e.g., under the ears) and is directed upward toward front ends of the first and second supports 138, 140. In some examples, the second adjustment line 160 is formed of a complete loop, while in other examples, the second adjustment line 160 includes separate sections or components coupled together.

The rear support 154 also includes a second rear adjustor 164 to change a tension of the second adjustment line 160. In some examples, the second rear adjustor 164 includes a wheel that is rotatable to change an effective length of the second adjustment line 160 and, thus, adjust the tension in the second adjustment line 160. As the second adjustment line 160 is tightened, the forces in the second adjustment line 160 pull the first and second supports 138, 140 downward toward the ends of the guides 166, 168, which are positioned below the ears and/or pulls the rear support 154 and/or the guides 166, 168 upward and/or forward. This adjustment further aides the accommodation of differently sized heads.

In some examples, the front support 156 is constructed of a flexible material such as, for example, a plastic (e.g., a thermoplastic), a rubber, a polyurethane, a silicone, and/or any other suitable material or combination of materials. Also, in some examples, the front support 156 incorporates one or more individual electrodes (e.g., reference electrodes) positioned to receive signals from the frontal area of the head. In some examples, a clip structure may be used to attach the electrodes to the front of the head. An example electrode clip is disclosed in U.S. patent application Ser. No. 13/829,849, mentioned above and incorporated herein by reference in its entirety.

In the illustrated example, the headset 100 also includes a processing unit 170 that is removably coupled to the central support member 116 of the electrode assembly 102 (described in further detail below). In the illustrated example, the central support member 116 communicatively couples the electrodes of the electrode units 117 of the strips 106-114 to the processing unit 170. For example, the central support member 116 communicatively couples the electrodes of the example strips 106-114 to the processing unit 170 via communication links (e.g., wires, a ribbon, a flexible printed circuit board (FPCB), a printed circuit board (PCB)) running through the central support member 116 and/or the strips 106-114. In other examples, the strips 106-114 are wirelessly coupled to the processing unit 170 and/or a remote processor. For example, one or more of the strips 106-114 may include a transmitter to wirelessly transmit signals (e.g., EEG signals) to the processing unit 170. In such examples, the central support member 116 supports the strips 106-114 and provides rigidity and structure to the electrode assembly 102 but does not function to convey communication signals. In still other examples, the headset 100 does not include the processing unit 170, and the signals are communicated to a handheld or other remote receiver.

In the illustrated example, the processing unit 170 has a housing that includes the electrical components for conditioning and/or processing signals gathered from the electrodes (described in further detail below). In some examples, the electrical components include circuitry (e.g., filter, amplifier, digital-to-analog converter(s), processor(s)) to, for example, convert the EEG data from analog data to digital data, amplify the EEG data, remove noise from the data, analyze the data, and transmit the data to a processor, computer, and/or other remote receiver or processing unit. In some examples, the processing unit 170 includes hardware and software such as, for example, an amplifier, a signal conditioner, a data processor and/or a transmitter for transmitting signals to a data center, processor, and/or a computer. In other examples, some of the processing occurs at the headset 100 and some processing occurs remotely after the headset 100 transmits data or semi-processed results to a remote site such as, for example, via a wireless connection. In some examples, the processing unit 170 is removably attached to the headset 100. In some such examples, the processing unit 170 may be removed and replaced with a different processing unit that may have, for example, different programming functions and/or analysis tools. In some examples, a plurality of processing units may contain different preprogrammed analysis tools and the processing units may be interchanged depending on the desired function (e.g., controlling entertainment such as a game or gathering data for a medical diagnosis) of the headset 100.

As shown in FIGS. 1A and 1B, the processing unit 170 of the illustrated example also includes electromechanical receivers 172, 174, which may be used, for example, to physically and electrically connect terminals of additional electrodes or sensors to the processing unit 170. In some examples, the electromechanical receivers 172, 174 are used for attaching other electrodes or physiological/biological measurement devices (e.g., an EKG sensor, an eye tracking sensor, etc.). The additional devices may include terminals having mating electromechanical connectors or terminals (e.g., apertures and pins, connection points) that may be attached to the processing unit 170 and/or to other terminals attached to the processing unit 170. In some examples, an electrode is used as a reference or ground electrode to provide a reference signal for comparing with the EEG signals gathered from other parts of the head by, for example, the headset 100 shown in FIGS. 1A-1E. A reference or ground electrode is positioned at a point on the body (e.g., an ear or nose) that has little (e.g., minimal) or no EEG activity or other artifacts and/or noise such as, for example, those indicative of muscle contractions or blood flow. In such an example, the ground electrode may include a terminal that connects to one of the receivers 172, 174 on the processing unit 170. An example terminal and receiver structure is disclosed in U.S. patent application Ser. No. 13/829,849, mentioned above and incorporated herein by reference in its entirety.

In use of the example headset 100 of FIGS. 1A-1E, the electrode assembly 102 is attached to the adjustment assembly 104 (e.g., via the tension straps 118-136 and adjustors 142-152) and the headset 100 is then placed on the head of a user. The processing unit 170 may be attached to the central support member 116 (described in further detail below) prior to or subsequent to placing the headset 100 on the head of a person. In other examples, the adjustment assembly 104 is placed on the head of a person (e.g., by stretching the first and second adjustment lines 158, 160 over the head of the user) and coupling the example electrode assembly 102 to the adjustment assembly 104 (e.g., by connecting the tension straps 118-136 to the respective adjustors 142-152).

The adjustors 142-152 of the illustrated example operate to change the tension (e.g., via the effective length) of the tension straps 118-136 and, thus, create more or less force in the strips 106-114 against the head of the user. For example, in the case of a smaller head, the example first adjustor 142 on the first support 138 and/or the example fourth adjustor 148 on the second support 140 may be used to create more tension in the first and second tension straps 118, 120 until the first strip 106 applies a desired amount of pressure against the head of the person. Additionally, the first and second rear adjustors 162, 164 operate to adjust to the position of the first and second supports 138, 140 to further adjust the headset 100 on the head of the user.

As mentioned above, in some examples, the adjustors 142-152 are removably attached to the first and second supports 138, 140. The removability of the adjustors 142-152 provides a safety function by enabling the example electrode assembly 102 to easily be disconnected from the adjustment assembly 104 if too much force is exerted on the electrode assembly 102. For example, if one of the strips 106-114 of the electrode assembly 102 is snagged or caught on a foreign object, one or more of the example adjustor(s) 142-152 release, and the example electrode assembly 102 disconnects or partially disconnects from the adjustment assembly 104.

Figure 2A:
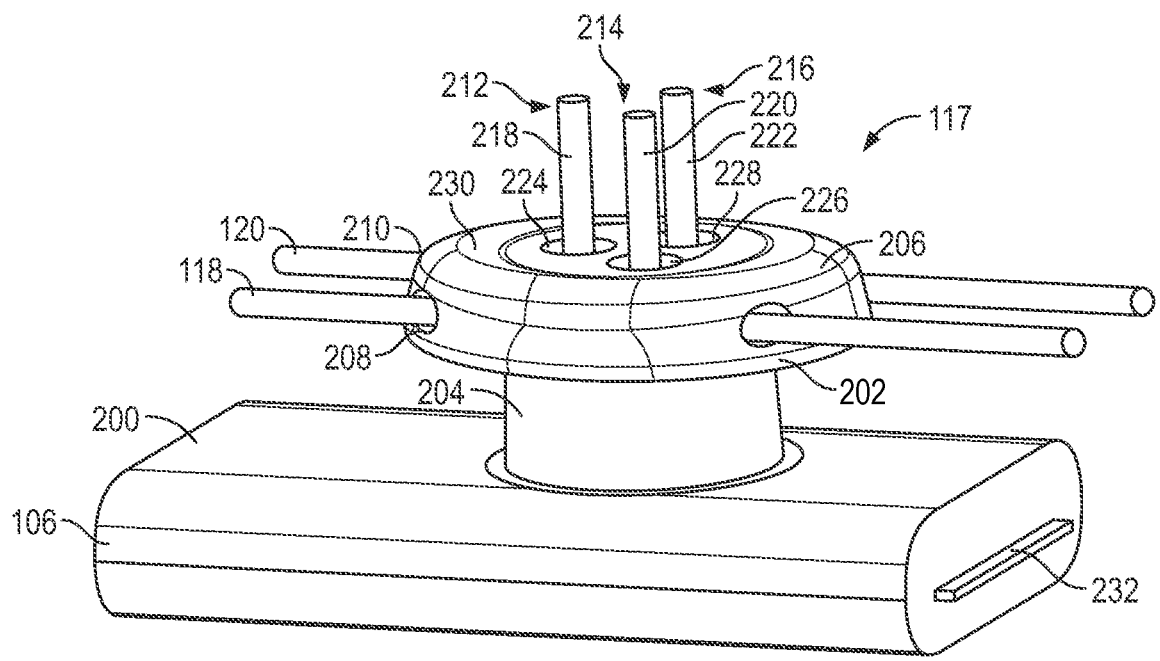
FIG. 2A is an enlarged view of an example electrode unit of the example electrode assembly of FIG. 1A showing example electrode pins in an extended position.
Figure 2B:
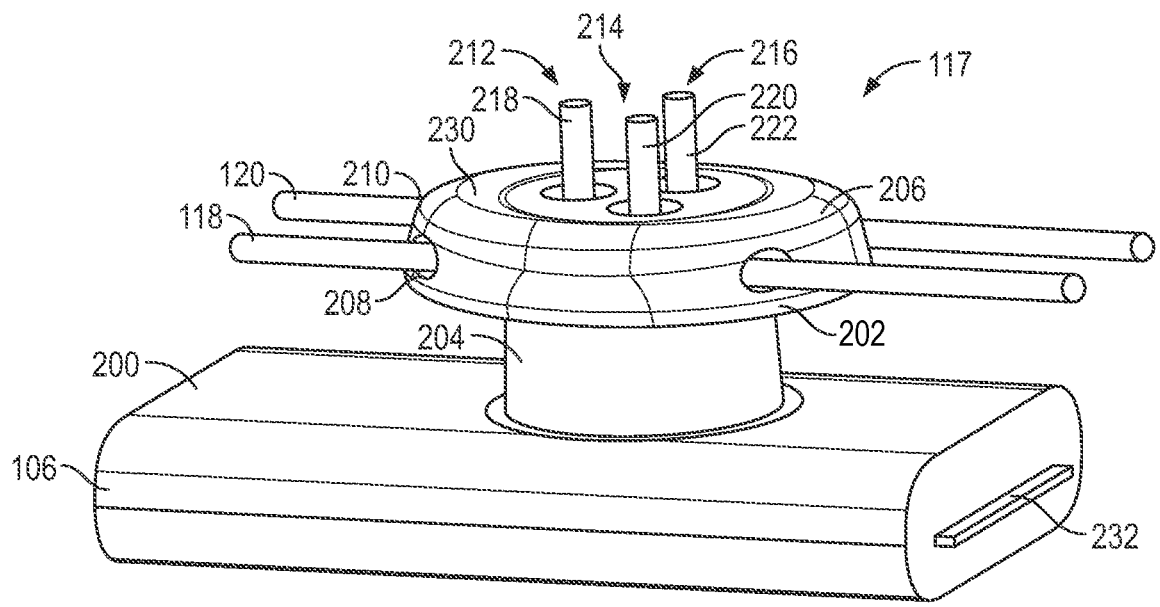
FIG. 2B is an enlarged view of the example electrode unit of FIG. 2A with the example electrode pins shown in a first retracted position.
Figure 2C:
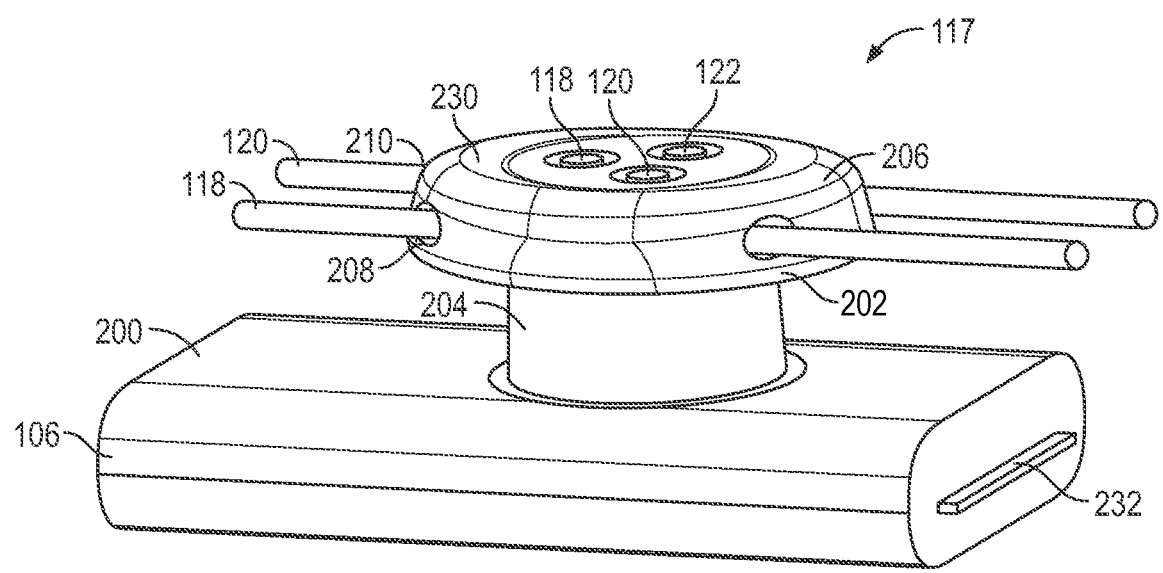
FIG. 2C is an enlarged view of the example electrode unit of FIG. 2A with the example electrode pins shown in a second retracted position.

FIGS. 2A-2C are enlarged views of a portion of the first strip 106 having an electrode unit 117. The illustrated view shows the bottom of the first strip facing upward. In use, the bottom of the first strip 106 would face the head of the user. Although only one electrode unit 117 of one strip 106 is shown and described here, this electrode unit 117 is similar to any or all of the other electrode units 117 coupled to the strips 106-114. The electrode unit 117 of the example of FIG. 2A extends from a bottom surface 200 of the first strip 106. In this example, the electrode unit 117 includes a housing 202 (e.g., a body) comprised of an extension member 204 and a contact member 206. The electrode unit 117 of the illustrated example includes three electrodes 212, 214, 216 extending from the contact member 206 to contact the scalp of the user to gather EEG signals from the brain. Other examples use fewer or more electrodes. The extension member 204 of the illustrated example separates the contact member 206 from the bottom surface 200 of the first strip 106. In other examples, no extension member is utilized and the contact member 206 is coupled directly to the first strip 106.

As shown in the illustrated example, the housing 202 of the electrode unit 117 includes a first channel 208 (e.g., a wire guide, a slot, a passage, an opening, an aperture, a hole, etc.) and a second channel 210 (on the opposite side of the electrode unit 117). The first channel 208 is to slidably receive the first tension strap 118 of the first strip 106, and the second channel 210 is to slidably receive the second tension strap 120 of the first strip 106. The first and second channels 208, 210 may be any shape and/or have any cross-section to enable the first and second tension straps 118, 120 to slide through the respective channels 208, 210. In the illustrated example, the first and second channels 208, 210 are substantially parallel. As the first and second tension straps 118, 120 of the first strip 106 are pulled toward the scalp (e.g., when the tension is increased by the adjustors 142, 148), the first and second tension straps 118, 120 pull the contact member 206 of the electrode unit 117 closer to the scalp of the user.

In the illustrated example, the electrode unit 117 includes three electrodes 212, 214, 216. However, in other examples, the electrode unit 117 may include more or fewer electrodes (e.g., one, two, ten, etc.). Also, in some examples, each of the electrode units 117 of the strips 106-114 may contain a different number of electrodes (e.g., a first electrode unit on the first strip 106 includes four electrodes and a first electrode unit on the second strip 108 includes two electrodes).

Figure 7A:
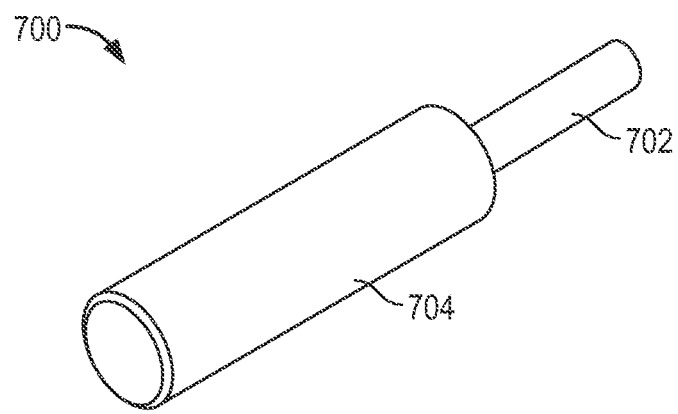
FIG. 7A is a perspective view of an example implementation of an electrode capable of use in the example of FIGS. 2A-2C and/or the example of FIGS. 5A-5D.

In the example shown in FIGS. 2A-2C, the first electrode 212 includes a first electrode pin 218 and a first body 224, the second electrode 214 includes a second electrode pin 220 and a second body 226, and the third electrode 216 includes a third electrode pin 222 and a third body 228. The electrode pins 218, 220, 222 are independently retractable relative to the respective body 224, 226, 228 (and, thus, independently movable relative to the housing 202). As shown in FIG. 7A, the first body 224 of the first electrode 212 is larger than the first electrode pin 218. The first electrode pin 218 is movable into and out of the end of the first body 224. In some examples, the electrodes 212, 214, 216 include springs disposed within the respective bodies 224, 226, 228 to bias the electrode pins 218, 220, 222 outward.

In the example shown in FIGS. 2A-2C, the bodies 224, 226, 228 of the respective electrodes 212, 214, 216 are disposed within the housing 202 of the electrode unit 117, and the electrode pins 218, 220, 222 extend from a bottom surface 230 of the contact member 206. The pins 218, 220, 222 of the illustrated example retract into the housing 202 as the ends of the pins engage the head of the user and are forced into the housing 202 as the contact member 206 moves toward the head of the user.

FIG. 2A illustrates an example in which the electrode pins 218, 220, 222 are fully extended such as, for example, when the electrode pins 218, 220, 222 are not engaged with the head of the user or are initially placed on the user's head. FIG. 2B illustrates an example in which the electrode pins 218, 220, 222 are partially retracted or pressed into the respective electrode bodies 224, 226, 228 in the housing 202. As the ends of the pins contact the head of the user, the springs provide a biasing force to extend the pins 218, 220, 222 outward and against the scalp, which assists in creating surface contact with the scalp of the user. FIG. 2C illustrates an example in which the electrodes pins 218, 220, 222 are completely retracted such as, for example, when the bottom surface 230 of the housing 202 is against the scalp of the user.

As shown in FIGS. 2A-2C, the bottom surface 230 of the contact member 206 is contoured or curved (e.g., concave). The contoured profile creates a more comfortable interface between the bottom surface 230 and the scalp of the user by conforming, generally (e.g., not necessarily exactly but close enough for comfort), to the curve of the head in those examples in which the respective strip is adjusted or tightened enough that the contact member 206 contacts the head. Also, in some examples, the distance between the first and second channels 208, 210 and the bottom surface 230 of the housing 202 is about two to about three millimeters to place the tension straps 118, 120 sufficiently away from the user's hair to reduce the potential for the tension straps 118, 120 to catch in the hair and cause discomfort (e.g., during removal of the headset).

As shown in FIGS. 2A-2C, a FPCB 232 is molded within the first strip 106. The FPCB 232 may include communication links (e.g., wires, traces, etc.) to transfer the signals gathered from the electrodes of the first strip 106. The electrodes 212, 214, 216 are communicatively coupled to the FPCB 232 (e.g., via electrical contact between the electrodes 212, 214, 216 and the FPCB 232 and/or one or more intermediate wires or conductive surfaces).

Figure 3A:
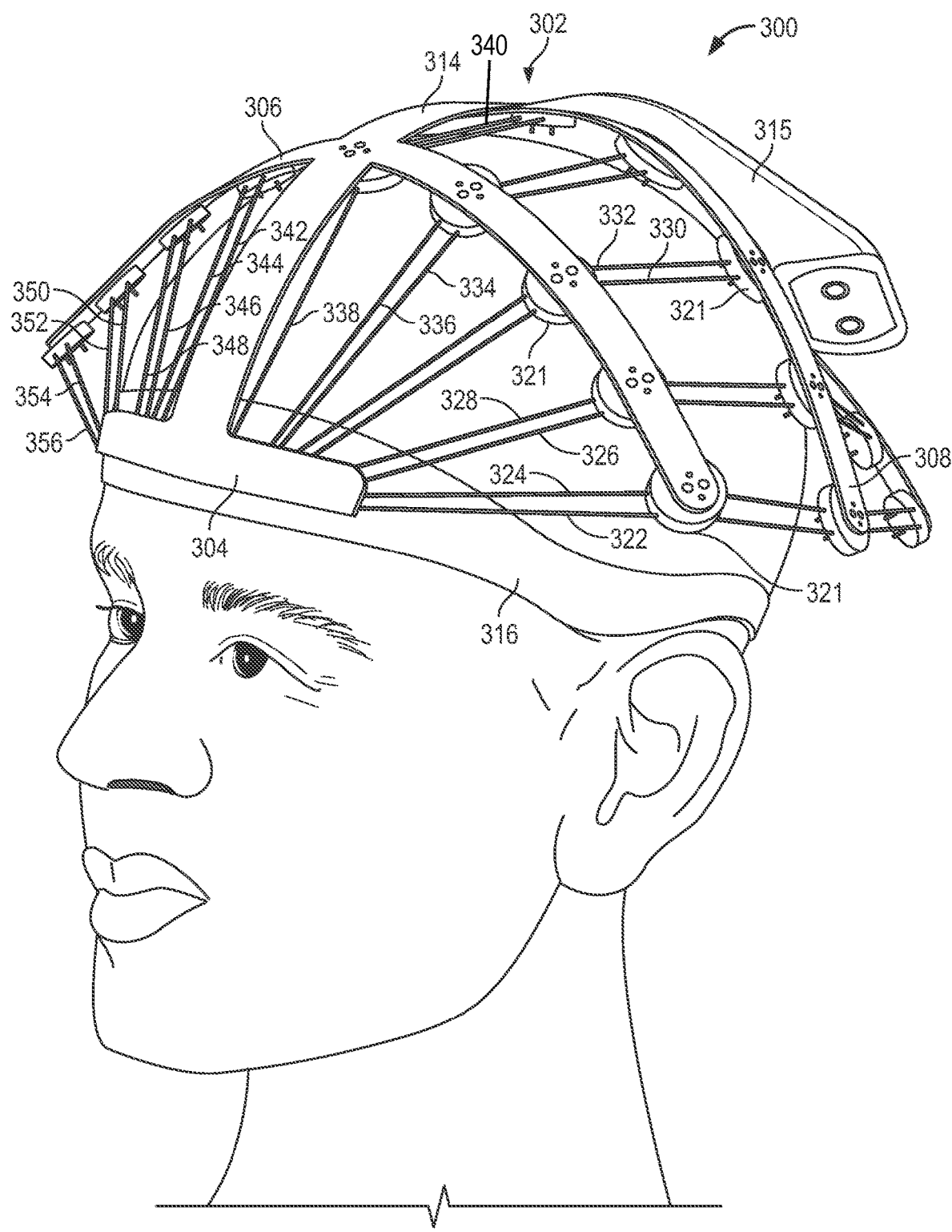
FIG. 3A is a front left perspective view of another example headset constructed in accordance with the teachings of this disclosure and including an example electrode assembly for gathering EEG signals.
Figure 3B:
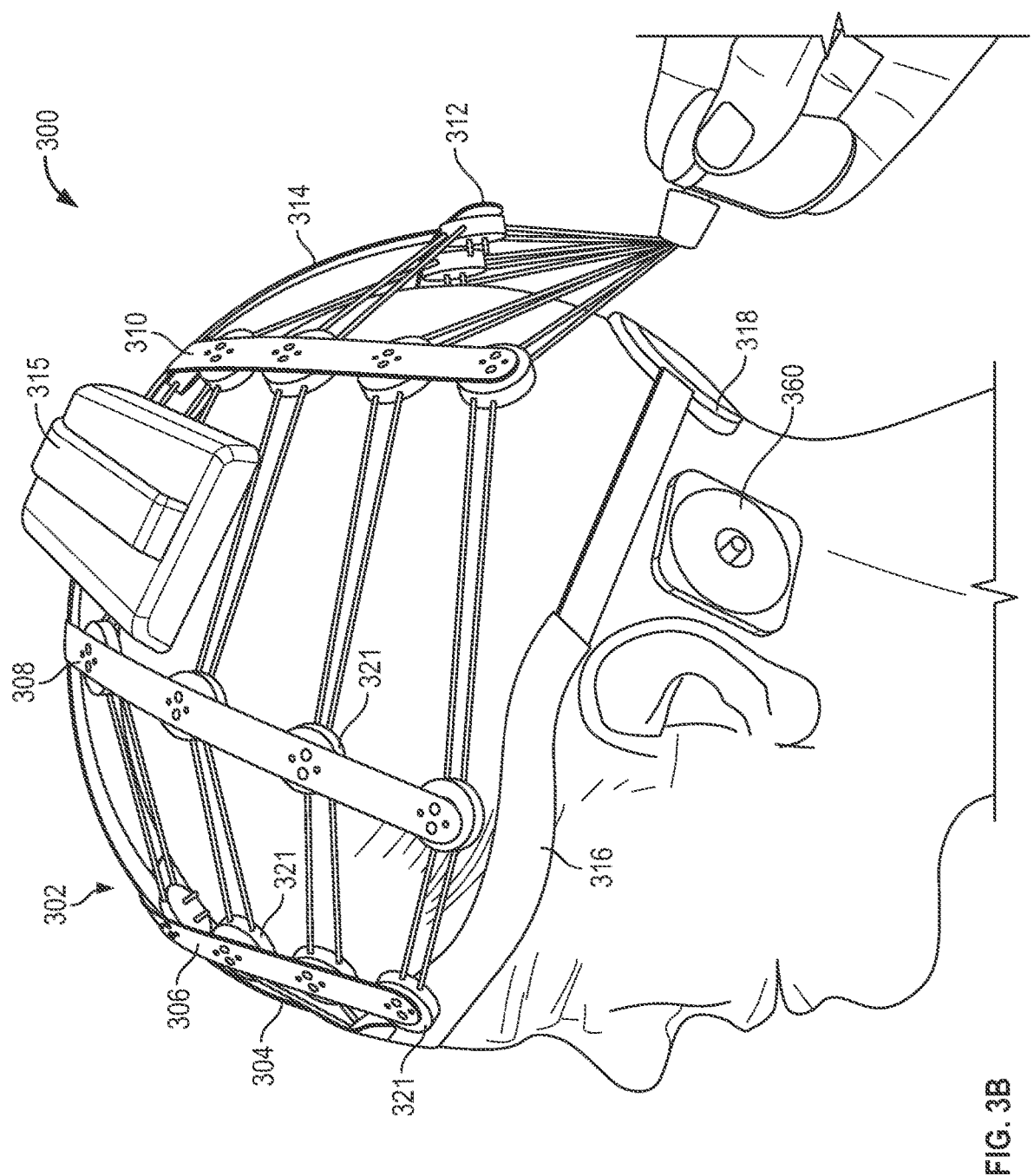
FIG. 3B is a side view of the example headset of FIG. 3A.
Figure 3C:
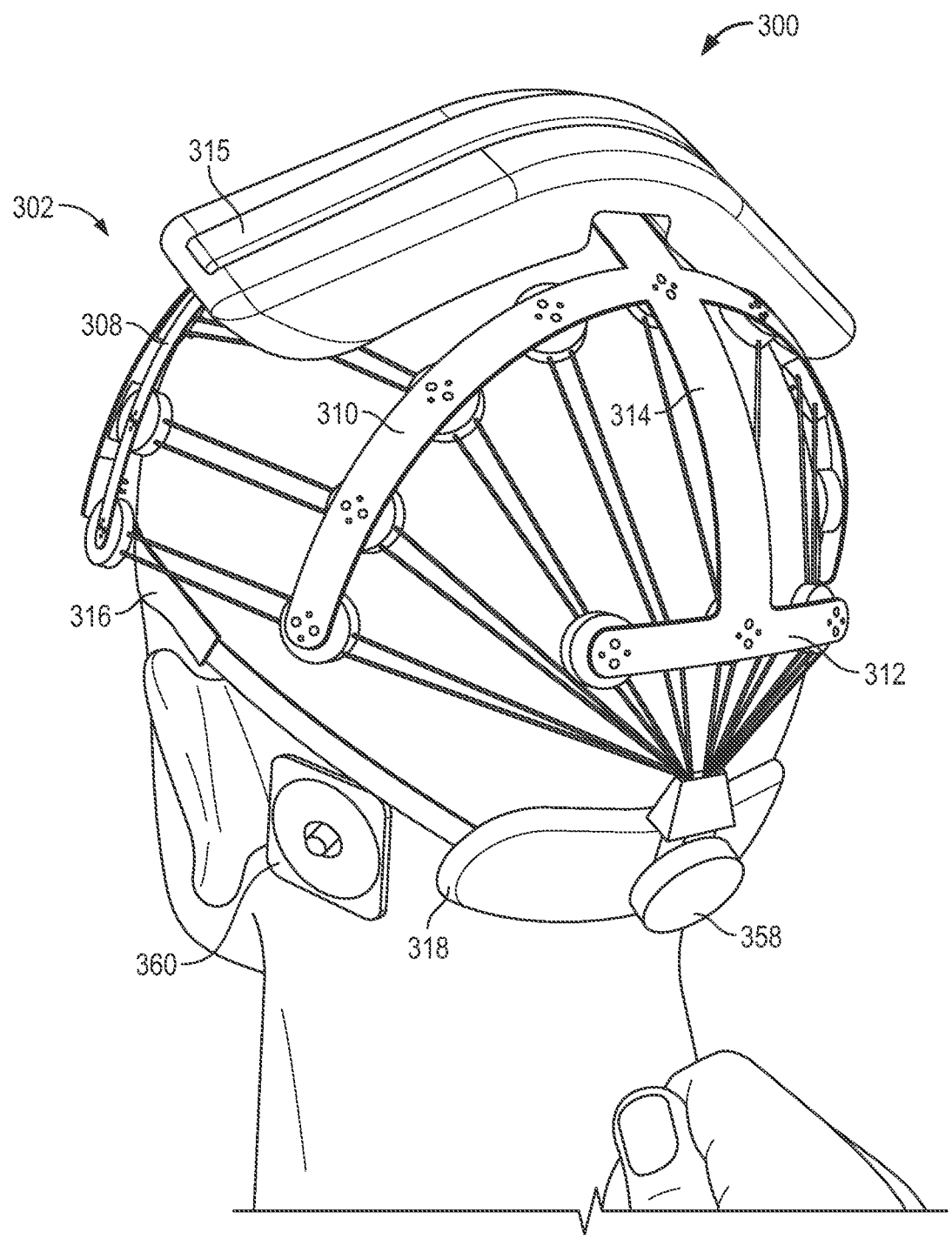
FIG. 3C is a left rear perspective view of the example headset of FIG. 3A.

FIGS. 3A-3C illustrate another example headset 300 for gathering EEG signals from the head of a person. FIGS. 3A and 3C are perspective views of the front and rear of the headset 300, respectively. FIG. 3B is a left side view of the example headset 300 on a head of a user or subject. Similar to the example headset 100 disclosed above, the example headset 300 of FIGS. 3A-3C includes an electrode assembly 302 (e.g., a sensor module) having a first strip 304, a second strip 306, a third strip 308, a fourth strip 310 and a fifth strip 312. Each of the strips 302-312 includes a plurality of electrodes, and each of the strips 302-312 is operatively coupled to a central support member 314 and a processing unit 315 is operatively coupled to the central support member 314 to receive, store, process and/or transmit the gathered EEG signals.

In the illustrated example shown in FIGS. 3A-3B, the electrode assembly 302 is worn on the head of a user such that the strips 304-312 are disposed over the head of the user from the left side of the head to the right side of the head and the central support member 314 is disposed over the head and extends from the back of the head to the front of the head (e.g., to the forehead). The strips 304-312 and the central support member 314 of the illustrated example are flexible and may conform to the shape of the head when flexed. The example strips 304-312 and the central support member 314 of the illustrated example are constructed of a flexible material such as, for example, a plastic (e.g., a thermoplastic), a rubber, a polyurethane, a silicone and/or any other suitable material or combination of materials.

As shown in the illustrated example of FIGS. 3A-3C, the headset 300 also includes a headband 316. In the illustrated example, the headband 316 is constructed of, for example, nylon or any other elastic material. In the example shown in FIG. 3A, the first strip 304 is operatively coupled to the headband 316 and the headband 316 surrounds the head. As shown in the example of FIGS. 3B and 3C, a base 318 is operatively coupled to the rear of the headband 316 and is to be disposed below the inion or occipital bone.

Figure 4:
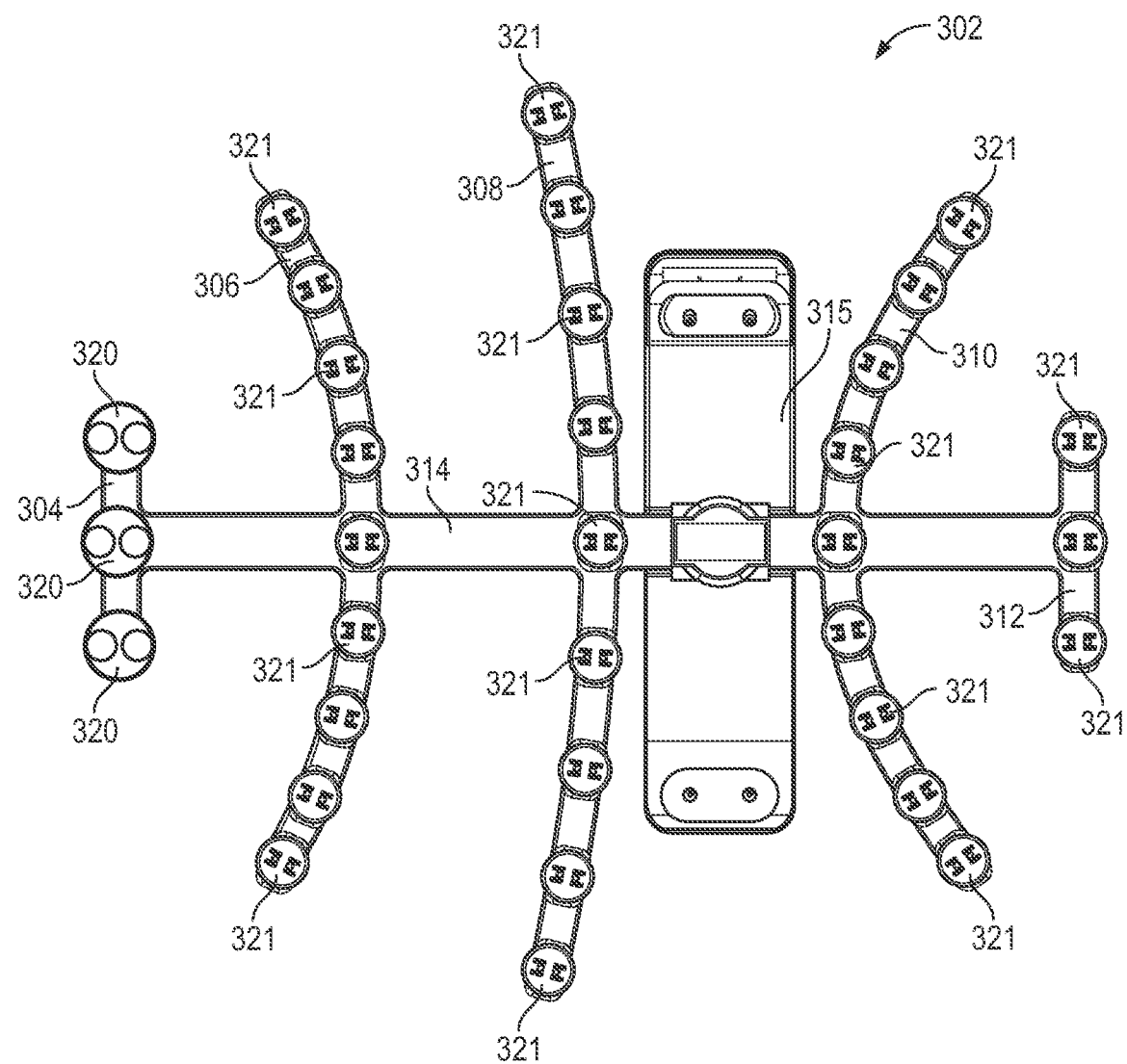
FIG. 4 is a bottom view of an example implementation of the example electrode assembly of the example headset shown in FIGS. 3A-3C.

As shown in FIGS. 3A-3C, each of the strips 304-312 of the illustrated example has a plurality of electrode units (e.g., electrode clusters) disposed on a bottom side of the respective strips 304-312. FIG. 4 illustrates a bottom view of the electrode assembly 302 of FIGS. 3A-3C. Specifically, in the illustrated example, the first strip 304 includes three electrode units 320, the second strip 306 includes nine electrode units 321, the third 308 strip includes nine electrode units 321, the fourth strip 310 includes nine electrodes 321, and the fifth strip 312 includes three electrodes 321. In total, the electrode assembly 302 of the illustrated example includes thirty-three electrode units. However, in other examples, the electrode assembly 302 may include more or fewer electrode units. Each of the electrode units 320, 321 includes one or more electrodes to engage the scalp of a user and receive EEG signals from the brain. In the example shown in FIG. 4, the electrode units 320 carried by the first strip 304 (discussed in FIG. 6) are different than the electrode units 321 carried by the second, third, fourth and fifth strips 306-312.

Unlike the headset 100 of FIGS. 1A-1E, where the tension straps 118-136 are disposed along the length or longitudinal axis of the respective strips 106-114, the example headset 300 of FIGS. 3A-3C utilizes tension straps 322-356 that are oriented substantially perpendicular to the strips 304-312 and that traverse from the front side of the head (e.g., at the first strip 304) to the back side of the head. Each of the electrode units 321 includes holes or wire guides for receiving the respective tension straps 322-356. Specifically, in this example, each of the electrode units 321 includes two holes or apertures to receive two of the tension straps 322-356. Similar to the headset 100 of FIGS. 1A-1E, the tension straps 322-356 may be pulled tight to move the electrode assembly 302 closer to the head of the person wearing the headset 300. The tension straps 322-356 may comprise wires, cords, lines, ties, straps, tethers, springs, belts, adjustment elements, and/or other suitable connecting elements. In some examples, the tension straps 322-356 comprise nylon. Additionally or alternatively, in some examples, the tension straps 322-356 are stretchable and comprise an elastic element.

In the example of FIGS. 3A-3C, each of the tension straps 322-356 is coupled to the first strip 304 and/or the headband 316 (e.g., a first support) on one end and operatively coupled to an adjustor 358 in the rear of the headset 300 at the opposite end. The adjustor 358 is removably coupled to the base 318 (e.g., a second support). The adjustor 358 is used to shorten the effective lengths of the tension straps 322-356. Specifically, as the tensions straps 322-356 are tightened, the electrode assembly 302 is pulled down and closer to the head of the person allowing the electrodes to move closer to the scalp.

As also shown in FIG. 4, the first strip 304 of the illustrated example includes three electrode units 320. Further, in the example, the second, third and fourth strips 306, 308, 310 each include nine electrode units 321. The fifth strip 312 includes three electrode units 321. The second, third and fourth strips 306, 308 310 of the illustrated example are curved to conform to the shape of the head.

As illustrated in FIGS. 3A-3C, the first and second tension straps 322, 324 are operatively coupled (e.g., indirectly or directly coupled) to the first strip 304 and/or the headband 316 at the front of the head. The first and second tension straps 322, 324 are slidably coupled to (1) a first one of the electrode units 321 on the second strip 306, (2) a first one of the electrode units 321 on the third strip 308, and (3) a first one of the electrode units 321 on the fourth strip 310. The first and second tension straps 322, 324 of the illustrated example are also operatively coupled to the adjustor 358 disposed in the rear of the headset 300. Thus, when tightened, the first and second tension straps 322, 324 of the illustrated example pull the first ones of the electrode units 321 on the second, third, and fourth strips 306, 308, 310 downward toward the left side of the head.

Similarly, the third and fourth tension straps 326, 328 of the illustrated example are operatively coupled to the first strip 304 and/or the headband 316, slidably coupled to a second one of the electrode units 321 on the second, third and fourth strips 306, 308, 310 and are operatively coupled to the adjustor 358 disposed in the rear of the headset 300. Thus, when tightened, the third and fourth tension straps 326, 328 pull the second ones of the electrode units 321 on the second, third, and fourth strips 306, 308, 310 downward toward the side of the head.

In the illustrated example, the fifth and sixth tension straps 330, 332 are operatively coupled to the first strip 304 and/or the headband 316, slidably coupled to a third one of the electrode units 321 on each of the second, third and fourth strips 306, 308, 310, slidably coupled to a first one of the electrodes 321 on the fifth strip 312 and are operatively coupled to the adjustor 358 disposed in the rear of the headset 300. In the illustrated example, the seventh and eighth tension straps 334, 336 are operatively coupled to the first strip 304 and/or the headband 316, slidably coupled to a fourth one of the electrode units 321 on each of the second, third and fourth strips 306, 308, 310, and are operatively coupled to the adjustor 358 disposed in the rear of the headset 300. In the illustrated example, the ninth and tenth tension straps 338, 340 are operatively coupled to the first strip 304 and/or the headband 316, slidably coupled to a fifth one of the electrode units 321 on each of the second, third and fourth strips 306, 308, 310, slidably coupled to a second one of the electrodes 321 on the fifth strip 312 and are operatively coupled to the adjustor 358 disposed in the rear of the headset 300. Also in the illustrated example, additional tension straps 342-356 are operatively coupled to the first strip 304 and/or the headband 316, additional ones of the plurality of electrode units 321 on the second, third, fourth and fifth strips 306, 308, 310, 312 and the adjustor 358 disposed in the rear of the headset 300. In other examples, the tension straps 322-356 may be arranged differently and may be operatively coupled and/or slidably coupled to different ones of the plurality of electrode units 320, 321 on different ones of the strips 304-312. Also, in some examples a single tension strap may be coupled to the respective electrode units 320, 321 such as, for example, along the center of the electrode units 321 between the front of the head and the adjustor 358.

In an example operation, the headband 316 is stretched over the head of a person and the electrode assembly 302 is placed on top of the head. FIGS. 3A and 3B illustrate the example headset 300 in an adjustment state, where strips 302-312 are being placed over the head of the person. The adjustor 358 is then connected to the base 318. In the illustrated example, the adjustor 358 comprises a wheel. As the wheel is rotated, the tensions straps 322-356 are wound around the wheel and, thus, the effective lengths of the tension straps 322-356 are shortened and the tension in the tension straps 322-356 pulls the strips 304-312 of the electrode assembly 302 against the head of the user. To loosen the headset 300, the adjustor 358 is rotated in the opposite direction. FIG. 3C illustrates the example headset 300 as it is being adjusted to move the strips 302-312 closer to the head of the person.

Figure 5A:
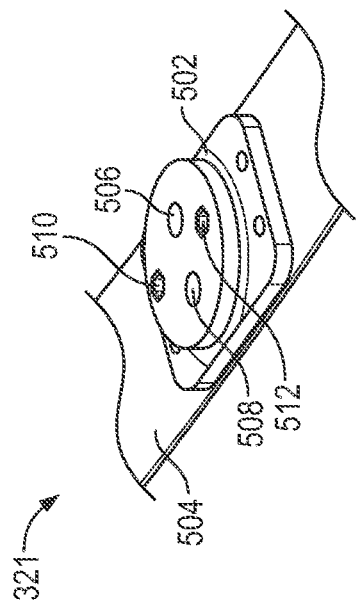
FIG. 5A is an enlarged view of an example flexible printed circuit board shown in the assembly of an example electrode strip of the example electrode assembly of FIG. 3A.

FIGS. 5A-5D are enlarged views of an example assembly of one of the electrode units 321 (shown on the headset 300 of FIGS. 3A-4). Specifically, FIG. 5A shows an example electrode unit 321. The example electrode unit of FIG. 5A may represent any of the electrode units 321 of the headset 300. The example electrode unit 321 includes an electrode housing 502 that is coupled to a FPCB 504. The FPCB 504 is disposed within the shell or body of the example strips 304-312. The housing 502 of the illustrated example includes two electrode openings 506, 508, to receive electrodes, and two peg openings 510, 512, which receive pegs from a bottom side of base (discussed in further detail below).

Figure 5B:
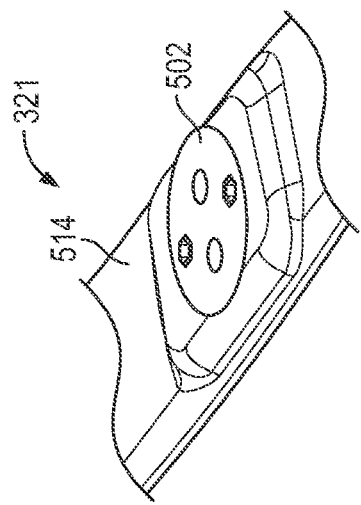
FIG. 5B is an enlarged view of the example electrode strip of FIG. 5A.
Figure 5C:
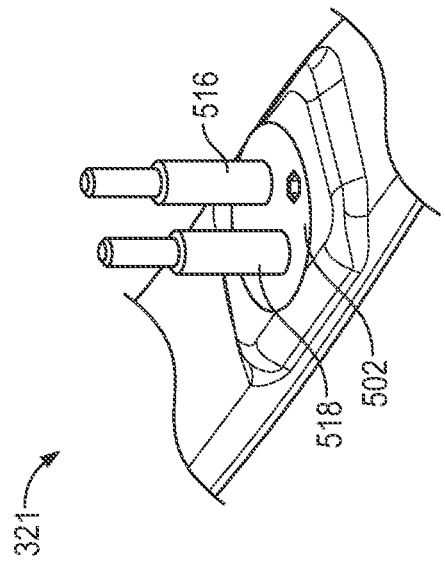
FIG. 5C is an enlarged view of the example electrode strip of FIG. 5B and shown with example electrodes.

FIG. 5B shows the electrode unit 321 with a casing or body 514 that covers the FPCB 504. The body 514 may be, for example, one of the strips 304-312. In some examples, the body 514 is molded over the FPCB 504. FIG. 5C shows a first electrode 516 and a second electrode 518 disposed in the respective first and second electrode openings 506, 508 of FIG. 5A. The first and second electrodes 516, 518 are communicatively coupled to the FPCB 504. In some examples, the first and second electrodes 516, 518 are secured in the respective first and second electrode openings 506, 508 via friction fit. In other examples, other suitable fastening techniques may be employed. Also, in some examples, the electrodes 516, 518 are removably coupled to the housing 502. In such examples, a damaged or otherwise inoperable electrode may be easily replaced. In the illustrated example, the electrode unit 321 includes two electrodes. However, in other examples, the electrode unit 321 includes more or fewer than two electrodes. In some examples, each of the electrode units 321 include the same amount of electrodes. In other examples, the amount of electrodes per electrode unit is different.

Figure 5D:
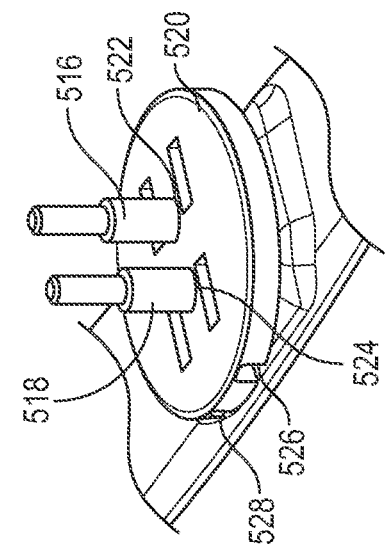
FIG. 5D is an enlarged view of the example electrode strip of FIG. 5B and shown with example wire guides.

FIG. 5D shows an example base 520 disposed on top of the housing 502 of FIG. 5A. The base 520 of the illustrated example is a circular disk with two pegs protruding from the bottom of the base 520 that mate with the first and second peg openings 510, 512. The example base 520 also includes two holes 522, 524 where the respective first and second electrodes 516, 518 are received. In the example of FIGS. 5D, the first and second electrodes 516, 518 extend through the respective first and second holes 522, 524. As shown in FIG. 5D, the base 520 also includes two apertures 526, 528 to receive tension straps (e.g., the tension straps 322-356). The apertures 526, 528 of the illustrated example extend from a first end of the base 520 to the opposite end of the base 520. As the tension straps are tightened, the electrode unit 320 is pulled closer to the head of the user to enable the electrodes 516, 518 to engage the scalp.

In the example headset 300 of FIGS. 3A-5D, the apertures 526, 528, which are to receive the tension straps 322-356, are positioned substantially orthogonal to longitudinal axes of the strips 304-312. In the example headset 100 of FIGS. 1A-2C, the apertures or channels 208, 210 are positioned substantially parallel to or along the longitudinal axes of the strips 106-114.

Figure 6:
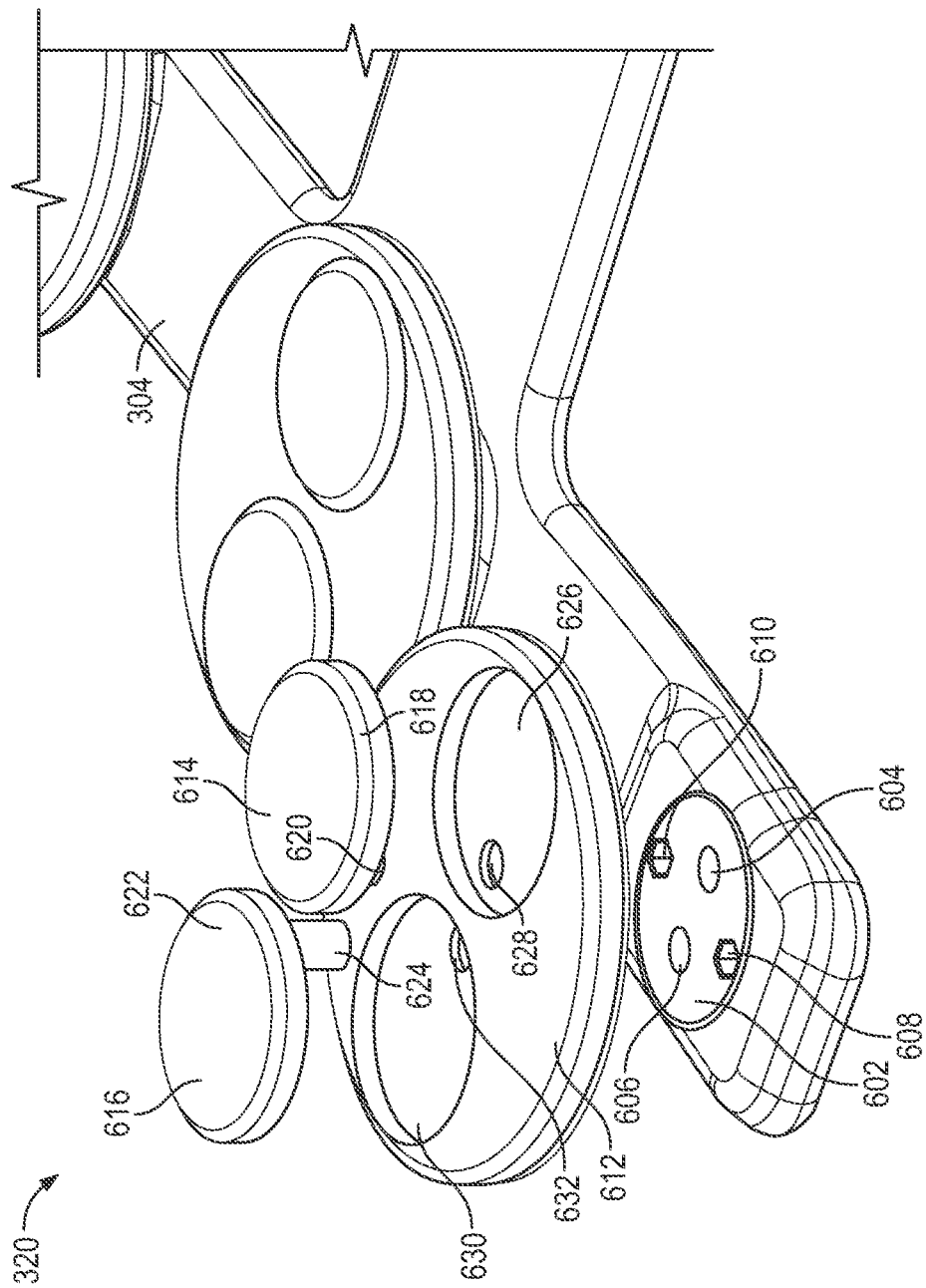
FIG. 6 is an exploded view of another example implementation of the example electrode strip of the electrode assembly of FIGS. 3A-3C.

FIG. 6 is an exploded view of an example assembly of one of the electrode units 320 of the first strip 304 of the headset 300. The example electrode unit 320 of FIG. 6 may represent any of the electrode units 320 of the headset 300. The first strip 304 of this example is to be disposed on the forehead of the user and uses flat electrodes to engage the forehead of the user, rather than a pointed or pin electrode, which are used to penetrate through hair. The forehead generally lacks hair and, thus, flat electrodes may be used to receive signals from the front part of the head more comfortably than pointed electrodes.

In some examples, the electrode units 320, which include relatively flatter electrodes, are used as ground electrodes. In some known systems, a ground electrode is attached to a place on the user's body using a gel, which reduces the amount of impedance. In these known systems, the forehead is typically avoided, because undesired signals (e.g., from eye movement) and other brain signals may be detected at the forehead and, therefore, would be difficult to implement as a ground signal. However, the forehead contains relatively lower impedance than other places on the body. Therefore, the example headset 300 disposes dry electrodes, which are easier and cleaner to use, on the forehead of the user as ground electrodes. To avoid problems of undesired signals in the ground signals detected by the forehead electrodes, the difference between a reference signal and a data signal (e.g., gathered by an electrode on the head of the user, by an electrode of one of the electrode units 321) is subtracted from the difference between the ground signal and the data signal. Thus, the ground signals, including any detected undesired signals, are cancelled out, or eliminated, and the remaining difference is the difference between the data signal and the reference electrode (e.g., known as "referencing"). The reference electrode may be attached, for example, to an earlobe or a nose of the user. An example clip that may be utilized to attach a reference electrode to a user's earlobe is disclosed in U.S. patent application Ser. No. 13/829,849 titled "METHODS AND APPARATUS TO GATHER AND ANALYZE ELECTROENCEPHALO-GRAPHIC DATA," filed Mar. 14, 2013, which is incorporated herein by reference in its entirety. Additionally or alternatively, the ground or reference electrode may be disposed on the neck of the person. An example patch electrode 360 is shown in FIG. 3B attached to the neck of the person. A wire or lead may be connected to the electrode 360 and connected to the processing unit 315.

In the illustrated example of FIG. 6, the electrode unit 320 includes a housing 602, which is similar to the housing 502 shown in FIGS. 5A-5D above. The housing 602 of the illustrated example includes a first electrode opening 604, a second electrode slot 606, a first peg hole 608 and a second peg hole 610. In the example of FIG. 6, a base 612 is couplable to the housing 602. The base 612 includes two pegs on the bottom to engage the peg holes 608, 610. A first electrode 614 and a second electrode 616 are shown in the example of FIG. 6. The first electrode 614 includes a first contact 618 and a first electrode peg 620 and the second electrode 616 includes a second contact 622 and a second electrode peg 624. The first contact 618 of the illustrated example sits within a first cavity 626 in the base 612, and the first electrode peg 620 extends through a first electrode peg hole 628 in the base 612 to engage the first electrode opening 604. Likewise, the second contact 622 sits within a second cavity 630 in the base 612, and the second electrode peg 624 extends through a second electrode peg hole 632 in the base 612 to engage the second electrode opening 606. Signals received by the first and second contacts 618, 622 are transmitted through the respective first and second electrode pegs 620, 624 to the FPCB 504 (which is disposed within the body of the strip 304). In some examples, the electrode unit 320 may be used on any one of the second, third, fourth and fifth strips 306-312 and may include apertures to accommodate tension straps. In some examples, the electrode unit 321 of FIGS. 5A-5C may be used on the first strip 304.

Figures 7B, 7C:
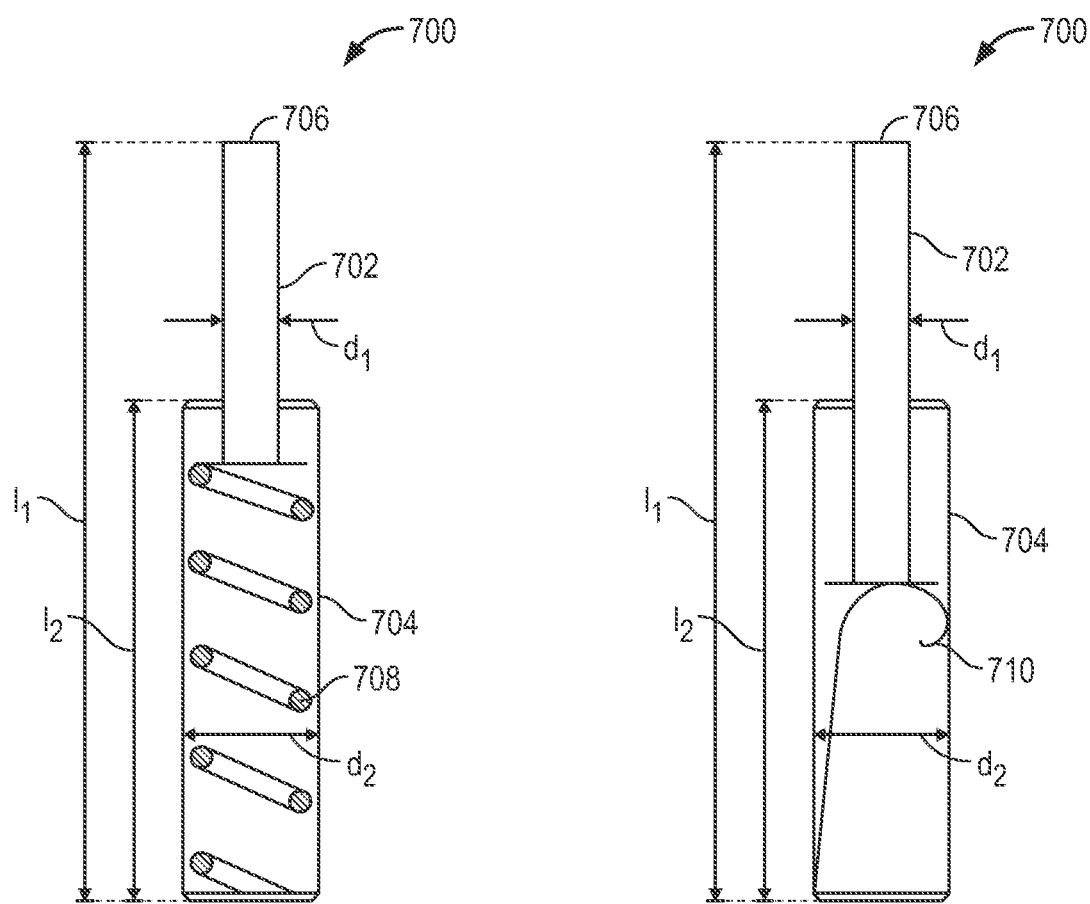
FIG. 7B is a cross-sectional view of a first example implementation of the example electrode of FIG. 7A.
FIG. 7C is a cross-sectional view of a second example implementation of the example electrode of FIG. 7A.

FIGS. 7A-7C illustrate an example electrode 700 that may be used, for example, with the example headset 100 (e.g., to implement the electrodes 212, 214, 216 shown in FIGS. 2A-2C) and/or the example headset 300 (e.g., to implement the electrodes 516, 518 shown in FIGS. 5C-5D) described above. As shown in the example in FIGS. 7A-C, the example electrode 700 includes a pin 702 and a body 704 (e.g., a sheath, a tube, a cover, a housing, etc.). In the illustrated example, the pin 702 and the body 704 are cylindrical and have circular cross-sections. However, in other examples, the electrode pin 702 and/or the body 704 may have a rectangular, square or otherwise shaped cross-section. In the illustrated example, an end 706 of the pin 702 is flat, which provides a larger surface area to contact the scalp of the user. The larger surface area also increases the comfort level of the pin 702 on the head by spacing the applied force across a larger area. However, in other examples, the end 706 of the pin 702 may be rounded, hooked shaped, ring shaped, or otherwise shaped.

FIGS. 7B and 7C are cross-sectional views of the electrode 700. As shown, the pin 702 has a diameter $d_1$. In some examples, $d_1$ is about (e.g., within +/−0.04 millimeters) 0.80 millimeters. In other examples, the pin 702 may have a smaller or larger diameter. The electrode pins are sized to protrude through the hair of a user, but also provide sufficient surface area to contact the scalp of the user and receive signals from the brain. In some examples, the electrode 700 is made of a metallic material and/or coated (e.g., anodized or plated) with a metallic material (e.g., silver, gold, etc.). In some examples, if the coating is too thin, the electrode will not be able to effectively detect the ion flow. Therefore, in some examples, the pin 702 is coated with a metallic material greater than about (e.g., within +/−0.1 microns) 5 microns thick. In other examples, the coating may have a larger thickness (e.g., about 80 microns).

In the illustrated example shown, the body 704 has a diameter $d_2$. In some examples, $d_2$ is about (e.g., +/−0.5 millimeters) 2 millimeters. In the illustrated example, the electrode 700 has an overall length of $l_1$ and the body 704 has a length of $l_2$. In some examples, $l_1$ is about (e.g., +/−0.5 millimeters) 11.2 millimeters and $l_2$ is about (e.g., +/−1.0 millimeters) 7.4 millimeters, such that the pin 702 is about (e.g., +/−1.0 millimeters) 3.8 millimeters. However, in other examples, the dimensions $d_1$, $d_2$, $l_1$, $l_2$ may have other suitable values.

In the example shown in FIG. 7B, the electrode 700 comprises a pogo pin that includes a coil spring 708. The spring 708 of the illustrated example provides a biasing force to extend the pin 702 outward from the body 704 and against the scalp of the user. Different size springs may be utilized with the electrode 700 to provide more or less force. In some examples, the springs or biasing members provide around 2 Newtons of force.

In the example shown in FIG. 7C, the electrode 700 comprises a leaf spring 710. The leaf spring 710 provides a biasing force to extend the pin 702 outward from the body 704 and against the scalp of the user. Different strength leaf springs may be utilized with the electrode 700 to provide more or less force.

Figure 8A:
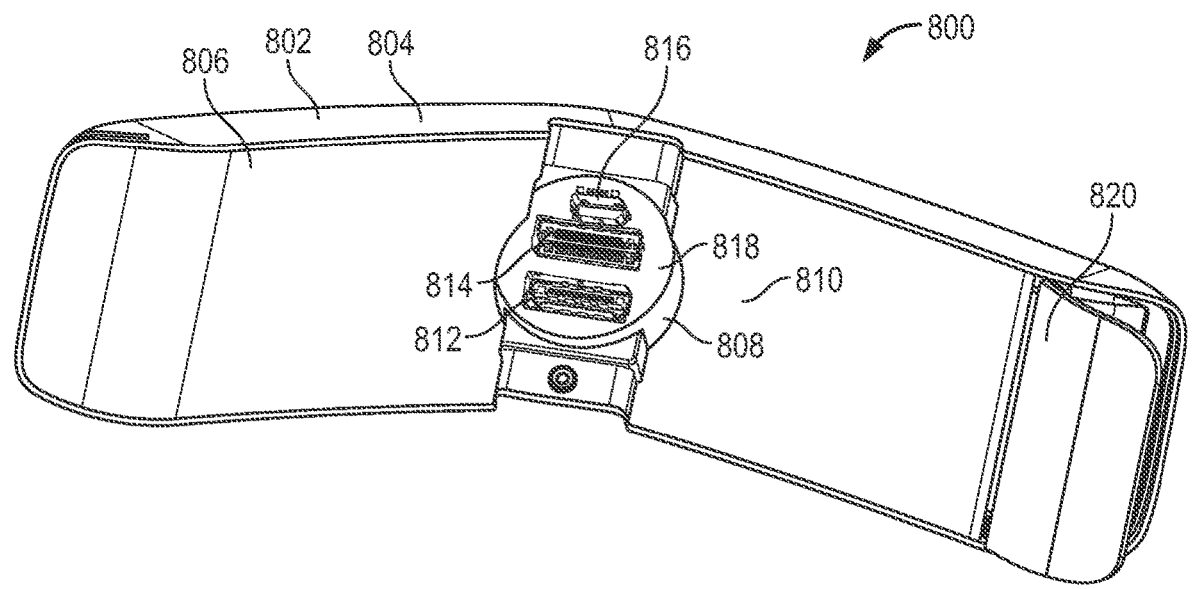
FIG. 8A is a perspective view of an example processing unit for use with the example headsets shown in FIGS. 1A and 3A.

FIG. 8A shows an example processing unit 800 (e.g., a computer module, an electronics module) that may be used with any of the example headsets 100, 300 described above. The example processing unit may be, for example, the processing unit 170 of the headset 100 or the processing unit 315 of the headset 300. The processing unit 800 is described herein in combination with the headset 100. However, it is to be understood that the processing unit 800 may similarly be unitized with the headset 300 and/or any other headset.

The processing unit 800 may be removably coupled to a headset such as, for example, the headset 100 described above (e.g., see FIGS. 1A-1E). The processing unit 800 of the illustrated example includes electronic components for receiving, storing and/or processing the EEG signals gathered by electrodes (e.g., from the electrode units 117 of the strips 106-114). The processing unit 800, which includes many electronic components, may be removed from the electrode assembly 102 so that the electrode assembly 102 and adjustment assembly 104 can be cleaned (e.g., sterilized, washed, disinfected) without harming the electronic components of the processing unit 800. For example, the electrode assembly 102 may be used multiple times and by multiple users and cleaning the electrode assembly 102 and adjustment assembly 104 reduces (e.g., minimizes) the risk of transferring bacteria, viruses, infections, etc. Additionally, if the electrode assembly breaks or becomes otherwise inoperable (e.g., when a number of electrodes malfunction), the processing unit 800 may be disconnected and attached to a new electrode assembly and, thus, reduces (e.g., minimizes) the cost of replacing the headset. The same processing unit can be easily disconnected from one electrode assembly (e.g., in a first size) and attached to another electrode assembly (e.g., in a second size). Further, the processing unit may be easily disconnected from the electrode assembly 102 and plugged into a computer to download and/or analyze the data stored in the processing unit 800.

As shown in FIG. 8A, the processing unit 800 of the illustrated example is defined by a housing 802 (e.g., a shell, a casing, a cover, a protective surface, etc.), which includes a top cover 804 and a bottom plate 806 that are operatively coupled together (e.g., via screws, adhesives, a snap fit and/or any other suitable mechanical or chemical fastener) to form the housing 802. In the illustrated example, the processing unit 800 is rectangular shaped and has a bend or arc formed in the middle. The arc shaped housing 802 allows the processing unit 800 to remain close to the top of the head of a subject when connected to the electrode assembly 102. However, in other examples, the housing 802 of the processing unit may be other shapes.

The bottom plate 806 of the processing unit 800 of the illustrated example has an opening 808 that exposes a connection hub 810. The connection hub 810 includes electrical connectors that are communicatively coupled to the electronic circuitry contained within the housing 802. Specifically, the connection hub 810 has a first electrical connector 812, a second electrical connector 814 and third electrical connector 816 coupled to a circuit board 818 disposed within the housing 802. In the illustrated example, the first and second electrical connectors 812, 814 are forty-pin connectors (e.g., board-to-board connectors, mezzanine connectors, edge type connectors, ribbon connectors, high density precise connectors, etc.). However, in other examples, the first and second electrical connectors 812, 814 may be any other type(s) and/or number of connectors suitable to transmit electrical signals. The first and second connectors 812, 814 are used to connect to the electrode assembly 102 and receive signals from the electrodes (e.g., from the electrode units 117). In the illustrated example, the first and second connectors 812, 814 each have forty (40) pins, which correspond to forty signals or channels (e.g., one for each electrode). Thus, a total of eighty (80) signals can be transmitted at one time. However, in other examples, other types of connectors having a different amount of pins may be used.

The third connector 816 of the illustrated example is a universal serial bus (USB) type connector and is used for charging the battery and updating firmware and/or software. The third connector 816 of the illustrate example may be connected to an outside computer or processing station and new software may be uploaded to the processing unit 800.

Figure 8B:
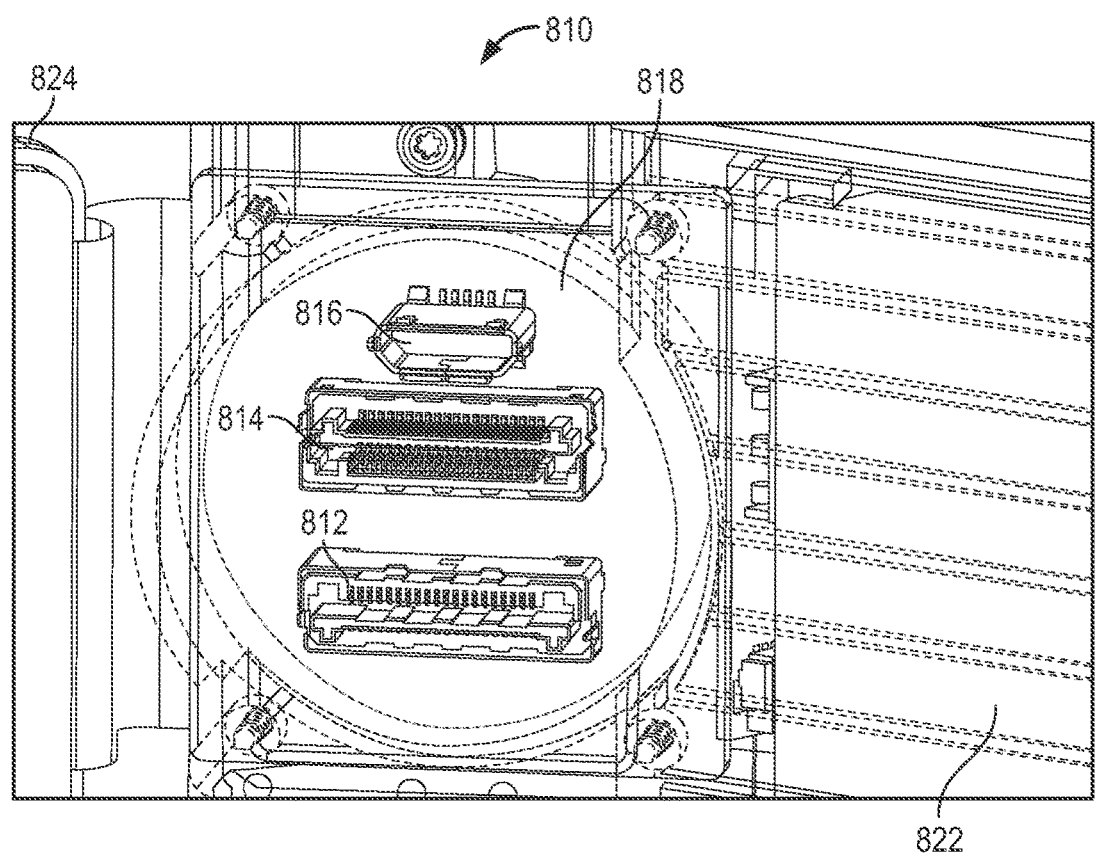
FIG. 8B is an enlarged view of an example connection hub of the example processing unit of FIG. 8A.

In the example of FIGS. 8A-8B, the connection hub 810 is located substantially in the middle of the housing 802 and centered at the bend. However, in other examples, the connection hub 810 and the first, second and third electrical connectors 812-816 may be located elsewhere on the housing 802. An enlarged view of the connection hub 810 is shown in FIG. 8B, where the bottom plate 806 is shown in dashed lines to expose the interior of the processing unit 800.

As shown in FIG. 8A, the bottom plate 806 of the housing 802 of the example includes a door 820 near one end of the housing 802. The door 820 opens to expose the interior of the processing unit 800. For illustrative purposes, the door 820 is shown in an open position. The processing unit 800 includes a semiconductor based processor 822 (e.g., a microprocessor) and a battery 824 (e.g., a battery pack, a lithium battery, etc.). A portion of the processor 822 and a portion of the battery 824 are shown in FIG. 8B. The processor 822 of the illustrated example is disposed in one side of the housing 802 and the battery 824 is disposed in the other side of the housing 802. The battery 824 is accessed through the door 820. In other words, the door 820 opens to allow the battery 824 to be removed or connected. The battery 824 may be removed, charged and replaced, or the battery 824 may be charged by plugging the third electrical connector 816 into a power source.

Figure 9A:
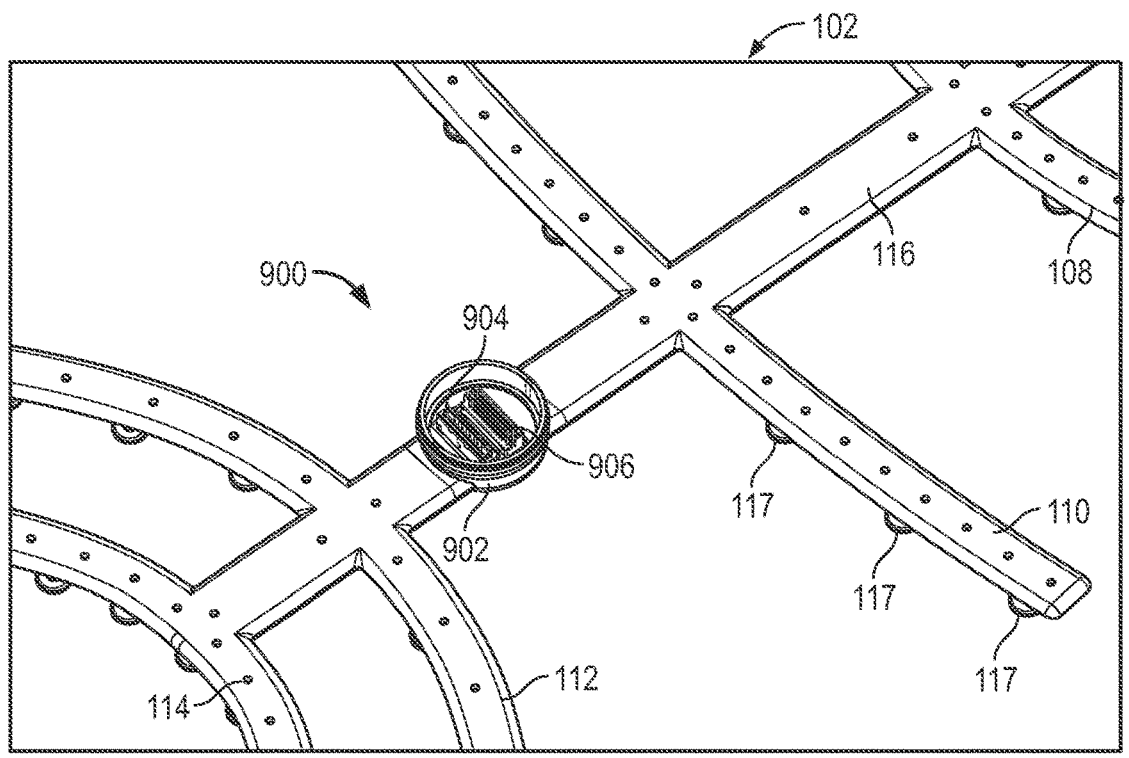
FIG. 9A is a perspective view of the example implementation of the example electrode assembly of FIG. 1A and having an example connection port.
Figure 9B:
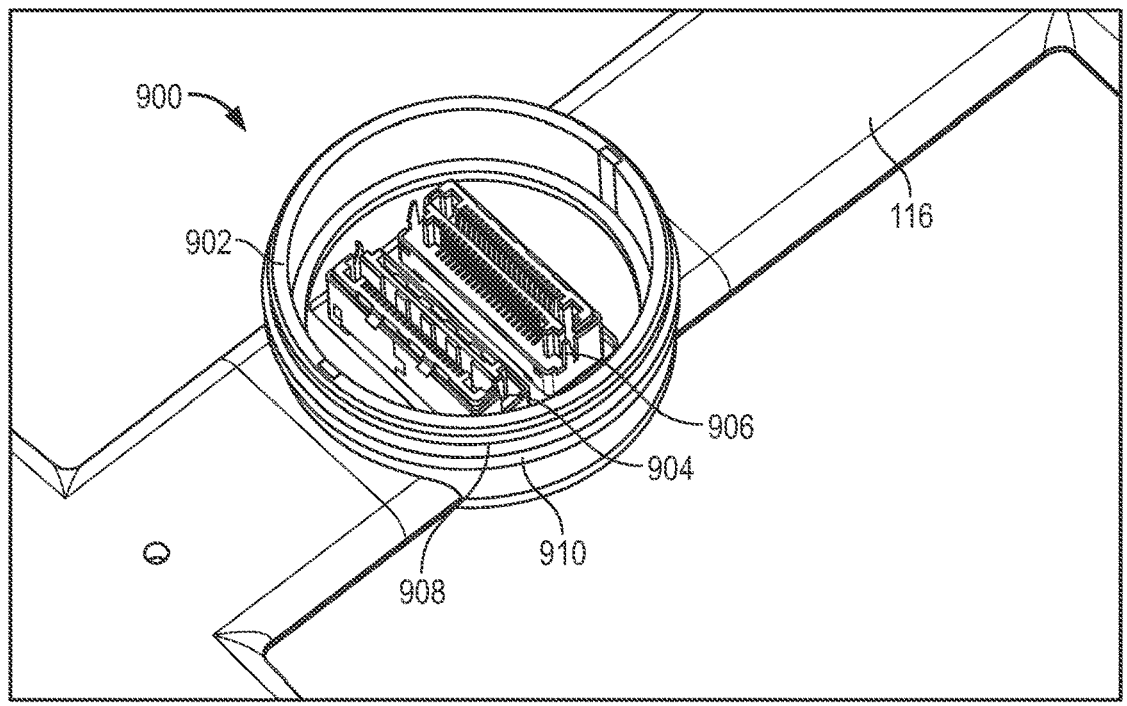
FIG. 9B is an enlarged view of the example connection port of FIG. 9A.

FIG. 9A shows an example connection port 900 operatively coupled to the central strip 116 of the electrode assembly 102 to provide a junction where the processing unit 800 may be removably coupled to the electrode assembly 102. FIG. 9B is an enlarged view of the connection port 900. As described above, the electrode assembly 102 of the illustrated example includes the first strip 106, the second strip 108, the third strip 110, the fourth strip 112 and the fifth strip 114 operatively coupled to the central strip 116. Each of the strips 106-114 includes a plurality of electrode units 117 to gather EEG signals along the scalp of a user.

The connection port 900 includes a cup 902 (e.g., having an annular rim), a fourth connector 904 and a fifth connector 906. The cup 902 corresponds substantially to the shape of the opening 808 formed in the bottom plate 806 of the processing unit 800, such that the connection hub 810 can slidably receive the cup 902 of the connection port 900. When the processing unit 800 is be coupled to the electrode assembly 102, the cup 902 is inserted in the opening 808 of the processing unit, the first connector 812 of the processing unit 800 mates with the fourth connector 904 and the second connector 814 of the processing unit 800 mates with the fifth connector 906.

As shown in the example of FIG. 9B, the connection port 900 includes a first retainer ring 908 and a second retainer ring 910 (e.g., o-rings) that are disposed around an outside surface of the cup 902. When the connection port 900 is inserted into the opening 808 of the connection hub 810 on the processing unit 800, the first and second retainer rings 908, 910 create friction between the outer surface of the cup 902 and the opening 808 of the processing unit 800 to help secure the processing unit 800 on the central strip 116.

As mentioned above, the electrode assembly 102 and adjustment assembly 104 of the illustrated example may be detached from the processing unit (e.g., the processing unit 170, the processing unit 800) and washed or cleaned to sterilize and/or sanitize the electrode assembly 102 and adjustment assembly 104. In some examples, a cap may be used to cover the connection portion 900 to prevent water and/or other wash solutions from seeping into the electrical connectors in the connection portion 900.

Figure 9C:
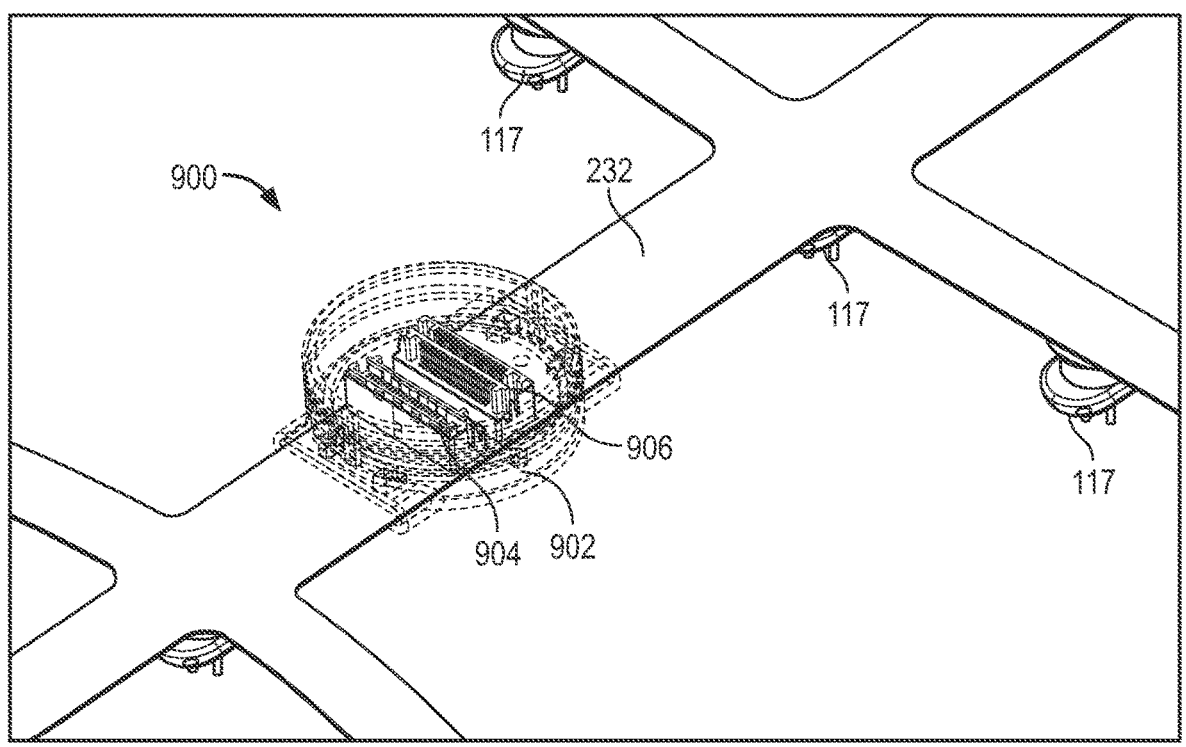
FIG. 9C is a perspective view of an example communication link of the example electrode assembly shown in FIG. 9A.

FIGS. 9C shows the fourth connector 904 and the fifth connector 906 coupled to the FPCB 232, which is disposed within the electrode assembly 102 of the illustrated example. The outer surfaces of the electrode assembly 102 of this example have been removed to show the FPCB 232. The connection port 900 is shown in dashed lines to expose the fourth connector 904 and the fifth connector 906. As shown, the FPCB 232 traverses through the electrode assembly 102 and couples the electrode units 117 to the connection port 900. The FPCB 232 of the illustrated example transfers the EEG signals from the electrode units 117 to the pins of the fourth and fifth connectors 904, 906 of connection port 900, thus allowing the fourth and fifth connectors 904, 906 to transfer the signals to the processing unit 800. In other examples, the FPCB 232 may be any communication link including wires or a ribbon connector to transfer the signals from the electrode units 117 through the electrode assembly 102 to the connection port 900.

Figure 10A:
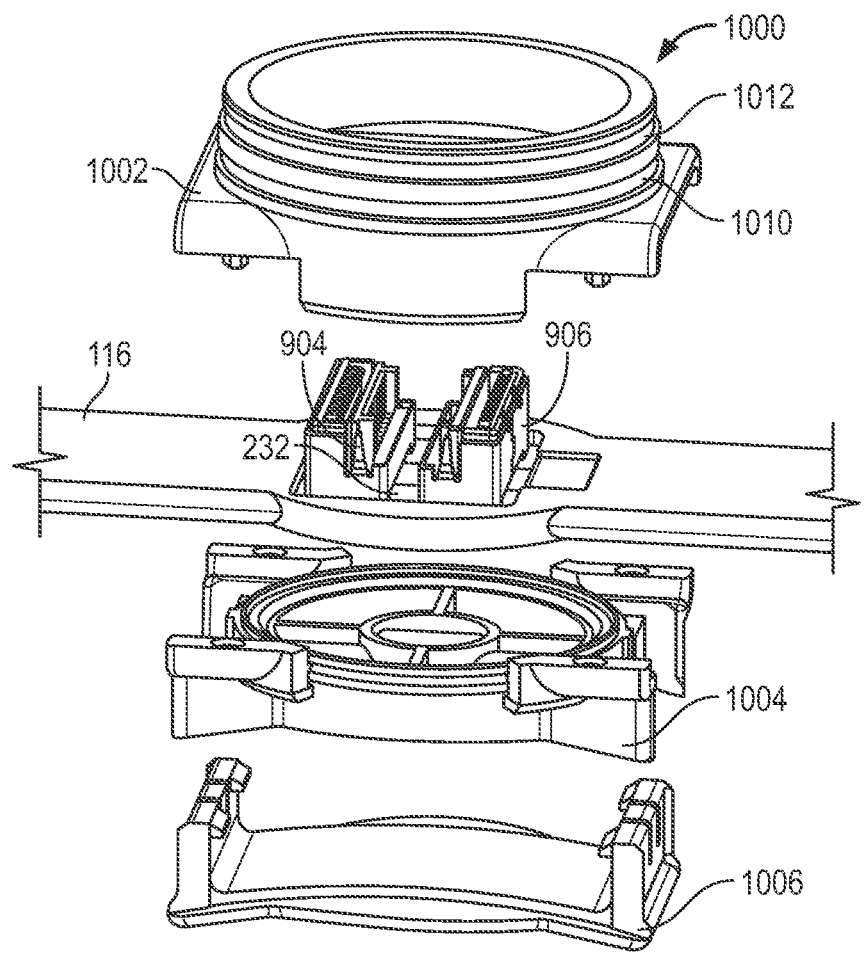
FIG. 10A is an exploded view of an example implementation of the example connection port of the example headset shown in FIG. 1A.
Figure 10B:
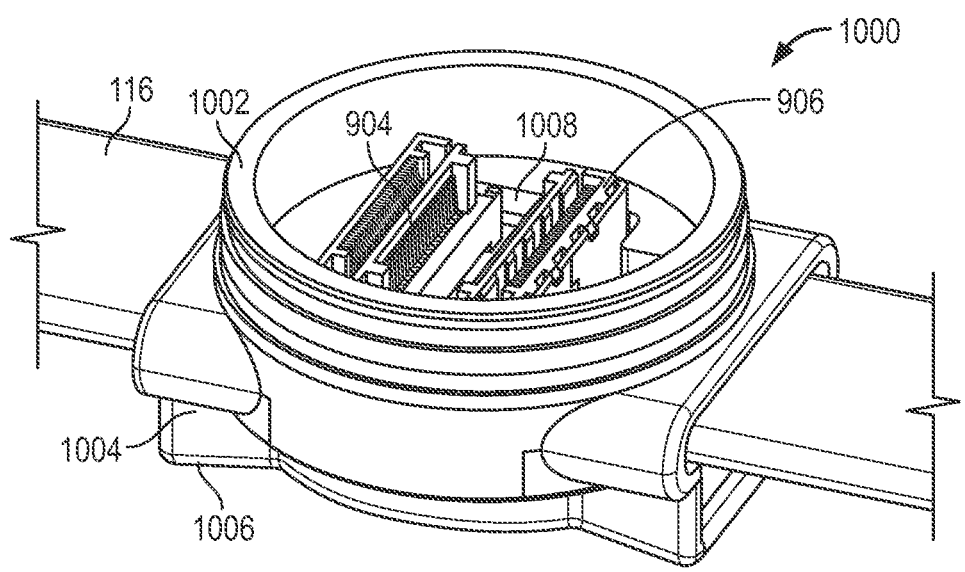
FIG. 10B is a perspective view of the example connection port shown in FIG. 10A.

FIG. 10A is an exploded view of an example cup 1000 that may be used in place of the cup 902 of FIGS. 9A-9C. FIG. 10B is an assembled view of the example cup 1000. The example cup 1000 provides extra strength relative to the cup of 902 of FIGS. 9A-9C and assists in securing the portion of the central strip 116 and PCB 232 around the connection hub 900 to prevent the FPCB 232 from bending too much and potentially detaching from the fourth and fifth connectors 904, 906. The example cup 1000 of FIGS. 10A and 10B includes a top portion 1002, a bottom portion 1004, and a clip 1006. The top and bottom portions 1002, 1004 are operatively coupled together on the top and bottom of the central support strip 116. The clip 1006 attaches to the bottom of the bottom portion 1004 and further prevents the top and bottom portions 1002, 1004 from bending.

As shown in FIGS. 10A and 10B, the top portion 1002 of this example has an opening 1008 to receive the fourth and fifth connectors 904, 906. The top portion 1002 also includes a first annular groove 1010 and a second annular groove 1012, which may be used, for example, to receive retainer rings (e.g., retainer rings 908, 910).

Figure 11A:
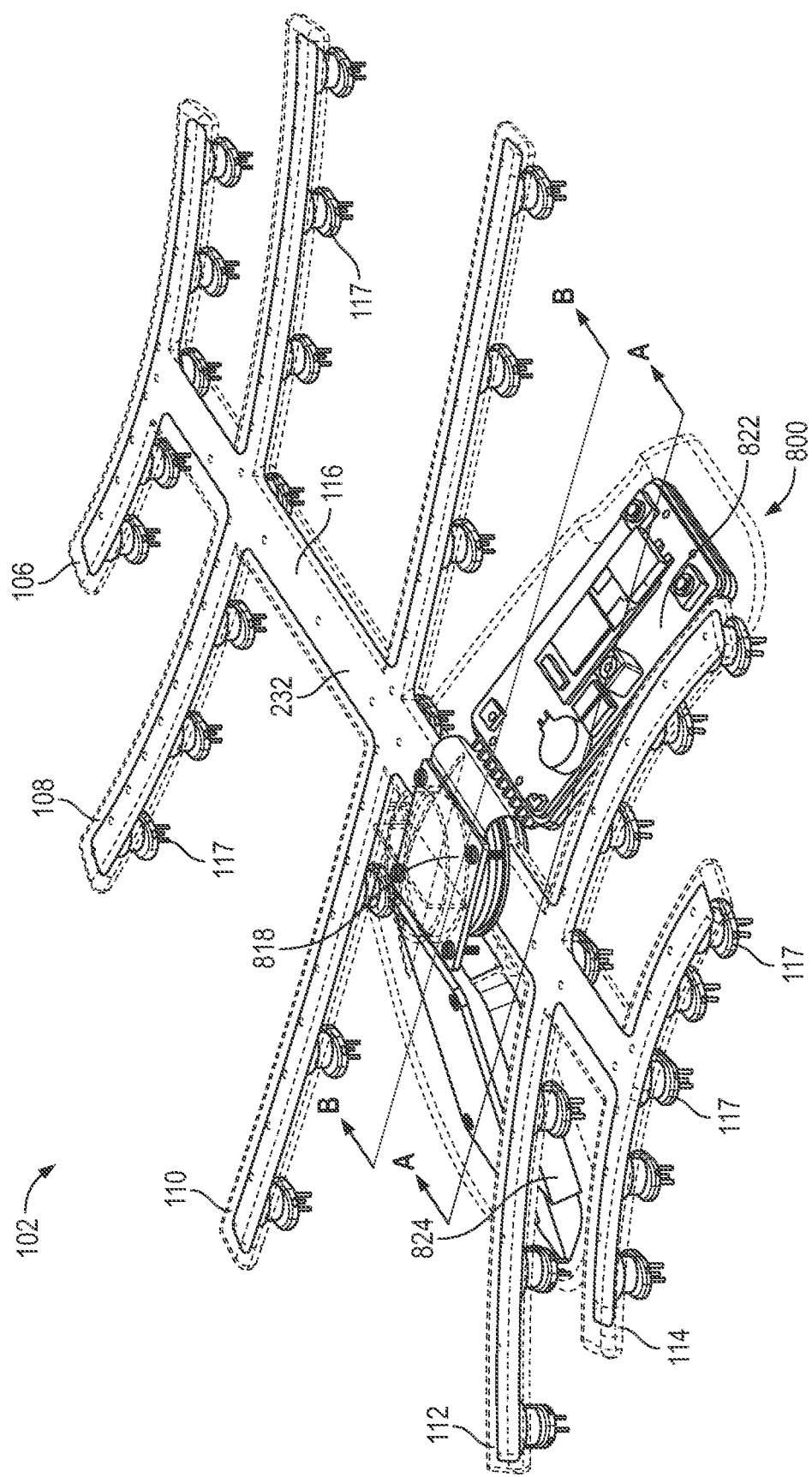
FIG. 11A is a perspective view of the example processing unit of FIG. 8A coupled to the example electrode assembly of FIG. 1A.

FIG. 11A illustrates the example processing unit 800 coupled to the electrode assembly 102 of the example headset 100 of FIGS. 1A-1E. In this illustrated example, the shell of the electrode assembly 102 is shown in dashed lines to expose the FPCB 232, and the housing 802 of the processing unit 800 is also shown in dashed lines to expose the internal components (e.g., the circuit board 818, the processor 822, the battery 824) of the processing unit 800. When coupled to the electrode assembly 102, the two ends of the processing unit 800 are curved or angled downwards. This allows the processing unit 800 to remain close to the head of a user and reduce the risk of the processing unit 800 getting snagged or caught on foreign objects and to provide greater stability for the headset 100. The PCB 232 of the illustrated example transfers the signals gathered by the electrode units 117 from the first, second, third, fourth and fifth strips 106-114 to the processing unit 800 to be processed. In the example of FIG. 11A, one side of the processing unit 170 includes the processor 822 and the other side the processing unit 800 includes the battery 824. The processor 822 and the battery 824 are operatively coupled to the circuit board 818 inside the housing 802.

Figure 11B:
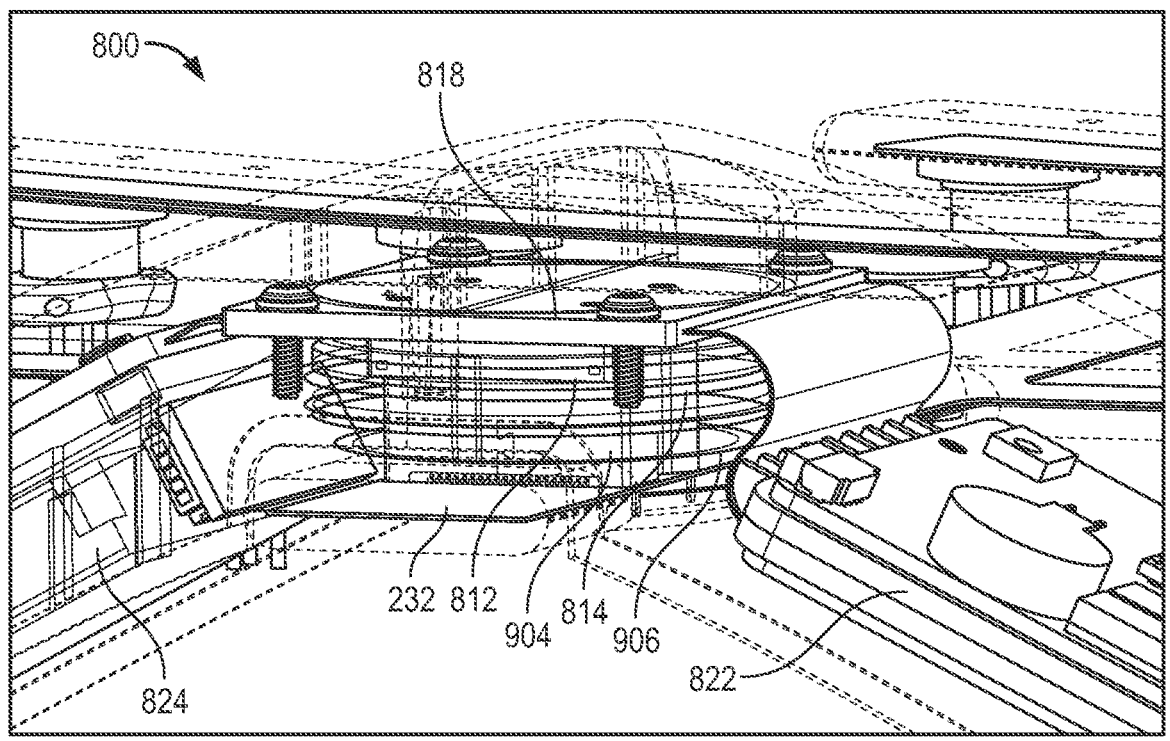
FIG. 11B is a cross-sectional view of the example processing unit of FIG. 8A coupled to the example electrode assembly in FIG. 11A taken along the line A-A of FIG. 11A.

FIG. 11B is a cross-sectional view of the headset 100 taken along line A-A of FIG. 11A through the PCB 232. The shell of the electrode assembly 102 and the housing 802 of the processing unit 800 are shown in dashed lines to expose the PCB 232 and the inner components (e.g., the circuit board 818, the processor 822, the battery 824) of the processing unit 800. The first connector 812 is connected to the fourth connector 904 and the second connector 814 is connected to the fifth connector 906.

Figure 11C:
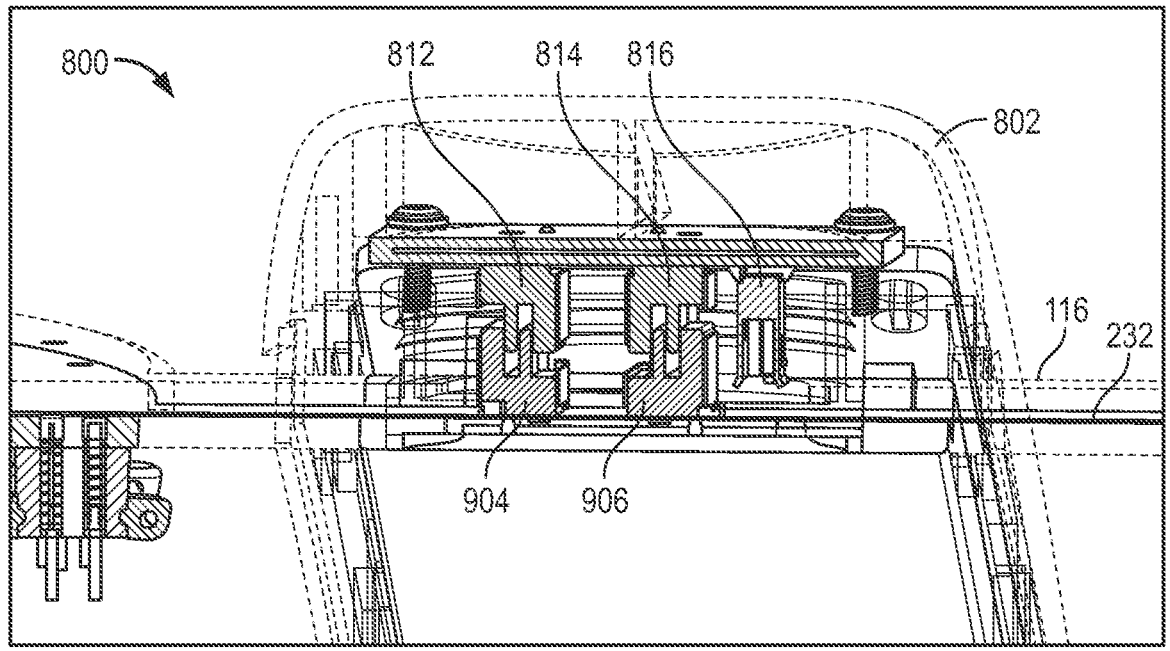
FIG. 11C is another cross-sectional view of the example processing unit of FIG. 8A coupled to the example electrode assembly in FIG. 11A taken along the line B-B of FIG. 11A.

FIG. 11C is a cross-sectional view of the example headset 100 taken along line B-B of FIG. 11A through the processing unit 800. As shown, the first connector 812 of the processing unit 800 couples to the fourth connector 904 of the connection port 900 and the second connector 814 of the processing unit 800 couples to the fifth connector 906 of the connection port 900. In this example, the first, second, fourth and fifth connectors 812, 814, 904, 906 are forty-pin interlocking connectors. The pins of the first, second, fourth and fifth connectors 812, 814, 904, 906 are communicatively coupled to transfer electrical signals therebetween.

Figure 12:
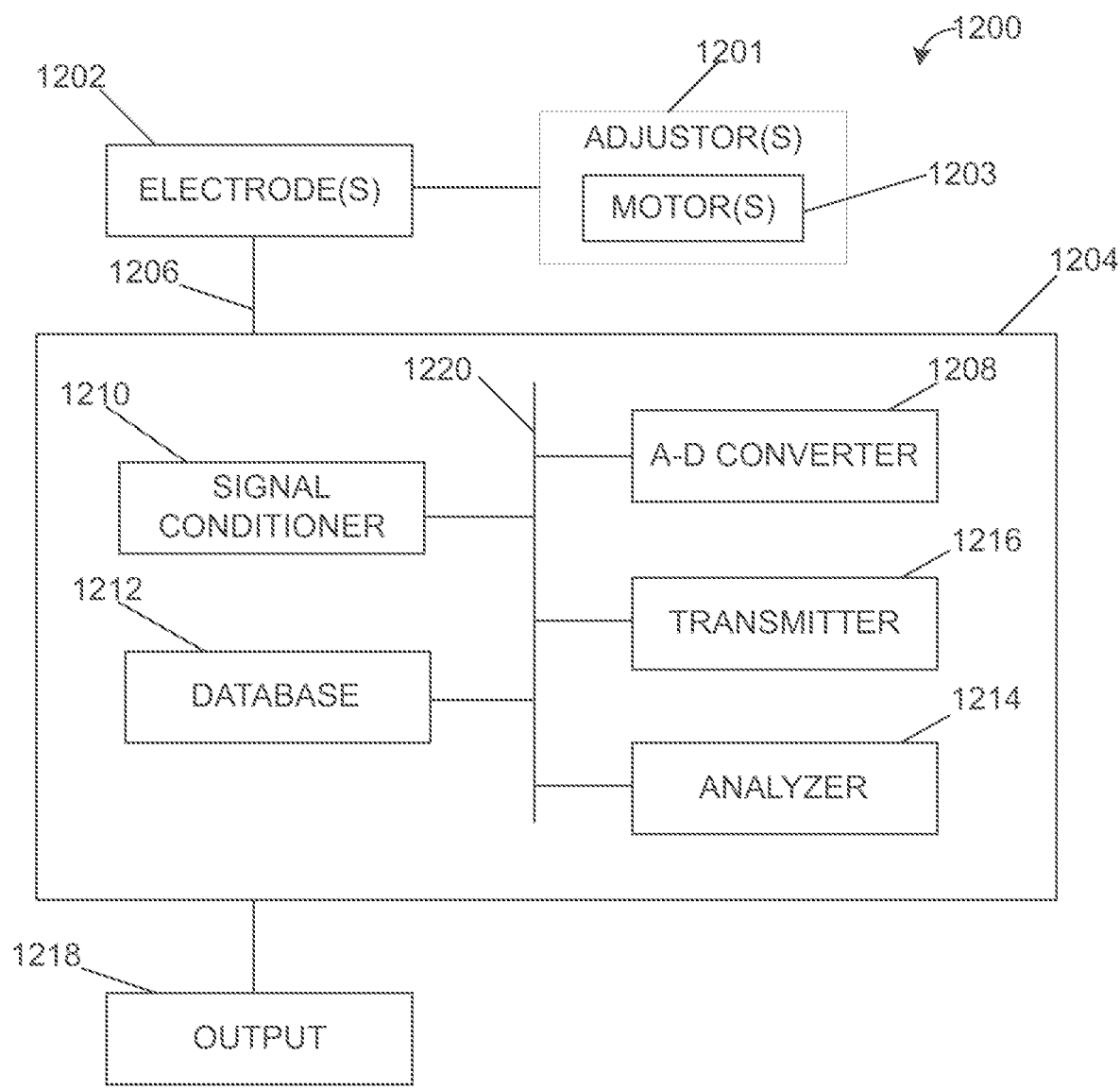
FIG. 12 is a block diagram of an example circuit from the headset in FIG. 1A.

FIG. 12 is a block diagram of an example processing system 1200 for use with the example headset 100 and/or the example headset 300. The example system 1200 includes a plurality of electrodes 1202 such as, for example, the electrodes (e.g., the electrodes 212, 214, 216, 516, 518, 614, 616) in the electrode units 117 of the example headset 100 or the electrodes in the electrode units 320, 321 of the example headset 300. The electrodes 1202 are coupled, for example, to a headset to be worn on a head of a subject, such as, for example, in the example headset 100 or the example headset 300 disclosed above.

The electrodes 1202 are also communicatively coupled to a processing unit 1204 (e.g., the processing unit 170 of the headset 100 shown in FIGS. 1A-1E, the processing unit 315 of the headset 300 shown in FIGS. 3A-3C and/or the processing unit 800 shown in FIGS. 8A, 8B and 11A-C) via a communication link 1206, which may be for example a wired or wireless communication link including, for example, the FPCB 232 disclosed above. The communication link 1206 may be, for example, incorporated in the strips 106-114 and/or the central support member 116 of the headset 100 or in the strips 304-312 and/or the central support member 314 of the headset 300.

The electrodes 1202 are coupled to adjustor(s) 1201. The adjustors 1201 adjust the position of the electrodes 1202 relative to the head of the subject and/or relative to other ones of the electrodes 1202. Example adjustors 1201 include the example adjustors 142-152 disclosed above in connection with the headset 100, which are operatively coupled to the example electrodes (e.g., in the example units 117) via the example strips 106-114 and the example tension straps 118-136. An example adjustor 1201 also includes the example adjustor 358 disclosed above in connection with the headset 300, which is operatively coupled to the example electrodes (e.g., in the example units 320, 321) via the example strips 304-312 and the example tension straps 322-356. In addition, as disclosed above, in some examples, the adjustors 1201 are rotatable wheels, and in some examples, the adjustors 1201 are automatically operate using, for example, one or more motor(s) 1203.

The example processing unit 1204 includes an analog-to-digital converter 1208, a signal conditioner 1210, a database 1212, an analyzer 1214 and a transmitter 1216. In the example headset 100 disclosed above, the analog-to-digital converter 1208, the signal conditioner 1210, the database 1212, the analyzer 1214 and/or the transmitter 1216 may be incorporated into the processing unit 170. In the example headset 300 disclosed above, the analog-to-digital converter 1208, the signal conditioner 1210, the database 1212, the analyzer 1214 and/or the transmitter 1216 may be incorporated into the processing unit 315. Additionally and or alternatively, the analog-to-digital converter 1208, the signal conditioner 1210, the database 1212, the analyzer 1214 and/or the transmitter 1216 may be incorporated into the processor 822 of the processing unit 800, which may be used with the example headsets 100 and/or 300. In other examples, analog-to-digital conversion, signal conditioning, analysis and transmission may occur closer to the source such as, for example in the housings 202, 502, contact member 206 and/or base 520.

The analog-to-digital converter 1208 converts the analog signals received at the electrodes 1202 to digital signals. In some examples, the analog-to-digital converter 1208 is located in the processing unit 1204 in the housing of the headset. In other examples, the analog-to-digital converter 1208 comprises multiple A-D converters located to service individual or sets of the electrodes to convert the signals as close to the source as possible, which may further reduce interference. In some examples, the A-D converters are disposed within housings of electrode units that each have one or more electrodes (e.g., the electrode unit 117).

The signal conditioner 1210 of the illustrated example prepares the gathered signals so that the data is in a more usable form. For example, the signal conditioner 1210 may include an amplifier to amplify the signal to a more detectable level. In addition, the signal conditioner 1210 may include a filter to remove noise from the signal. The filter may also be used as a bandpass filter to pass one or more frequency bands and/or manipulate select bands depending on the desired processing and/or analysis. In some examples, each of the electrodes 1202 may include a signal conditioner at or near the electrode 1202. The example signal conditioner 1210 may include hardware and/or software to execute a signal conditioning method. In some examples, the signal conditioner includes a detrending unit to compensate for electrode polarization, in which there is slow movement of the voltage signal unrelated to brain wave activity due to polarization of the electrodes. The example processing unit 1204 also provides signal processing that may include hardware and/or software to execute Fast Fourier Transform (FFT) calculations, coherence measurements and/or custom adaptive filtering.

The analyzer 1214 is to analyze the data gathered from the electrodes 1202 and processed by the analog-to-digital converter 1208 and the signal conditioner 1210 in accordance with one or more analysis protocols depending on the desired study. For example, in accordance with some studies, the analyzer 1214 may process the data to determine one or more of a subject's mental state, physiological state, attention, resonance or memory, emotional engagement and/or other suitable characteristics of the subject.

The transmitter 1216 communicates the data at any stage of processing and/or the results of the analysis from the analyzer 1214 to an output 1218. The output 1218 could be a handheld device, an alarm, a display screen on the headset, a remote server, a remote computer and/or any other suitable output. Data transmission may be implemented by Bluetooth transmission, wi-fi transmission, ZiGBee transmission and/or encryption before transmission. In the illustrated example, the database 1212 stores all data gathered streams. The streams can be buffered for streaming or stored onboard (i.e., at the headset) for periodic or aperiodic uploads during, for example, low-activity periods.

The processing unit 1204 components 1208-1216 are communicatively coupled to other components of the example system 1200 via communication links 1220. The communication links 1220 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.). Also, the components of the example system 1200 may be integrated in one device or distributed over two or more devices.

While an example manner of implementing the system 1200 is illustrated in FIG. 12, one or more of the elements, processes and/or devices illustrated in FIG. 12 may be combined, divided, re-arranged, omitted, eliminated and/or implemented in any other way. Further, the example processing unit 1204, the example signal conditioner 1210, the example A/D converter 1208, the example database 1212, the example transmitter 1216, the example analyzer 1214, the example output 1218 and/or, more generally, the example system 1200 of FIG. 12 may be implemented by hardware, software, firmware and/or any combination of hardware, software and/or firmware. Thus, for example, any of the example processing unit 1204, the example signal conditioner 1210, the example A/D converter 1208, the example database 1212, the example transmitter 1216, the example analyzer 1214, the example output 1218 and/or, more generally, the example system 1200 of FIG. 12 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example processing unit 1204, the example signal conditioner 1210, the example A/D converter 1208, the example database 1212, the example transmitter 1216, the example analyzer 1214 or the example output 1218 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 1200 of FIG. 12 may include one or more elements, processes and/or devices in addition to, or instead of, those illustrated in FIG. 12, and/or may include more than one of any or all of the illustrated elements, processes and devices.

Figure 13:
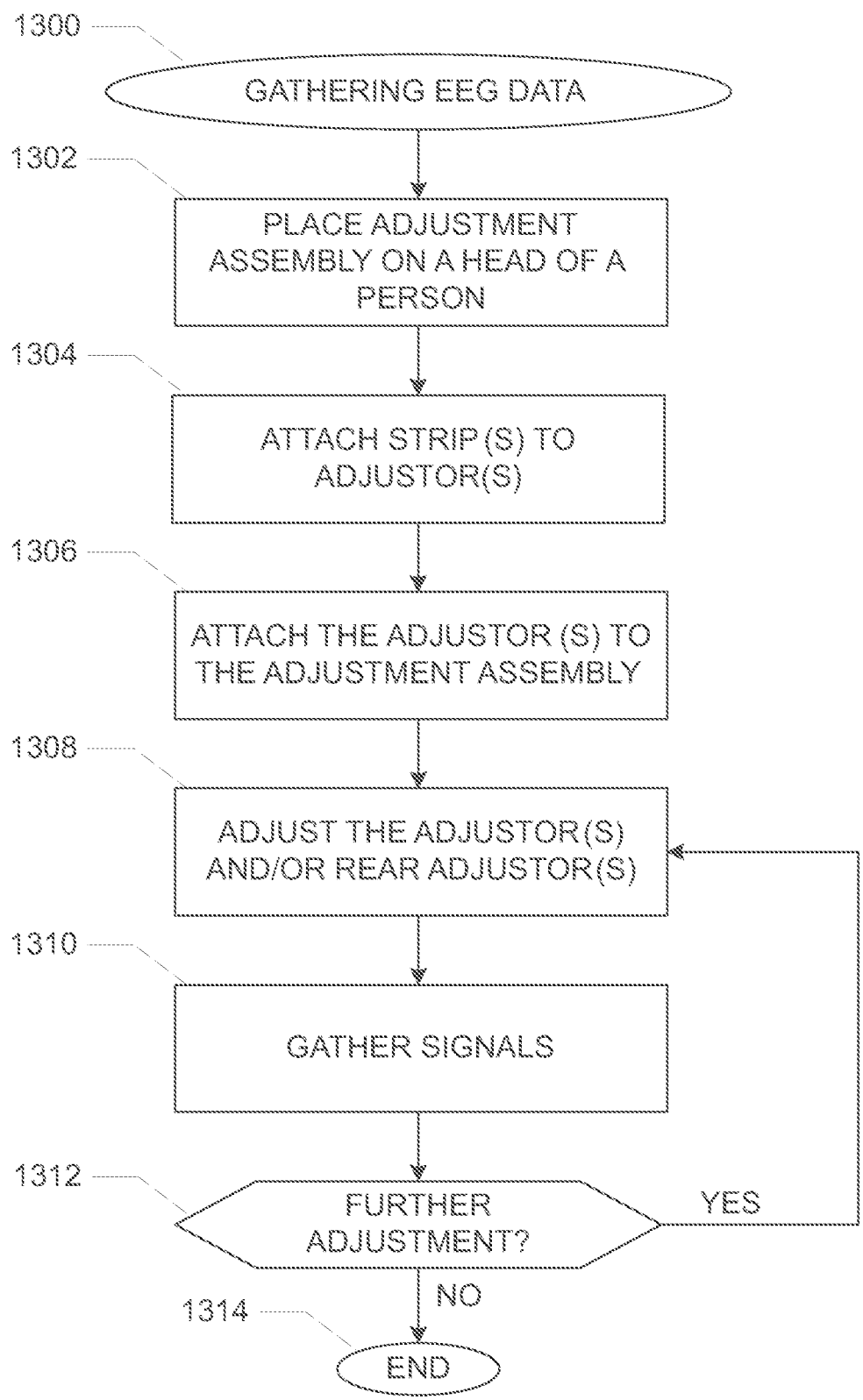
FIG. 13 is a flowchart representation of example instructions, at least some of which are machine readable, for using the example headset of FIG. 1A.
Figure 14:
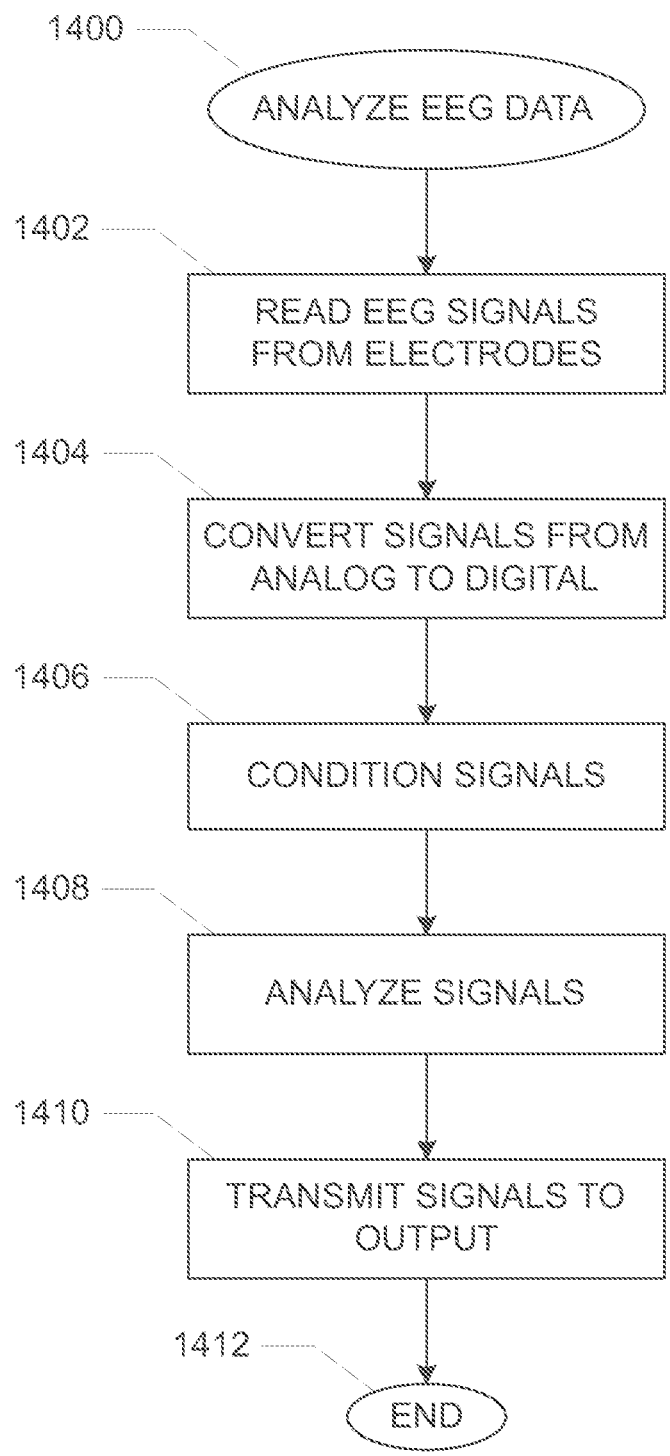
FIG. 14 is a flowchart representation of example machine readable instructions for analyzing EEG data gathered with the example headsets of FIGS. 1A and 3A.

Flowchart representations of example instructions, at least some of which are machine readable, for implementing the headset 100, the headset 300 and/or system 1200 of FIGS. 1A-12 are shown in FIGS. 13 and 14. In this example, the machine readable instructions comprise a program for execution by a processor such as the processor 1512 shown in the example processing platform 1500 discussed below in connection with FIG. 15. The program may be embodied in software stored on a tangible computer readable medium such as a CD-ROM, a floppy disk, a hard drive, a digital versatile disk (DVD), or a memory associated with the processor 1512, but the entire program and/or parts thereof could alternatively be executed by a device other than the processor 1512 and/or embodied in firmware or dedicated hardware. Further, although the example program is described with reference to the flowcharts illustrated in FIGS. 13 and 14, many other methods of implementing the example headset 100, the example headset 300 and/or example system 1200 may alternatively be used. For example, the order of execution of the blocks may be changed, and/or some of the blocks described may be changed, eliminated, or combined.

As mentioned above, the example process of FIG. 14 and at least a portion of the example process of FIG. 13 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process of FIG. 14 and at least a portion of the example process of FIG. 13 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 13 is a flowchart illustrating an example process of gathering EEG data (block 1300) that may be implemented, for example, with the example headset 100 and/or the example headset 300 disclosed herein. The example process includes placing an adjustment assembly on a head of a person (block 1302) such as, for example, the adjustment assembly 104 shown in FIGS. 1A-1E, which includes the first support 138, the second support 140, the rear support 154, the front support 156 and/or the first and second adjustment lines 158, 160. The example adjustment assembly 104 of FIGS. 1A-1E includes rubber, nylon and/or silicone components that may be stretched over the head of the person. In some examples, the adjustment assembly 104 includes the first and/or second adjustment lines 158, 160 that couple the first and second supports 138, 140, the rear support 154 and the front support 156 together. The first and second adjustment lines 158, 160 may include nylon and may stretch as the user puts the adjustment assembly on his/her head. In some examples, the first support 138 is to be disposed on the right side of the head, the second support 140 is to be disposed on the left side of the head, the rear support 154 is to be disposed on the back side of the head (e.g., below the occipital bone) and the front support 156 is to be disposed on the front of the head (e.g., on the forehead).

The adjustment assembly (block 1302) may also include, for example, the headband 316 of the headset 300 shown in FIGS. 3A-3C. The headset 300 of FIGS. 3A-3C includes an electrode assembly 302 having electrodes strips 304-312. The first electrode strip 304 is operatively coupled to the headband 316 (e.g., via the first and second tension straps 322, 324). In use, the headband 316 is stretched onto the head of a person such that the electrode assembly 302 is disposed on the top of the head of the person.

The example process 1300 includes attaching one or more strip(s) to one or more adjustor(s) (block 1304). In some examples, the strips include a plurality of electrodes and at least one tension strap that is attachable to the adjustor(s). In some examples, one or more of the strips includes two tension straps that are disposed along the electrode side of the respective strip. In other examples, multiple tensions straps are coupled to each of the strips (e.g., the example arrangement shown in FIGS. 3A-3C). In some examples, the ends of the strips are attached to a separate adjustor (e.g., via the tension straps). In other examples, two or more strips are coupled to the same adjustor.

For example, the example headset 100 of FIGS. 1A-1E includes the plurality of attachable/detachable strips 106-114 of the electrode assembly 102. The example strips 106-114 are attached to the respective adjustors 142-152 and are disposed over the head of a person. Additionally or alternatively, the example headset 300 disclosed above also includes a plurality of attachable/detachable strips 304-312 that are attached to an adjustor 358.

The example process 1300 includes attaching the adjustor(s) to the adjustment assembly (block 1306). In some examples, each of the adjustors is removably attached to the adjustment assembly. The adjustors are attached to the adjustment assembly such that the strips are disposed over the head of the user from the left side of the head to the right side of the head. The adjustors are operable to move the strips and pull the strips and their respective electrodes closer to the scalp of the user. In the example headset 100 of FIGS. 1A-1E, the first, second and third attachment devices 142, 144, 146 are attached to the first support 138 on a first side of the head, and the fourth, fifth and sixth attachment devices 148, 150, 152 are attached to the second support 140 on a second side of the head. In the example headset 300 of FIGS. 3A-3C, the adjustor 358 is coupled to the base 318 in the rear of the headset 300.

The example process 1300 includes adjusting the adjustors and rear adjustors (block 1308). The adjustors operate to move the respective strips relative to the head. As disclosed above, in some examples, the strips include one or more tension straps that are slidably connected to the strips. The tension straps are coupled to the adjustors, and the adjustors operate to change the tension in the tension straps to move the strips on the head of the user. By increasing tensions in the tension straps, the strips and the respective electrode units are pulled closer to the scalp of the user.

In some examples, the adjustors comprise wheels that are rotatably attached to the adjustment assembly. The tension straps are attached to the wheels such that as a wheel is turned, the effective length of the associated tension strap(s) is changed (e.g., more tension or less tension). In some examples, the adjustors are automatic and may include a motor or be coupled to a motor to adjust the tension in the tension straps.

In some examples, the adjustment assembly also includes one or more rear adjustors to adjust the location of the side supports on the right and left sides of the head.

In some examples, a rear support includes a first adjustment line that is connected to the two side supports and a front support. A first rear adjustor operates to move the side supports toward the back of the head and, thus, decrease the distance between the rear support and the two side supports. In some examples, the rear support also includes a second adjustment line that is also coupled to the two side supports and the front support. In this example, the second adjustment line is positioned below the ears to bias the two side supports downward on the head of the user. In some examples, the rear support includes a second rear adjustor to operate/change the tension in the second adjustment line to move the two side supports and, thus, the adjustors and the respective strips.

In the example headset 100 of FIGS. 1A-1E, the tension straps 118-136 are attached to the respective adjustors 142-152 on the first and second supports 138, 140. A user may adjust one or more of the adjustors 142-152 (block 1308) to change the tension in one or more of the tension elements 118-136 to move one or more of the respective strips 106-114 and tighten one or more of the strips 106-114 against the scalp of the user. In the illustrated example of FIGS. 1A-1E, the adjustment assembly 104 also includes the first and second adjustment lines 158, 160 that are slidably received by the rear support 154 and coupled to the first and second supports 138, 140 and the front support 156. In some examples, the first rear adjustor 162 is adjusted (block 1308) to change the tension in the first adjustment line 158 and, thus, move the first and second supports 138, 140. In some examples, the rear support 154 also includes the second rear adjustor 164 that is adjusted (block 1308) to change the tension in the second adjustment line 160. The example rear support 154 includes guides 166, 168 (e.g., a third support and a fourth support) to direct the second adjustment line 160 below the ears of the user and below the first and second supports 138, 140, such that changing the tension of the second adjustment line 160 moves the first and second supports 138, 140 downward on the head.

Additionally or alternatively, in the example headset 300 of FIGS. 3A-3C, each of the tension straps 322-356 is operatively connected to the first strip 304 and/or the headband 316 on one end and to the adjustor 358 on the opposite end. The tensions straps 322-356 are slidably coupled to the respective electrodes units 320, 321, which are operatively coupled to the respective electrode strips 304-312. The adjustor 358 is attached to the base and a user may adjust the adjustor 358 (block 1308) to change the tension in the tension straps 322-356 to move the strips 304-312 toward the scalp of the user.

In addition, the example process 1300 includes gathering signals from the electrodes of the headset (block 1310). The signals may be monitored, analyzed, manipulated, etc. In the example headsets 100, 300 of FIGS. 1A-1E and 3A-3C, the signals from the electrode units 117, 320, 321 are transferred to the processing unit 170, 315 where at least some of the conditioning and/or processing may occur. Additionally, example processing unit 800 may be used with the example headsets 100, 300 to gather/receive signals from the respective electrodes.

The example process 1300 also includes determining if the headset requires further adjusting (block 1312). In some examples, the adjustors and/or the rear adjustors operate to move the electrode assembly on the head of the user and increase the pressure of the electrodes on the head of the user. If further adjusting is desired (e.g., if the signals are weak and/or the subject is experiencing discomfort), the adjustors and/or the rear adjustors can be further adjusted (block 1308). With the headset adjusted, the example process 1300 gathers signals from the electrodes (block 1310).

If further adjustment is not needed (block 1312) and the monitoring is complete, the example process 1300 ends (block 1314).

FIG. 14 is a flowchart representative of example instructions which may be executed to analyze EEG data (block 1400) collected from the example headset 100 of FIGS. 1A-1E and/or the example headset 300 of FIGS. 3A-3C. For example, the example headset 100 has a plurality of electrodes that contact the scalp of a subject to receive electrical signals from the subject's brain. The example process of analyzing EEG data (block 1400) includes reading the EEG signals from the electrodes (block 1402). In the illustrated example, the signals are converted from an analog signal to a digital signal (block 1404). In some examples, the analog-to-digital conversion takes place in a processing unit, such as, for example, the processing unit 1204 of the example system 1200. In other examples, the analog-to-digital conversion takes place adjacent the electrodes within the headset to convert the signal as close to the source as possible, examples of which are disclosed above.

In the illustrated example, the signals are conditioned (block 1406) to improve the usefulness of the signals and the accessibility of the data contained therein. For example, as disclosed above, the conditioning may include amplifying the signals and/or filtering the signals (e.g., with a bandpass filter).

The signals are analyzed (block 1408) to, for example, determine a mental state of the subject, a health condition, an engagement with media as an audience member or effectiveness of the media, or an input desire for an electrical device. For example, the EEG data may be analyzed to evaluate brain activity in particular frequency bands of the EEG data and/or in particular regions of the brain. Assessments and/or calculations of the relationship(s) and correlation(s) of the frequency bands and regions of activity of the EEG data may be used to determine an emotional or mental state of a person including, for example, attention, emotional engagement, memory or resonance, etc. A description of other processing operations and techniques is disclosed in U.S. patent application Ser. No. 13/829,849 titled "METHODS AND APPARATUS TO GATHER AND ANALYZE ELECTROENCEPHALOGRAPHIC DATA," filed Mar. 14, 2013, which is incorporated herein by reference in its entirety.

In the illustrated example, the signals (e.g., the results of the analysis) are transmitted to an output (block 1410), such as, for example, the output 1218 of the example system 1200. Example modes of output are include, for example, sounding an alarm, displaying a message and/or other alert on a screen, issuing a report to a local and/or remote computer and/or any other suitable output. In addition, the output may include the wired or wireless communications detailed herein. In some examples, the output includes data reflected of a person paying attention, the person not paying attention, the person in a state of semi-involvement with a media program, or other mental state of the person, and the identity of the program are transmitted to, for example a remote data facility. Raw data, processed data, a history log or an indicator of audience measurement also may be transmitted to the remote data for collection. The remote data facility may be, for example, a marketing company, a broadcast company, an entertainment studio, a television network and/or any other organization that might benefit from or otherwise desire to know when people are and/or are not focused on broadcast programs and what those programs are. This example allows broadcasting companies and/or marketing personnel to analyze which programs people are watching, when they are watching the programs and/or when they are focused during the broadcast. After the output (block 1410), the example process 1400 ends (block 1412).

Figure 15:
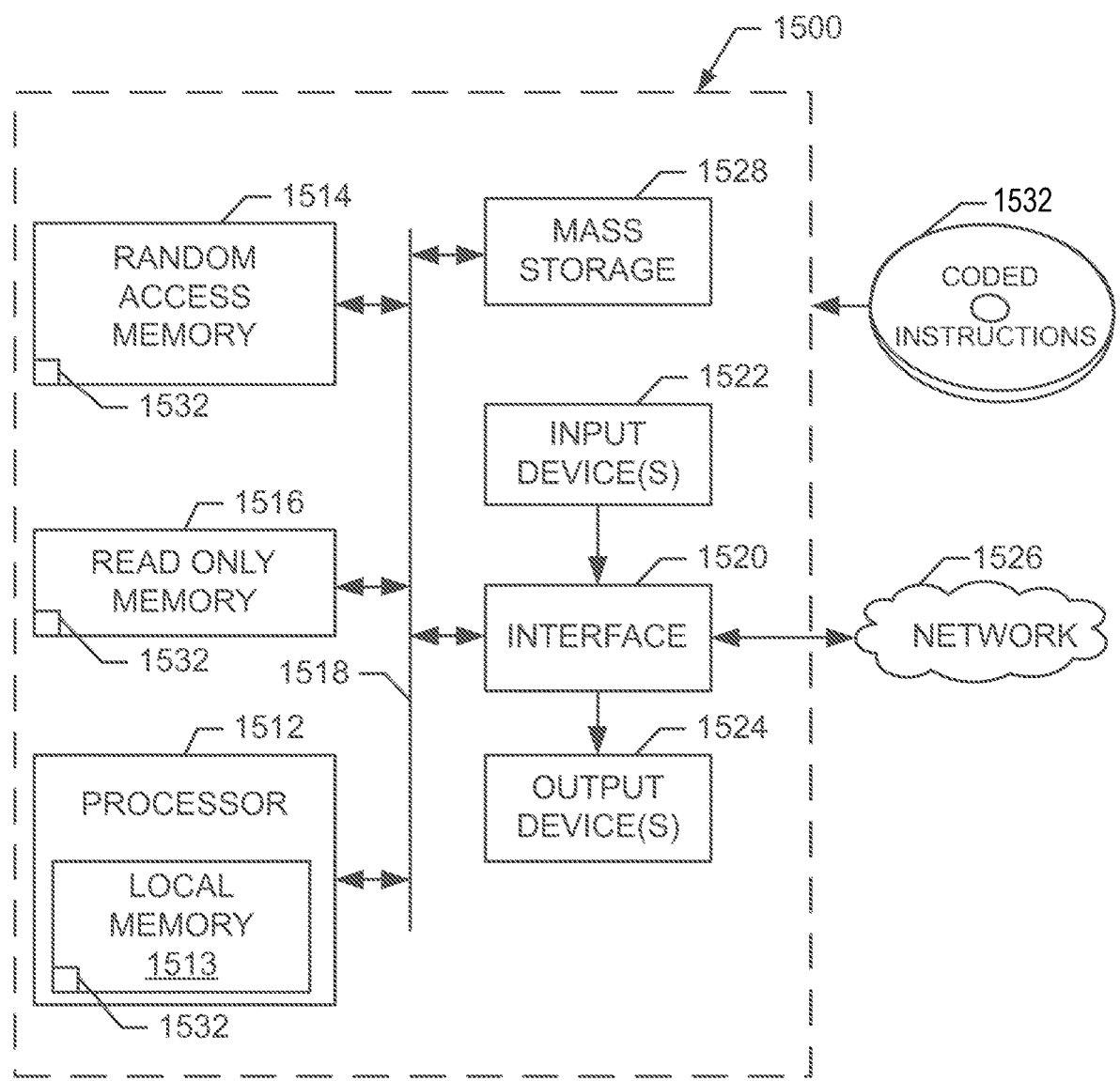
FIG. 15 illustrates an example processor platform that may execute one or more of the instructions of FIGS. 13 and/or 14 to implement one or more of the example headset of FIGS. 1A-1E, the example headset of FIGS. 3A-3C, or the example circuit of FIG. 12.

FIG. 15 is a block diagram of an example processing platform 1500 capable of executing the one or more of the instructions of FIGS. 13 and 14 to implement one or more portions of the apparatus and/or systems of FIGS. 1A-1E, 2A-2C, 3A-3C, 4, 5A-5D, 6, 7A-7C, 8A-8B, 9A-9C, 10A-10B, 11A-11C, and 12. The processing platform 1500 can be, for example, a processor in a headset, a server, a personal computer, a mobile device (e.g., a cell phone, a smart phone, a tablet such as an iPad™), a personal digital assistant (PDA), an Internet appliance and/or any other type of computing device.

The processor platform 1500 of the illustrated example includes a processor 1512. The processor 1512 of the illustrated example is hardware. For example, the processor 1512 can be implemented by one or more integrated circuits, logic circuits, microprocessors or controllers from any desired family or manufacturer.

The processor 1512 of the illustrated example includes a local memory 1513 (e.g., a cache). The processor 1512 of the illustrated example is in communication with a main memory including a volatile memory 1514 and a non-volatile memory 1516 via a bus 1518. The volatile memory 1514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1516 may be implemented by flash memory and/or any other desired type of memory device. Access to the main memory 1514, 1516 is controlled by a memory controller.

The processor platform 1500 of the illustrated example also includes an interface circuit 1520. The interface circuit 1520 may be implemented by any type of interface standard, such as an Ethernet interface, a universal serial bus (USB), and/or a PCI express interface.

In the illustrated example, one or more input devices 1522 are connected to the interface circuit 1520. The input device(s) 1522 permit(s) a person to enter data and commands into the processor 1512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1524 are also connected to the interface circuit 1520 of the illustrated example. The output devices 1524 can be implemented, for example, by display devices (e.g., a light emitting diode (LED), an organic light emitting diode (OLED), a liquid crystal display, a cathode ray tube display (CRT), a touchscreen, a tactile output device and or a light emitting diode (LED). The interface circuit 1520 of the illustrated example, thus, typically includes a graphics driver card, a graphics driver chip or a graphics driver processor.

The interface circuit 1520 of the illustrated example also includes a communication device such as a transmitter, a receiver, a transceiver, a modem and/or network interface card to facilitate exchange of data with external machines (e.g., computing devices of any kind) via a network 1526 (e.g., an Ethernet connection, a digital subscriber line (DSL), a telephone line, coaxial cable, a cellular telephone system, etc.).

The processor platform 1500 of the illustrated example also includes one or more mass storage devices 1528 for storing software and/or data. Examples of such mass storage devices 1528 include floppy disk drives, hard drive disks, compact disk drives, Blu-ray disk drives, RAID systems, and digital versatile disk (DVD) drives.

The coded instructions 1532 of FIGS. 13 and 14 may be stored in the mass storage device 1528, in the volatile memory 1514, in the non-volatile memory 1516, and/or on a removable tangible computer readable storage medium such as a CD or DVD.

Although certain example apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. A method comprising:
adjusting a first adjustor to cause a first tension change in a first tension strap operatively coupled between a first support and a second support, the first support to be disposed on a first side of a head of a person and the second support to be disposed on a second side of the head of the person opposite the first side of the head of the person, the first tension change to cause the first tension strap to slide relative to a first electrode strip including a first electrode pin to thereby cause the first electrode strip to move to adjust a first distance of the first electrode strip relative to the head, the first electrode strip to be disposed over the head of the person such that a first end of the first electrode strip is disposed adjacent the first support and a second end of the first electrode strip is disposed adjacent the second support; and
gathering a first set of signals from the head using the first electrode pin.

2. The method of claim 1, further including adjusting a second adjustor operatively coupled to the second support to cause a second tension change in the first tension strap.

3. The method of claim 1, wherein adjusting the first adjustor causes a second tension change in a second tension strap operatively coupled between the first support and the second support, the second tension change to cause the second tension strap to slide relative to a second electrode strip including a second electrode pin to thereby cause the second electrode strip to move to adjust a second distance of the second electrode strip relative to the head.

4. The method of claim 1, further including changing an effective length of the first tension strap by adjusting the first adjustor.

5. The method of claim 1, wherein adjusting the first adjustor includes rotating a wheel.

6. The method of claim 1, wherein adjusting the first adjustor includes actuating an electric motor.

7. The method of claim 1, further including detaching the first adjustor from the first support to remove the first electrode strip.

8. The method of claim 1, further including adjusting a second adjustor to alter a position of a third support to be disposed under a right ear of the person and a fourth support to be disposed under a left ear of the person relative to the first support, which is to be disposed above a right ear of the person, and the second support, which is to be disposed above a left ear of the person.

9. The method of claim 1, wherein adjusting the first adjustor causes the first electrode pin to retract or extend from a first housing operatively coupled to the first electrode strip.

10. The method of claim 1, further including adjusting a second adjustor to cause a second tension change in a second tension strap operatively coupled between the first support and the second support, the second tension change to cause the second tension strap to slide relative to a second electrode strip including a second electrode pin to thereby cause the second electrode strip to move to adjust a second distance of the second electrode strip relative to the head.

11. The method of claim 10, wherein the first tension strap is operatively coupled to the first support via the first adjustor and the second tension strap is operatively coupled to the second support via the second adjustor.

12. The method of claim 10, wherein the first electrode strip and the second electrode strip extend over the head of the person from a left side of the head to a right side of the head.

13. The method of claim 1, wherein the first tension strap is disposed between the first electrode strip and the head of the person.

14. The method of claim 1, wherein the first electrode pin extends from a housing coupled to the first electrode strip, the housing disposed between the first electrode strip and the head of the person, the housing including a first channel, the first tension strap extending through the first channel.

15. The method of claim 14, wherein the housing includes a second channel, and wherein adjusting the first adjustor adjuster causes a second tension change in a second tension strap operatively coupled between the first support and the second support, the second tension strap extending through the second channel.

16. The method of claim 15, wherein the first tension strap and the second tension strap traverse along a longitudinal axis of the first electrode strip.

17. The method of claim 14, wherein the first electrode pin extends from a bottom surface of the housing, the bottom surface being curved to substantially conform to a curve of the head of the person.

18. The method of claim 1, wherein a first end of the first tension strap is coupled to the first support via the first adjustor.

19. The method of claim 1, wherein the first side is a left side of the head of the person and the second side is a right side of the head of the person.

20. The method of claim 1, wherein the first end of the first electrode strip is spaced apart from the first support and the second end of the first electrode strip is spaced apart from the second support.

* * * * *

UNITED STATES PATENT AND TRADEMARK OFFICE
CERTIFICATE OF CORRECTION

PATENT NO. : 11,141,108 B2
APPLICATION NO. : 15/449564
DATED : October 12, 2021
INVENTOR(S) : Yakob Badower et al.

It is certified that error appears in the above-identified patent and that said Letters Patent is hereby corrected as shown below:

In the Claims

Claim 15
Column 36, Line 36:
Delete "adjuster"

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*